(12) United States Patent
Nunokawa et al.

(10) Patent No.: US 6,703,421 B1
(45) Date of Patent: Mar. 9, 2004

(54) METHODS OF USING PHENYLMETHYLBENZOQUINONE AND HYDROQUINONE COMPOUNDS FOR TREATMENT OF MYOCARDITIS, DILATED CARDIOMYOPATHY AND HEART FAILURE

(75) Inventors: Yoichi Nunokawa, Toyonaka (JP); Akira Matsumori, Minoo (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 60 days.

(21) Appl. No.: 09/856,072

(22) PCT Filed: Sep. 18, 2000

(86) PCT No.: PCT/JP00/06364

§ 371 (c)(1),
(2), (4) Date: May 17, 2001

(87) PCT Pub. No.: WO01/21206

PCT Pub. Date: Mar. 29, 2001

(30) Foreign Application Priority Data

Sep. 17, 1999 (JP) .......................................... 11-264682

(51) Int. Cl.[7] ...................... A61K 45/00; A61K 31/122; A61K 31/192; A61P 9/04
(52) U.S. Cl. ...................... 514/532; 514/544; 514/570; 514/621; 514/622; 514/679; 514/733; 514/736; 560/51; 560/57; 562/459; 562/468; 564/169; 564/171; 568/325; 568/744
(58) Field of Search ..................... 560/51, 57; 562/459, 562/468; 564/169, 171; 568/327, 744; 514/544, 532, 570, 621, 622, 679, 733, 736, 212.63, 217.11, 227.5, 237.5, 252.14, 255.01, 311, 316, 327, 329, 330, 349, 354, 357, 423; 540/527, 607; 544/59, 176, 332, 381; 546/164, 165, 189, 216, 217, 223, 224, 226, 297, 314, 337; 548/537, 540

(56) References Cited

U.S. PATENT DOCUMENTS 4,526,719 A 7/1985 Terao et al.
5,076,829 A * 12/1991 Wriede et al. ............... 504/291

FOREIGN PATENT DOCUMENTS

| EP | 1008346 A1 * | 6/2000 |
|---|---|---|
| GB | 1405444 | 9/1975 |
| HU | 167911 | 8/1975 |
| HU | 195767 | 5/1984 |
| JP | 62/286949 A2 * | 12/1987 |
| JP | 04/225972 A2 * | 8/1992 |
| JP | 4-226937 | 8/1992 |
| JP | 9-227561 | 9/1997 |
| JP | 10-87491 | 4/1998 |
| JP | 10/095740 A2 * | 4/1998 |
| JP | 10095740 A2 * | 4/1998 |
| WO | 97/09315 | 3/1997 |
| WO | 97/09325 | 3/1997 |
| WO | 99/40907 | 8/1999 |
| WO | 99/43346 | 9/1999 |
| WO | WO 99-48491 A1 * | 9/1999 |
| WO | 99/48491 | 9/1999 |
| WO | 00/05234 | 2/2000 |

OTHER PUBLICATIONS

Citterio, Attilio Gazzetta Chimica Italiana, 110(4), 253–8 (English) 1980.*

(List continued on next page.)

Primary Examiner—Mark L. Berch
Assistant Examiner—Tom McKenzie
(74) Attorney, Agent, or Firm—Burns, Doane, Swecker & Mathis, L.L.P.

(57) ABSTRACT

A method for prevention or treating myocarditis, dilated cardiomyopathy and heart failure comprising administering to a patient in need of such treatment a NF-κB inhibitor in a therapeutically effective amount, wherein said NF-κB inhibitor is a benzoquinone derivative represented by the following formula (I):

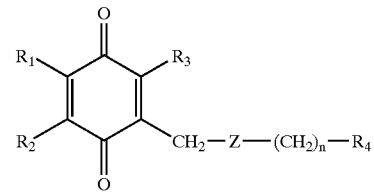

(I)

wherein $R_1$, $R_2$ and $R_3$ are each independently a hydrogen atom, an alkyl group having 1 to 5 carbons or an alkoxy group having 1 to 5 carbons;

$R^4$ is a hydrogen atom, a hydroxymethyl group, an alkyl group, or a carboxyl group which is optionally esterified or amidated;

Z is

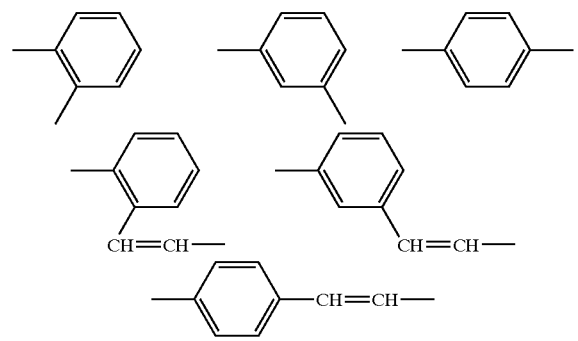

and n is an integer from 0 to 6,
or its hydroquinone form, or a pharmaceutically acceptable salt thereof, is provided.

27 Claims, 4 Drawing Sheets

OTHER PUBLICATIONS

JP 62266949 A2 (Tatsuoka et al) Dec. 12, 1987 (abstracts) Chemical Abstracts [online] Columbus, OH [retreived Mar. 28, 2003] Restreived from STN No 108:186319.*

Royer, Rene; Cheutin, Andree; Routier, Claude; Rips, Richard Bull. soc. chim. France 1297–302 1956..*

McCaskill, E. S.; Herchen, S. R., Journal of Imaging Technology, 15(3), 103–7 (English) 1989.*

Sharghi, Hashem; Eshghi, Hossein, Iranian Journal of Chemistry & Chemical Engineering, 15(2), 57–62 (English) 1996.*

Suzuki, Kenji; Tatsuoka, Toshio; Murakami, Tomiko; Ishihara, Takafumi; Aisaka, Kazuo; Inoue, Teruyoshi; Ogino, Ryoko; Kuroki, Manami; Miyazaki, Tomoko; et al., Chemical & Pharmaceutical Bulletin, 44(1), 139–44 (English) 1996.*

Bysani Chandrasekar, "Inhibition of nuclear factor kB attenuates proinflammatory cytokine and inducible nitric–oxide synthase expression in postischemic myocardium" Biochim. Biophys. Acta, vol. 1406, No. 1, 1998, pp. 91–106.

* cited by examiner

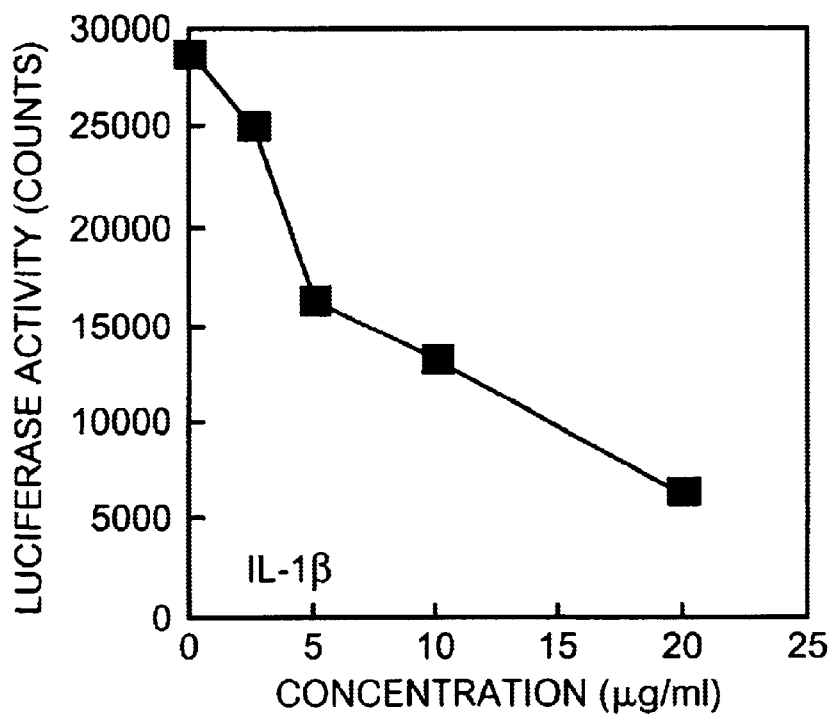
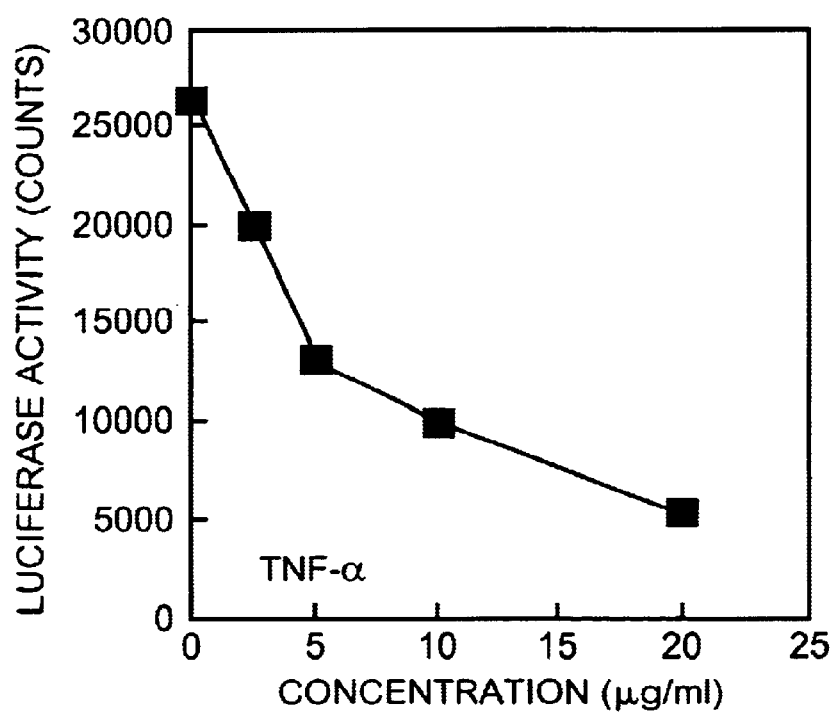

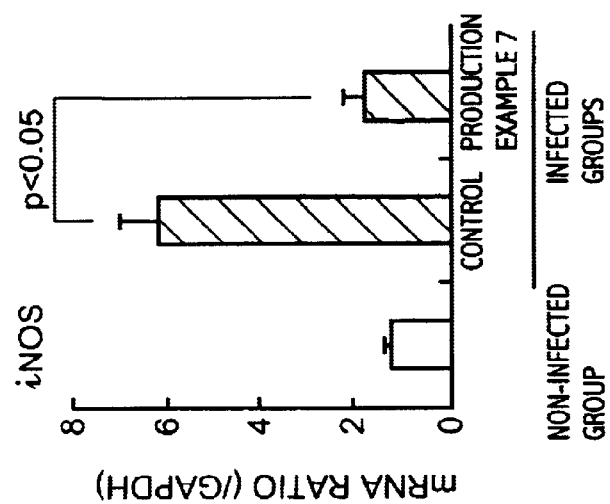
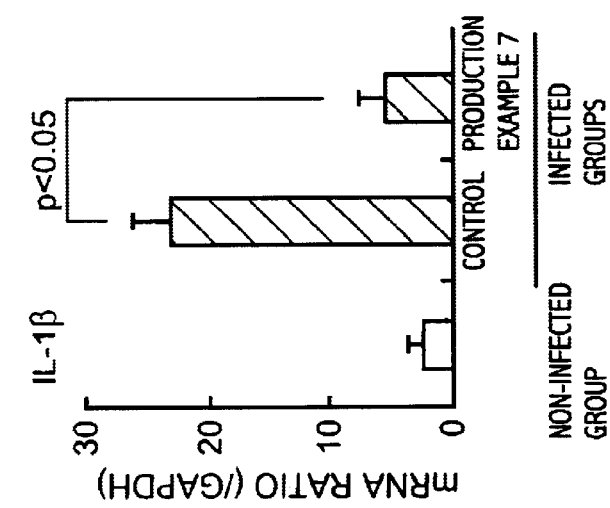
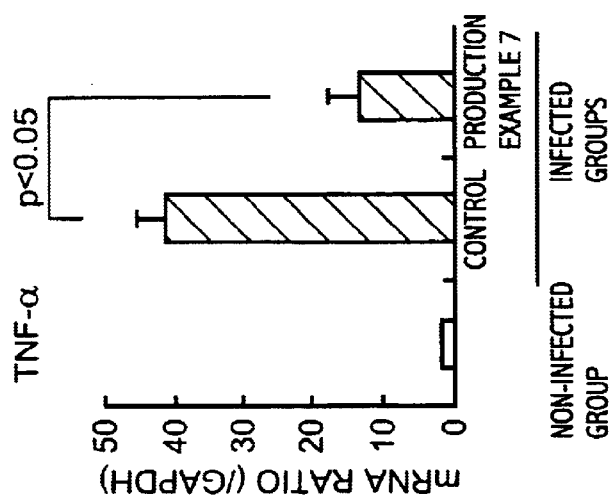

METHODS OF USING PHENYLMETHYLBENZOQUINONE AND HYDROQUINONE COMPOUNDS FOR TREATMENT OF MYOCARDITIS, DILATED CARDIOMYOPATHY AND HEART FAILURE

TECHNICAL FIELD

The present invention relates to novel drugs for prevention and treatment of myocarditis, dilated cardiomyopathy and heart failure.

BACKGROUND ART

Myocarditis is sometimes the result of infection by a virus or bacterium or a stimulus response to drugs or the like, and sometimes an autoimmunity, and it includes a group of diseases provoked by cardiomyopathy due to inflammation of cardiac muscle. A kind of myocarditis is chronic due to repeated aggravation and amelioration of the inflammation or continuous inflammation, eventually progressing to dilated cardiomyopathy.

The typical pathology of dilated cardiomyopathy includes dilation of the ventricle and contraction deficiency, and heart failure symptoms appear in 75–95% of patients, often with complications of arrhythmic death (sudden death) or thrombosis and embolism during the course of the disease. It is an intractable disease with a mortality rate of approximately fifty percent within 5 years of onset, and it accounts for half of the heart transplant patients in Europe and the U.S. It is therefore important to promptly achieve amelioration of acute myocarditis from the acute stage to prevent it from becoming chronic or intractable (Junkanki NOW, Vol.6, "Cardiomyopathy and Myocarditis", Nankodo Publishing).

No successful therapy has yet been established for this disease, and no effective therapeutic agent has been provided. It is ardently desired, therefore, to develop a drug that can suppress the necrosis of cardiac muscle cells and infiltration of inflammatory cells in myocarditis, in order to inhibit increase in heart weight and lead to improved survival rates.

Although the cause of myocarditis has not been thoroughly elucidated, reports of viral genes in cardiac muscle biopsy tissue from acute stage myocarditis and dilated cardiomyopathy patients suggest a viral infection link in almost all cases (Junkanki NOW, Vol.6, "Cardiomyopathy and Myocarditis", Nankodo Publishing).

Nitric oxide (NO) is biosynthesized from L-arginine as the substrate by NO synthase (NOs). Currently three isozymes of NOS have been found (Moncada, S. and Higgs, A. (1993) N. Eng. J. Med. 329: 2002–2012). Expression of inducible NOS (iNOs) is induced in various types of tissues and cells by endotoxins and cytokines (Forstermann U, et al. (1995) Biochem. Pharmacol. 50, 1321–1332).

Marked increase in NO production has been reported in myocarditis, dilated cardiomyopathy and heart failure patients (De Belder A J, et al. (1993) Lancet 341, 84–85; Habib F M, et al. (1996) Lancet 347, 1151–1155; Haywood G A, et al. (1994) Circulation 93, 1087–1094). Also, arginine derivatives and aminoguanidine, which are known as iNOS enzyme inhibitors, have been reported to exhibit a pharmacological effect in diseased animal models (Moncada S and Higgs E A (1995) PASEB J. 9, 1319–1330).

Thus, excess NO produced as a result of induced iNOS expression is implicated as a cause of myocarditis, dilated cardiomyopathy and heart failure.

In addition, tumor mecrosis factor (TNF)-$\alpha$, a cytokine produced from several kinds of cells including rmacrophages, is believed to be an important mediator of inflammation (Vassalli, P. (1992) Annu. Rev. Immunol. 10: 411–452). There is growing evidence that the excessive production of TNF-$\alpha$ damages normal cells and causes various pathosis (Muto, Y., et. al. (1988) Lancet 2: 72–74, Sharief, M. K. and Hentges, R. (1991) N. Engl. J. Med. 325: 467–472). Increase of TNF-$\alpha$ levels in the blood, like NO, has also been found in myocarditis, dilated cardiomyopathy and heart failure patients (Matsumori A, et al. (1994) Br. Heart J. 72, 561–566, Levine B, et al. (1990) N. Engl. J. Med. 323, 236–241). Antibodies for TNF-$\alpha$ have been demonstrated to be effective in animal models of myocarditis (Yamada T, et al. (1994) Circulation 89, 846–851).

Such findings have shown that excess production of TNF-$\alpha$ leads to and exacerbates myocarditis, dilated cardiomyopathy and heart failure, and it is therefore necessary to inhibit production of TNF-$\alpha$ as well as NO.

Interleukin (IL)-$1\beta$ also increases markedly in the blood of acute myocarditis patients, and a good correlation has been found between IL-$1\beta$ expression in chronic stage cardiac muscle and the heart/body weight ratio and extent of cardiac tissue fibrosis, in animal models of myocarditis (Shioi T, et al. (1996) Circulation 94, 2930–2937), while it has also been reported that administration of IL-$1\beta$ to animals provokes cardiomyopathy or myocarditis (Lane J R, et al. (1992) J. Exp. Med. 175, 1123–1129; Japanese Unexamined Patent Publication No. 10-273445), thus also implicating IL-$1\beta$ as one of these pathogenesis.

No therapeutic agents for cardiomyopathy or myocarditis have been reported that improve survival rates, but antibody that inhibits binding of the selectin an adhesion molecule, is being studied (Japanese Unexamined Patent Publication No. 10-273445).

Thus, iNOS, inflammatory cytokines such as TNF-$\alpha$, IL-$1\beta$, etc. and adhesion molecules have all been implicated in myocarditis, dilated cardiomyopathy and heart failure (Habib F M, et al. (1996) Lancet 347, 1151–1155). However, numerous other causatory inflammatory mediators have been found (Matsumori A (1997) Jpn. Circ. J. 61, 275–291), and the fact that these pathological factors cannot be specified to a single mediator has complicated efforts to develop effective treatment agents. Given this current situation, there are doubts against the effectiveness of treatment or prevention using, for example, antibodies that recognize one antigen or substances that inhibit binding of adhesion molecules such as selecting. Therefore, there is a desire for low molecular compounds that, instead of suppressing only expression of specific inflammatory mediators, can broadly inhibit production and expression of proteins implicated as causes of inflammation.

NF-$\kappa$B is a protein that regulates gene expression and is one of the so-called transcription factors. When normal cells are stimulated with an inflammatory cytokine such as IL-$1\beta$ and TNF-$\alpha$, a lipopolysaccharide, or ultraviolet rays, NF-$\kappa$B translocates from the cytoplasm into the nucleus where they bind to specific nucleotide sequences on the genomic DNA and thereby become involved in the expression of various genes (Blackwell, T. S. and Christman, J. W. (1997) Am. J. Respir. Cell Mol. Biol. 17: 3–9).

Although the genes coding for iNOS, inflammatory cytokines such TNF-$\alpha$ and IL-$1\beta$ and adhesion molecules such as P selectin are completely distinct genes, in the expression regulatory regions of these genomic genes, there are consensus regions to which NF-$\kappa$B binds, and activation of NF-κB has been shown to be important for expression of all of these proteins (Ghosh S, et al. (1998) Annu. Rev. Immunol. 16, 225–260).

Many genes that are involved in immunological inflammatory reactions under expression control by NF-κB are recognized, including inflammatory cytokines such as IL-6 and IL-8, as well as cell adhesion molecules such as ICAM-1, VCAM-1 and ELAM-1 or the like (Collins, T., et al. (1995) Faseb. J. 9: 899–909). Furthermore, it is known that inflammatory cytokines, when bound to receptors, transduce NF-κB-activating signals via various routes, and this fact is believed to be cause that further aggravates inflammation. Thus, the activation of NF-κB in inflammation is understood as an pathogenesis and aggravating factor of diseases (Baeuerle, P. A. and Baichwal., V. R. (1997) Adv. Immunol. 65: 111–137).

NF-κB inhibitors are characterized by inhibiting expression of iNOS, TNF-α and IL-1β at the genetic level in cells and tissues, thereby suppressing production of two or more among the inflammation mediators such as NO, TNF-α and IL-1β at once with a single agent, and they are expected to exhibit therapeutic effects against various diseases (Lee J C (1994) Ann. Report Med. Chem. 29, 235–244).

For example, the compound BAY11-7083, which has an inhibitory effect on NF-κB, is reported to exhibit an effect in rat adjuvant arthritis (Pierce J W, et al. (1997) J. Biol. Chem. 272, 21096–21103). However, very few studies have examined the effect of administering NF-κB inhibitors to animal models of specific diseases.

Several compounds are currently known as NF-κB inhibitors, such as substituted pyrimidine derivatives (WO9709315, WO9709325, J. Med. Chem., 41, 413 (1998)), xanthine derivatives (Japanese Unexamined Patent Publication No. 9-227561) and isoquinoline derivatives (Japanese Unexamined Patent Publication No. 10-87491). As compounds with excellent NF-κB inhibiting effects there may be mentioned phenylmethylbenzoquinone derivatives (WO9948491) and indan derivatives (WO0005234).

However, nothing is known about the therapeutic or preventive effects of these derivatives on myocarditis, dilated cardiomyopathy and heart failure. Moreover, no reports may be found regarding the therapeutic or preventive effects of using NF-κB inhibitors for myocarditis, dilated cardiomyopathy and heart failure. Also completely unknown are the effects of these inhibitors in terms of suppressing expression of the proteins implicated as possible pathogenesis, even for any one of the target proteins.

Thus, while excess production of numerous inflammatory substances are known for myocarditis, dilated cardiomyopathy and heart failure, and all are believed to be causative substances, no fundamental therapy exists as a countering treatment.

Problems to be Solved by the Invention

The present invention provides drugs that are useful for the prevention and treatment of myocarditis, dilated cardiomyopathy and heart failure caused by excessive production of inflammatory mediators. The invention also provides drugs which are useful for prevention and treatment of these conditions and have effects of improving survival rates for the conditions, suppressing necrosis of cardiac muscle cells and diminishing or eliminating infiltration of inflammatory cells into the heart.

Disclosure of the Invention

As a result of diligent research toward solving the aforementioned problems, the present inventors have discovered, surprisingly, that compounds with an inhibitory effect on NF-κB suppress cardiac necrosis and infiltration of inflammatory cells into normal cardiac of heart tissue. More surprisingly, it was found that survival rates are also improved, and the present invention has thus been completed.

The present invention therefore provides preventive or therapeutic agents for myocarditis, dilated cardiomyopathy and heart failure comprising NF-κB inhibitor as an active ingredient.

BRIEF DESCRIPTION OF THE DRAWINGS

FIG. 1 is a graph showing the NF-κB inhibiting effect of the compound obtained in Production Example 4.

FIG. 6 is a graph showing that the NF-κB inhibiting compound obtained in Production Example 7 inhibits expression of mRNA for inflammatory proteins in the hearts of murine models of viral myocarditis.

PREFERRED MODE OF THE INVENTION

Figure 2:
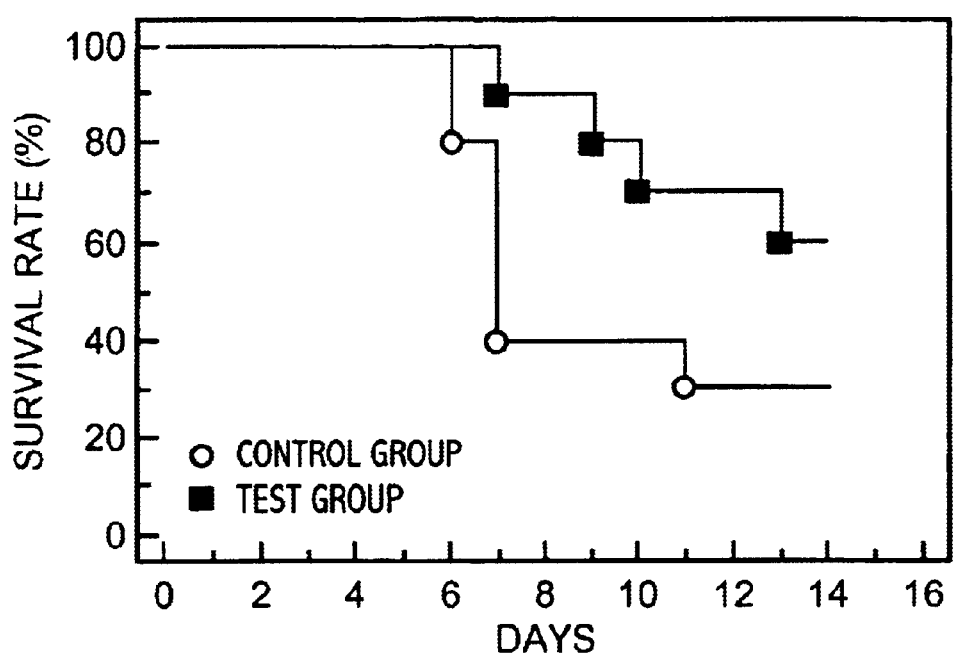
FIG. 2 is a graph showing that the NF-κB inhibiting compound obtained in Production Example 4 improves survival rates in murine models of viral myocarditis.

The NF-κB inhibitors to be used for the invention are substances capable of inhibiting activation of NF-κB, and they may be selected using a method that can be commonly carried out by a person skilled in the art (Breton J J, et al. (1997) J. Pharmacol. Exp. Ther. 282, 459–466), such as a gel shift assay employing the NF-κB binding consensus sequence or a reporter assay employing a gene including the NF-κB binding consensus sequence. An example of a selection method is described hereunder in Example 1. The method described in Japanese Unexamined Patent Publication No. 11-266872 may also be used.

The compounds that can be obtained in this manner include hitherto generally known antioxidants reported to have NF-κB inhibiting effects (Annual reports in medicinal chemistry, 29, 235–244, 1994), proteasome inhibitors (Annual reports in medicinal chemistry, 29, 235–244, 1994), kinase inhibitors (Annual reports in medicinal chemistry, 29, 235–244, 1994), anti-receptor antibodies (J. Boil. Chem. Chaturvedi, M. M. et al. 269, 14575–14583, 1994), compounds known as NF-κB inhibitors, such as hymenialdisine (Breton J J, et al. (1997) J. Pharmacol Exp. Ther. 282, 459–466), substituted pyrimidine derivatives (WO9709315, WO9709325, J. Med. Chem., 41, 413 (1998)), xanthine derivatives (Japanese Unexamined Patent Publication No. 9-227561) and isoquinoline derivatives (Japanese Unexamined Patent Publication No. 10-87491), as well as phenylmethylbenzoquinone derivatives (WO9948491) and indan derivatives (WO0005234).

As specific example of phenylmethyl benzoquinone derivatives there may be mentioned benzoquinone derivative represented by the following general formula (1):

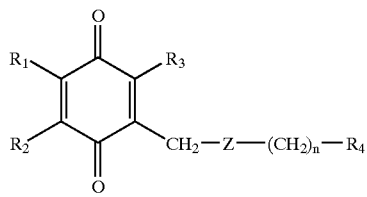 (I)

wherein

R$_1$, R$_2$, and R$_3$ are each independently a hydrogen atom, an alkyl group having 1 to 5 carbons, or an alkoxy group having 1 to 5 carbons;

R$_4$ is a hydrogen atom, a hydroxymethyl group, an alkyl group, or a carboxyl group which is optionally esterified or amidated;

Z is

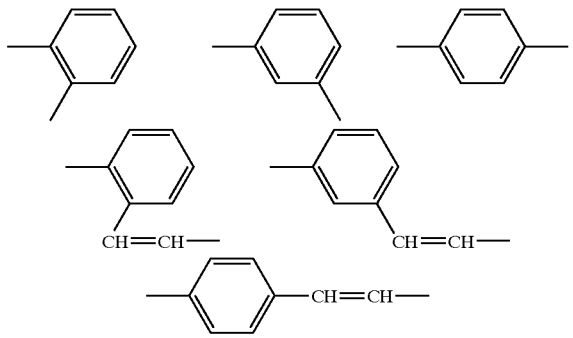

and, n is an integer from 0 to 6,
or its hydroquinone form, or a pharmaceutically acceptable salts thereof.

The hydroquinone form according to the invention refers to the compound that is formed by converting an oxo at position 1 and/or position 4 of the benzoquinone ring of the benzoquinone derivative according to the present invention to a hydroxy group chemically with a catalyst etc. or biochemically with an enzyme etc., or by converting with reduction in vivo, and that has an activity equivalent to that of the benzoquinone derivative.

As the pharmaceutically acceptable salt, there may be mentioned, for example, a salt with an inorganic acid such as hydrochloric acid, nitric acid, sulfuric acid, phosphoric acid, and hydrobromic acid, an organic acid such as maleic acid, fumaric acid, tartaric acid, lactic acid, citric acid, acetic acid, methanesulfonic acid, p-toluenesulfonic acid, adipic acid, palmitic acid, and tannic acid, an inorganic metal including an alkali metal such as lithium, sodium, and potassium, and an alkaline earth metal such as calcium, and magnesium, and a basic amino acid such as lysine, or a salt with an organic amine such as ammonium.

In the formula, R$_1$, R$_2$, and R$_3$ are each independently a hydrogen atom, an alkyl group having 1 to 5 carbons, or an alkoxy group having 1 to 5 carbons. Preferred examples of the alkyl group include straight or branched saturated aliphatic hydrocarbon groups having 1 to 5 carbons such as methyl, ethyl, propyl, isopropyl, butyl, isobutyl, sec-butyl, tert-butyl, pentyl, isopentyl, neopentyl, and tert-pentyl, saturated alicyclic hydrocarbon groups such as cyclopropyl, cyclobutyl, cyclopentyl, and cyclohexyl, saturated alicyclic hydrocarbon-aliphatic hydrocarbon groups such as cyclopropylmethyl, cyclopropylethyl, and cyclobutylmethyl, and the alkoxy groups include the oxy groups of the above. Preferred examples of R$_1$ and R$_2$ include a hydrogen atom, a methyl group, and a methoxy group, and those of R$_3$ include a hydrogen atom or a methyl group.

R$_4$ represents a hydrogen atom, a hydroxymethyl group, an alkyl group, or a carboxyl group which is optionally esterified or amidated, wherein preferred examples of the alkyl group include those mentioned above for R$_1$, R$_2$ and R$_3$, and preferred examples of the carboxyl group which is optionally esterified or amidated include: a group —COOR$_5$ wherein R$_5$ is a hydrogen atom, an optionally substituted alkyl group having 1 to 8 carbons, an optionally substituted phenyl group, or an optionally substituted aralkyl group having 7 to 11 carbons; a group —CONR$_6$R$_7$ wherein R$_6$ and R$^7$ are each independently a hydrogen atom, an optionally substituted alkyl group having 1 to 8 carbons, an optionally substituted bicyclic unsaturated or partially saturated hydrocarbon ring group having 9 to 11 carbons, an optionally substituted heterocyclic group, an optionally substituted phenyl group, an optionally substituted aralkyl group having 7 to 11 carbons, or a heteroaryl-C$_1$–C$_3$-alkyl group, or R$_6$ and R$_7$, together with the nitrogen atom to which they are attached, represent a heterocyclic group which may further contain a nitrogen, oxygen, and/or sulfur atom, and; a group —CONR$_6$R$_7$ wherein R$_6$ and R$_7$, together with the nitrogen atom to which they are attached, represent a 5- to 10-membered optionally substituted, nitrogen-containing heterocyclic group which may contain, in addition to the carbon and nitrogen atom, 1 to 3 heteroatoms selected from the group consisting of a nitrogen, oxygen, and sulfur atom, the carbon atom on said cyclic group being optionally a ketone form or the sulfur atom on said cyclic group being optionally an oxide form.

As specific examples of the alkyl group R$_5$ having 1 to 8 carbons, there may be mentioned a straight or branched saturated aliphatic hydrocarbon group having 1 to 8 carbons such as methyl, ethyl, propyl, isopropyl, butyl, isobutyl, sec-butyl, tert-butyl, 3-methylbutyl, pentyl, 1-ethylbutyl, isopentyl, neopentyl, tert-pentyl, 1,3-dimethylbutyl, 1-methylhexyl, 3,3-dimethylbutyl, 2-ethylbutyl, 2-methylpentyl, 3-methylpentyl, hexyl, heptyl, and 1-methylheptyl; a saturated alicyclic hydrocarbon group such as cyclopropyl, cyclobutyl, cyclopentyl, cyclohexyl, cycloheptyl, and cyclooctyl; and a saturated alicyclic hydrocarbon-aliphatic hydrocarbon group such as cyclopropylmethyl, cyclopropylethyl, cyclobutylmethyl, cyclopentylmethyl, cyclohexylmethyl, and cyclopentylmethyl, and the like. As specific examples of an aralkyl group having 7 to 11 carbons, there may be mentioned benzyl, phenethyl, 1-phenylethyl, 3-phenylpropyl, 4-phenylbutyl, 5-phenylpentyl, 1-naphthylmethyl, 2-naphthylmethyl and the like.

The alkyl, phenyl and aralkyl groups described above may be substituted, on the chain or the ring thereof, with one or two substituents or substituents comprising combinations of these substituents, said substituent being selected from, for example, a hydroxyl group; an aldehyde group; a carboxyl group; a carbamoyl group; an amino group; a nitrile group; a cyano group; a halogen atom such as a chlorine and fluorine atom; an alkyl group having preferably 1 to 6 carbons such as a methyl, ethyl, propyl and isopropyl group, or their halogenated or hydroxy-substituted group and alkoxy-alkyl group; an aryl group having preferably 6 to 10 carbons such as a phenyl and naphthyl group, or their halogenated group; an aralkyl group having preferably 7 to 11 carbons such as a benzyl, phenethyl and 3-phenylpropyl group; an alkyloxy group having preferably 1 to 6 carbons such as a methoxy, ethoxy, propyloxy and butyloxy group; a cyclic acetal group such as a methylenedioxy and ethylenedioxy group; an aralkyloxy having preferably 7 to 11 carbons such as a benzyloxy, phenethyloxy and 3-phenylpropyloxy group, and phenoxy group; an alkylcarbonyl group having preferably 2 to 6 carbons such as a methylcarbonyl, ethylcarbonyl and propylcarbonyl group; an arylcarbonyl group having preferably 7 to 11 carbons such as a benzoyl group; an alkyloxycarbonyl group having preferably 2 to 6 carbons such as a methoxycarbonyl, ethoxycarbonyl, propyloxycarbonyl and tert-butyloxycarbonyl group; an aralkyloxycarbonyl group having preferably 8 to 12 carbons such as a benzyloxycarbonyl, phenethyloxycarbonyl and 3-phenylpropyloxycarbonyl group, and phenoxycarbonyl group; an amino group substituted with one substituent or a combination of two substituents that are the same or different, said substituent being selected from an alkyl group having preferably 1 to 4 carbons such as a methyl, ethyl, propyl and isopropyl group, an aralkyl group having preferably 7 to 11 carbons such as a benzyl, phenethyl and 3-phenylpropyl group, phenyl group, an alkylcarbonyl group having preferably 2 to 6 carbons such as a methylcarbonyl, ethylcarbonyl and propylcarbonyl group, and an arylcarbonyl group having preferably 7 to 11 carbons such as a benzoyl group and the like; a 5- to 10-membered monocyclic or bicyclic unsaturated, partially or fully saturated heterocyclic ring containing 1 to 3 heteroatoms selected from the group consisting of a nitrogen, oxygen and sulfur atom, for example, pyrrole, furan, thiophene, pyran, indole, benzofuran, benzothiophene, benzopyran, pyrazole, isoxazole, isothiazole, indazole, benzoisoxazole, benzoisothiazole, imidazole, oxazole, thiazole, benzimidazole, benzoxazole, benzothiazole, pyridine, quinoline, isoquinoline, pyridazine, pyrimidine, pyrazine, cinnoline, phthalazine, quinazoline, quinoxaline, and a partially or fully saturated ring group thereof; a carbamoyl group having an amino group substituted with one substituent or a combination of two substituents that are the same or different, said substituent being selected from an alkyl group having preferably 1 to 4 carbons such as a methyl, ethyl, propyl and isopropyl group, an aralkyl group having preferably 7 to 11 carbons such as a benzyl, phenethyl and 3-phenylpropyl group, phenyl group, an alkylcarbonyl group having preferably 2 to 6 carbons such as a methylcarbonyl, ethylcarbonyl and propylcarbonyl group, and an arylcarbonyl group having preferably 7 to 11 carbons such as a benzoyl group, and the like, or a cyclic amino group such as a 5- to 8-membered heterocyclic ring optionally containing 1 to 3 heteroatoms selected from the group consisting of a nitrogen, oxygen and sulfur atom, for example, pyrrolidine, piperidine, morpholine, thiomorpholine, and piperazine; and the like.

As the optionally substituted alkyl groups having 1 to 8 carbons, the optionally. substituted phenyl group and the optionally substituted aralkyl group having 7 to 11 carbons of $R_6$ and $R_7$, those described for $R_5$ may be mentioned. As specific examples of the hydrocarbon ring of a bicyclic unsaturated or partially saturated hydrocarbon ring group having 9 to 11 carbons, there may be mentioned indene, indan, naphthalene, 1,2-dihydronaphthalene, 1,2,3,4-tetrahydronaphthalene and the like. As specific examples of the heterocyclic ring of a heterocyclic group, there may be mentioned a 5- to 10-membered monocyclic or bicyclic unsaturated, or partially or fully saturated heterocyclic ring containing 1 to 3 heteroatoms selected from the group consisting of a nitrogen, oxygen and sulfur atom, for example, pyrrole, furan, thiophene, pyran, indole, benzofuran, benzothiophene, benzopyran, pyrazole, isoxazole, isothiazole, indazole, benzoisoxazole, benzoisothiazole, imidazole, oxazole, thiazole, benzimidazole, benzoxazole, benzothiazole, pyridine, quinoline, isoquinoline, pyridazine, pyrimidine, pyrazine, cinnoline, phthalazine, quinazoline, quinoxaline, 1,2,3,4-tetrahydroquinoline, 1,2,3,4-tetrahydroisoquinoline, decahydroquinoline, and the like, as well as the partially or fully saturated ring thereof. Examples of a heteroaryl-$C_1$–$C_3$-alkyl group include, for example, a 2-pyridylmethyl, 3-pyridylmethyl, 4-pyridylmethyl, 2-pyrimidylmethyl, 2-imidazolylmethyl, 2-pyridylethyl, 3-pyridylethyl, 4-pyridylethyl, 1-(2-pyridyl)ethyl, 1-(3-pyridyl)ethyl, and 1-(4-pyridyl)ethyl group, and they may also be substituted on the chain or ring thereof with the same substituent to those described above for $R_5$.

As preferred examples of the heterocyclic group formed by $R_6$ and $R_7$ together with the nitrogen atom to which they are attached, which may further contain a nitrogen, oxygen and/or sulfur atom, or the 5- to 10-membered nitrogen-containing heterocyclic group formed by $R_6$ and $R_7$ together with the nitrogen atom to which they are attached, which may contain, in addition to a carbon and nitrogen atom, 1 to 3 heteroatoms selected from the group consisting of a nitrogen, oxygen and sulfur atom, there may be mentioned, for example, morpholino, thiomorpholino, pyrrolidino, piperidino, homopiperidino, piperazino, homopiperazino, and the like.

The carbon atom on the chain or the ring may be a ketone form, or the sulfur atom may be an oxide form, or the carbon atom or the nitrogen atom on the chain or the ring may be substituted with substituents as described for $R_5$.

Z is represented by

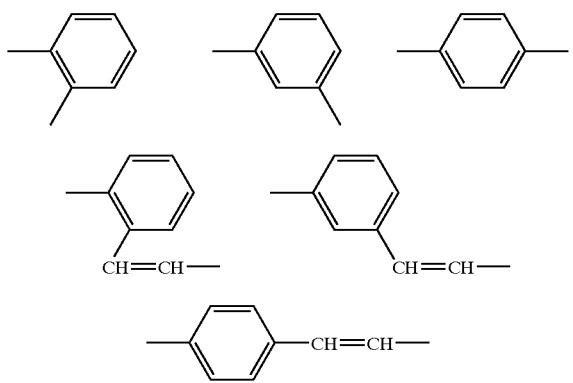

and n represents an integer from 0 to 6. In a preferred example, Z is

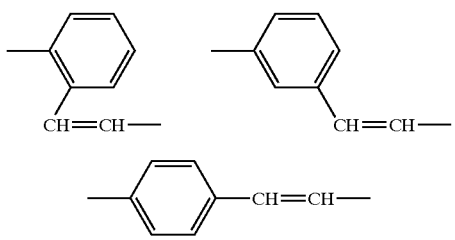

and n is an integer 0, or Z is

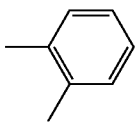 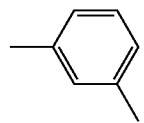 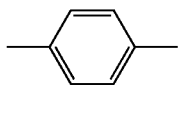

and n is a integer 1, 2 or 3.

Most preferably, $R_1$ and $R_2$ ate a methyl group or methoxy group; $R_3$ is a methyl group, $R_4$ is a carboxyl group which is optionally esterified or amidated; for example, the group-$CONR_6R_7$, and the 5- to 10-membered nitrogen-containing heterocyclic group formed by $R_6$ and $R_7$ together with the nitrogen atom to which they are attached, which may contain, in addition to a carbon and nitrogen atom, 1 to 3 heteroatoms selected from the group consisting of a nitrogen, oxygen and sulfur atom, specifically morpholino, thiomorpholino, pyrrolidino, piperidino, homopiperidino, piperazino, homopiperazino, or the $R_6$ and $R_7$ are each independently a hydrogen atom, an optionally substituted alkyl group having 1 to 8 carbons, specifically isopropylamino; Z is

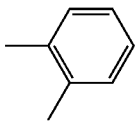 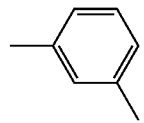 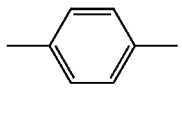

and n is an integer 0, 1, 2 or 3.

Preferred specific compounds include the following compounds:

N-[3-[4-(5,6-dimethoxy-3-methyl-1,4-benzoquinon-2-ylmethyl)phenyl]propionyl]morpholine,
  N-[3-[4-(5,6-dimethoxy-3-methyl-1,4-benzoquinon-2-ylmethyl)phenyl]propionyl]thiomorpholine,
  N-[3-[4-(5,6-dimethoxy-3-methyl-1,4-benzoquinon-2-ylmethyl)phenyl]propionyl]thiomorpholine S-oxide,
  N-[3-[4-(5,6-dimethoxy-3-methyl-1,4-benzoquinon-2-ylmethyl)phenyl]propionyl]thiomorpholine S-dioxide,
  N-[3-[4-(5,6-dimethoxy-3-methyl-1,4-benzoquinon-2-ylmethyl)phenyl]propionyl]piperidine,
  N-[3-[4-(5,6-dimethoxy-3-methyl-1,4-benzoquinon-2-ylmethyl)phenyl]propionyl]dimethylamine,
  N-[3-[4-(5,6-dimethoxy-3-methyl-1,4-benzoquinon-2-ylmethyl)phenyl]propionyl]isopropylamine,
  N-[3-[4-(5,6-dimethoxy-3-methyl-1,4-benzoquinon-2-ylmethyl)phenyl]propionyl]ethanolamine,
  N-[3-[4-(5,6-dimethoxy-3-methyl-1,4-benzoquinon-2-ylmethyl)phenyl]propionyl]benzylamine,
  N-[3-[4-(5,6-dimethoxy-3-methyl-1,4-benzoquinon-2-ylmethyl)phenyl]propionyl]phenethylamine,
  N-[3-[4-(5,6-dimethoxy-3-methyl-1,4-benzoquinon-2-ylmethyl)phenyl]acryloyl]morpholine,
  N-[3-[4-(5,6-dimethoxy-3-methyl-1,4-benzoquinon-2-ylmethyl)phenyl]acryloyl]thiomorpholine,
  N-[3-[4-(5,6-dimethoxy-3-methyl-1,4-benzoquinon-2-ylmethyl)phenyl]acryloyl]piperidine,
  N-[3-[4-(5,6-dimethoxy-3-methyl-1,4-benzoquinon-2-ylmethyl)phenyl]acryloyl]dimethylamine,
  N-[3-[4-(5,6-dimethoxy-3-methyl-1,4-benzoquinon-2-ylmethyl)phenyl]acryloyl]isopropylamine,
  N-[3-[4-(5,6-dimethoxy-3-methyl-1,4-benzoquinon-2-ylmethyl)phenyl]acryloyl]ethanolamine,
  N-[3-[4-(5,6-dimethoxy-3-methyl-1,4-benzoquinon-2-ylmethyl)phenyl]acryloyl]benzylamine,
  N-[3-[4-(5,6-dimethoxy-3-methyl-1,4-benzoquinon-2-ylmethyl)phenyl]acryloyl]phenethylamine,
  3-[4-(5,6-dimethoxy-3-methyl-1,4-benzoquinon-2-ylmethyl)phenyl]propionic acid,
  3-[4-(5,6-dimethoxy-3-methyl-1,4-benzoquinon-2-ylmethyl)phenyl]acrylic acid,
  2,3-dimethoxy-6-benzyl-5-methyl-1,4-benzoquinone,
  3-[4-(5,6-dimethoxy-3-methyl-1,4-benzoquinon-2-ylmethyl)phenyl]propanol,
  3-[3-(5,6-dimethoxy-3-methyl-1,4-benzoquinon-2-ylmethyl)phenyl]propionic acid,
  3-[3-(5,6-dimethoxy-3-methyl-1,4-benzoquinon-2-ylmethyl)phenyl]propionic acid ethylester,
  3-[3-(3,5,6-trimethyl-1,4-benzoquinon-2-ylmethyl)phenyl]acrylic acid,
  3-[3-(3,5,6-trimethyl-1,4-benzoquinon-2-ylmethyl)phenyl]propionic acid,
  3-[3-(3,5,6-trimethyl-1,4-benzoquinon-2-ylmethyl)phenyl]propionic acid ethylester,
  N-[3-[3-(3,5,6-trimethyl-1,4-benzoquinon-2-ylmethyl)phenyl]propionyl]morpholine,
  1-[3-[3-(3,5,6-trimethyl-1,4-benzoquinon-2-ylmethyl)phenyl]propionyl]-4-methylpiperazine,
  4-[3-(3,5,6-trimethyl-1,4-benzoquinon-2-ylmethyl)phenyl]-n-butyric acid,
  3-[3-(5,6-dimethoxy-3-methyl-1,4-benzoquinon-2-ylmethyl)phenyl]propionic acid,
  3-[4-(3,5,6-trimethyl-1,4-benzoquinon-2-ylmethyl)phenyl]acrylic acid,
  3-[4-(3,5,6-trimethyl-1,4-benzoquinon-2-ylmethyl)phenyl]acrylic acid ethylester,
  3-[4-(3,5,6-trimethyl-1,4-benzoquinon-2-ylmethyl)phenyl]propionic acid,
  4-[4-(3,5,6-trimethyl-1,4-benzoquinon-2-ylmethyl)phenyl]-n-butyric acid,
  N-[3-[3-(5,6-dimethoxy-3-methyl-1,4-benzoquinon-2-ylmethyl)phenyl]propionyl]piperidine,
  N-[3-[3-(5,6-dimethoxy-3-methyl-1,4-benzoquinon-2-ylmethyl)phenyl]propionyl]thiomorpholine,
  N-[3-[3-(5,6-dimethoxy-3-methyl-1,4-benzoquinon-2-ylmethyl)phenyl]propionyl]morpholine,
  N-[3-[3-(5,6-dimethoxy-3-methyl-1,4-benzoquinon-2-ylmethyl)phenyl]propionyl]isopropylamine,
  3-[3-(5,6-dimethoxy-3-methyl-1,4-benzoquinon-2-ylmethyl)phenyl]acrylic acid,
  N-[3-[3-(5,6-dimethoxy-3-methyl-1,4-benzoquinon-2-ylmethyl)phenyl]acryloyl]piperidine,
  N-[3-[3-(5,6-dimethoxy-3-methyl-1,4-benzoquinon-2-ylmethyl)phenyl]acryloyl]morpholine,
  N-[3-[3-(5,6-dimethoxy-3-methyl-1,4-benzoquinon-2-ylmethyl)phenyl]acryloyl]isopropylamine,
  N-[3-[3-(5,6-dimethoxy-3-methyl-1,4-benzoquinon-2-ylmethyl)phenyl]acryloyl]thiomorpholine,
  N-[3-[4-(3,5,6-trimethyl-1,4-benzoquinon-2-ylmethyl)phenyl]propionyl]isopropylamine,
  N-[3-[4-(3,5,6-trimethyl-1,4-benzoquinon-2-ylmethyl)phenyl]propionyl]piperidine,
  N-[3-[4-(3,5,6-trimethyl-1,4-benzoquinon-2-ylmethyl)phenyl]propionyl]morpholine, N-[3-[3-(3,5,6-trimethyl-1,4-benzoquinon-2-ylmethyl) phenyl]propionyl]isopropylamine,
N-[3-[3-(3,5,6-trimethyl-1,4-benzoquinon-2-ylmethyl) phenyl]propionyl]piperidine,
3-[2-(5,6-dimethoxy-3-methyl-1,4-benzoquinon-2-ylmethyl)phenyl]acrylic acid,
N-[3-[2-(5,6-dimethoxy-3-methyl-1,4-benzoquinon-2-ylmethyl)phenyl]acryloyl]thiomorpholine,
3-[2-(5,6-dimethoxy-3-methyl-1,4-benzoquinon-2-ylmethyl)phenyl]propionic acid,
N-[3-[2-(5,6-dimethoxy-3-methyl-1,4-benzoquinon-2-ylmethyl)phenyl]propionyl]piperidine,
N-[3-[2-(5,6-dimethoxy-3-methyl-1,4-benzoquinon-2-ylmethyl)phenyl]propionyl]morpholine,
N-[3-[2-(5,6-dimethoxy-3-methyl-1,4-benzoquinon-2-ylmethyl)phenyl]propionyl]thiomorpholine,
N-[3-[2-(5,6-dimethoxy-3-methyl-1,4-benzoquinon-2-ylmethyl)phenyl]propionyl]isopropylamine,
N-[3-[4-(5,6-dimethoxy-3-methyl-1,4-benzoquinon-2-ylmethyl)phenyl]propionyl]-(s)-2-(methoxymethyl) pyrrolidine,
N-[3-[4-(5,6-dimethoxy-3-methyl-1,4-benzoquinon-2-ylmethyl)phenyl]propionyl]isonipecotamide,
N-[3-[4-(5,6-dimethoxy-3-methyl-1,4-benzoquinon-2-ylmethyl)phenyl]propionyl]-4-methylpiperidine,
N-[3-[4-(5,6-dimethoxy-3-methyl-1,4-benzoquinon-2-ylmethyl)phenyl]propionyl]-2-methylpiperidine,
N-[3-[4-(5,6-dimethoxy-3-methyl-1,4-benzoquinon-2-ylmethyl)phenyl]propionyl]-3-methylpiperidine,
N-[3-[4-(5,6-dimethoxy-3-methyl-1,4-benzoquinon-2-ylmethyl)phenyl]propionyl]-4-methoxyaniline,
N-[3-[4-(5,6-dimethoxy-3-methyl-1,4-benzoquinon-2-ylmethyl)phenyl]propionyl]-2-hydroxyaniline,
N-[3-[4-(5,6-dimethoxy-3-methyl-1,4-benzoquinon-2-ylmethyl)phenyl]propionyl]-3,4-dimethoxyaniline,
N-[3-[4-(5,6-dimethoxy-3-methyl-1,4-benzoquinon-2-ylmethyl)phenyl]propionyl]-D,L-alaninol,
N-[3-[4-(5,6-dimethoxy-3-methyl-1,4-benzoquinon-2-ylmethyl)phenyl]propionyl]-D,L-pipecolic acid ethylester,
N-[3-[4-[5,6-dimethoxy-3-methyl-1,4-benzoquinon-2-ylmethyl)phenyl]propionyl]-L-prolinamide,
4-[3-[4-(5,6-dimethoxy-3-methyl-1,4-benzoquinon-2-ylmethyl)phenyl]propionyl]aminophenylacetonitrile,
N-[3-[4-(5,6-dimethoxy-3-methyl-1,4-benzoquinon-2-ylmethyl)phenyl]propionyl]-4-pentylaniline,
N-[3-[4-(5,6-dimethoxy-3-methyl-1,4-benzoquinon-2-ylmethyl)phenyl]propionyl]-(s)-(−)-1-phonylethylamine,
N-[3-[4-(5,6-dimethoxy-3-methyl-1,4-benzoquinon-2-ylmethyl)phenyl]propionyl]-(R)-(+)-1-phenylethylamine,
N-[3-[4-(5,6-dimethoxy-3-methyl-1,4-benzoquinon-2-ylmethyl)phenyl]propionyl]-1,3-dimethylbutylamine,
N-[3-[4-(5,6-dimethoxy-3-methyl-1,4-benzoquinon-2-ylmethyl)phenyl]propionyl]cycloheptylamine,
N-[3-[4-(5,6-dimethoxy-3-methyl-1,4-benzoquinon-2-ylmethyl)phenyl]propionyl]-3,5-dimethylpiperidine,
1-[3-[4-(5,6-dimethoxy-3-methyl-1,4-benzoquinon-2-ylmethyl)phenyl]propionyl]-4-ethoxycarbonylpiperazine,
1-[3-[4-(5,6-dimethoxy-3-methyl-1,4-benzoquinon-2-ylmethyl)phenyl]propionyl]-4-phenylpiperamine,
1-[3-[4-(5,6-dimethoxy-3-methyl-1,4-benzoquinon-2-ylmethyl)phenyl]propionyl]-4-hydroxy-4-phenylpiperidine,
1-[3-[4-(5,6-dimethoxy-3-methyl-1,4-benzoquinon-2-ylmethyl)phenyl]propionyl]-4-(4-chlorophenyl)-4-hydroxypiperidine,
1-[3-[4-(5,6-dimethoxy-3-methyl-1,4-benzoquinon-2-ylmethyl)phenyl]propionyl]-4-(2-methoxyphenyl) piperazine,
N-[3-[4-(5,6-dimethoxy-3-methyl-1,4-benzoquinon-2-ylmethyl)phenyl]propionyl]-6,7-dimethoxy-1,2,3,4-tetrahydroisoquinoline,
4-acetyl-4-phenyl-1-(3-[4-(5,6-dimethoxy-3-methyl-1,4-benzoquinon-2-ylmethyl)phenyl]propionyl]piperidine,
N-[3-[4-(5,6-dimethoxy-3-methyl-1,4-benzoquinon-2-ylmethyl)phenyl]propionyl]-1,2,3,4-tetrahydroisoquinoline,
N-[3-[4-(5,6-dimethoxy-3-methyl-1,4-benzoquinon-2-ylmethyl)phenyl]propionyl]isoamylamine, N-[3-[4-(5,6-dimethoxy-3-methyl-1,4-benzoquinon-2-ylmethyl) phenyl]propionyl]cyclohexylamine,
N-[3-[4-(5,6-dimethoxy-3-methyl-1,4-benzoquinon-2-ylmethyl)phenyl]propionyl]-4-hydroxyaniline,
4-(5,6-dimethoxy-3-methyl-1,4-benzoquinon-2-ylmethyl)benzoic acid,
N-[4-(5,6-dimethoxy-3-methyl-1,4-benzoquinon-2-ylmethyl)benzoyl]morpholine,
N-[4-(5,6-dimethoxy-3-methyl-1,4-benzoquinon-2-ylmethyl)benzoyl]isopropylamine,
N-[4-(5,6-dimethoxy-3-methyl-1,4-benzoquinon-2-ylmethyl)benzoyl]piperidine,
N-[4-(5,6-dimethoxy-3-methyl-1,4-benzoquinon-2-ylmethyl)benzoyl]thiomorpholine,
3-(5,6-dimethoxy-3-methyl-1,4-benzoquinon-2-ylmethyl)benzoic acid,
N-[3-(5,6-dimethoxy-3-methyl-1,4-benzoquinon-2-ylmethyl)benzoyl]isopropylamine,
N-[3-(5,6-dimethoxy-3-methyl-1,4-benzoquinon-2-ylmethyl)benzoyl]piperidine,
N-[3-(5,6-dimethoxy-3-methyl-1,4-benzoquinon-2-ylmethyl)benzoyl]morpholine,
N-[3-(5,6-dimethoxy-3-methyl-1,4-benzoquinon-2-ylmethyl)benzoyl]thiomorpholine,
4-[4-(5,6-dimethoxy-3-methyl-1,4-benzoquinon-2-ylmethyl)phenyl]-n-butyric acid,
N-[4-[4-(5,6-dimethoxy-3-methyl-1,4-benzoquinon-2-ylmethyl)phenyl]butanoyl]morpholine,
N-[4-[4-(5,6-dimethoxy-3-methyl-1,4-benzoquinon-2-ylmethyl)phenyl]butanoyl]thiomorpholine,
N-[4-[4-(5,6-dimethoxy-3-methyl-1,4-benzoquinon-2-ylmethyl)phenyl]butanoyl]piperidine,
N-[4-[4-(5,6-dimethoxy-3-methyl-1,4-benzoquinon-2-ylmethyl)phenyl]butanoyl]isopropylamine,
4-(5,6-dimethoxy-3-methyl-1,4-benzoquinon-2-ylmethyl)phenylacetic acid,
N-[4-(5,6-dimethoxy-3-methyl-1,4-benzoquinon-2-ylmethyl)phenylacetyl]morpholine,
N-[4-(5,6-dimethoxy-3-methyl-1,4-benzoquinon-2-ylmethyl)phenylacetyl]piperidine,
N-[4-(5,6-dimethoxy-3-methyl-1,4-benzoquinon-2-ylmethyl)phenylacetyl]thiomorpholine,
N-[4-(5,6-dimethoxy-3-methyl-1,4-benzoquinon-2-ylmethyl)phenylacetyl]isopropylamine, 3-(5,6-dimethoxy-3-methyl-1,4-benzoquinon-2-ylmethyl)phenylacetic acid, N-[3-(5,6-dimethoxy-3-methyl-1,4-benzoquinon-2-ylmethyl)phenylacetyl]piperidine, N-[3-(5,6-dimethoxy-3-methyl-1,4-benzoquinon-2-ylmethyl)phenylacetyl]thiomorpholine, N-[3-(5,6-dimethoxy-3-methyl-1,4-benzoquinon-2-ylmethyl)phenylacetyl]morpholine, N-[3-(5,6-dimethoxy-3-methyl-1,4-benzoquinon-2-ylmethyl)phenylacetyl]isopropylamine, 4-[3-(5,6-dimethoxy-3-methyl-1,4-benzoquinon-2-ylmethyl)phenyl]-n-butyric acid, N-[4-[3-(5,6-dimethoxy-3-methyl-1,4-benzoquinon-2-ylmethyl)phenyl]butanoyl]piperidine, N-[4-[3-(5,6-dimethoxy-3-methyl-1,4-benzoquinon-2-ylmethyl)phenyl]butanoyl]thiomorpholine, N-[4-[3-(5,6-dimethoxy-3-methyl-1,4-benzoquinon-2-ylmethyl)phenyl]butanoyl]morpholine, and N-[4-[3-(5,6-dimethoxy-3-methyl-1,4-benzoquinon-2-ylmethyl)phenyl]butanoyl]isopropylamine.

The benzoquinone derivative of the general formula (1) that is used as an active ingredient of the present invention may be prepared according to the method described in Japanese Unexamined Patent Publication (Kokai) No. 62(1987)-286949 or Chem. Pharm. Bull., 44(1): 139–144 (1996) or a method based thereupon.

Also, in the general formula (1) a benzoquinone derivative wherein $R_1$ and $R_2$ are a hydrogen atom, a methyl group or a methoxy group; $R_3$ is a hydrogen atom or a methyl group; $R_4$ is a carboxyl group which is optionally esterified or amidated; Z is

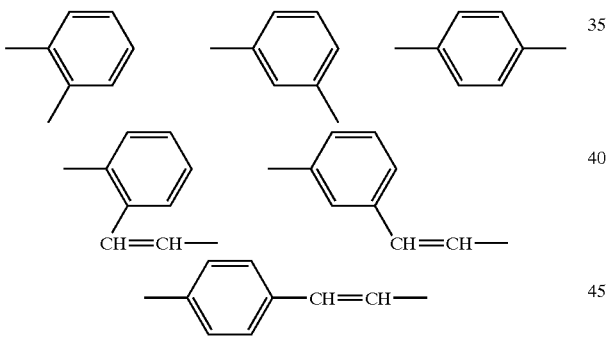

and, n is represented by an integer from 0 or 2, may also be prepared according to the following synthetic procedure.

Method 1

An aldehyde represented by the general formula (II):

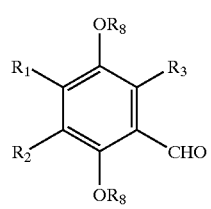

(II)

wherein $R_1$, $R_2$, and $R_3$ are as defined above, and $R_8$ represents an alkyl group having 1 to 5 carbons is allowed to react with a Grignard reagent of a halide represented by the general formula (III):

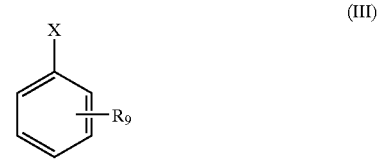

(III)

wherein X represents a bromine or a chlorine atom and $R_9$ represents a group:

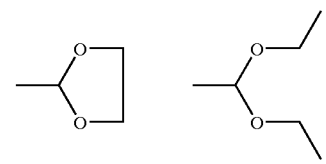

to obtain a compound represented by the general formula (IV):

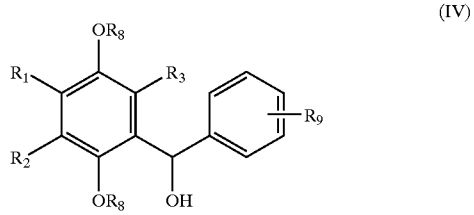

(IV)

wherein $R_1$, $R_2$, $R_3$, $R_8$ and $R_9$ are as defined above.

Compound (IV) is allowed to react with acetic anhydride in the presence of, for example, a base such as pyridine and 4-dimethylaminopyridine to prepare an acetylated compound, which is then subjected to a deacetal reaction in an acetone solution in the presence of an acid such as p-toluenesulfonic acid or camphorsulfonic acid to prepare an aldehyde represented by the general formula (V):

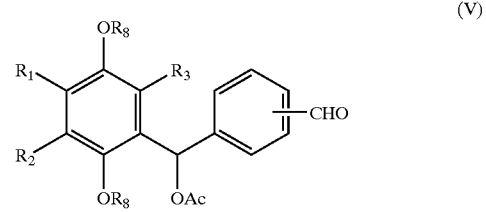

(V)

wherein $R_1$, $R_2$, $R_3$ and $R_8$ are as defined above. The aldehyde is allowed to react with a Wittig reagent of triethyl phosphonoacetate, which is further reduced with a reducing agent such as triethylsilane in the presence of an acidic catalyst such as trimethylsilyl trifluoromethanesulfonate (hereinafter referred to as TMSOTf) to yield a compound represented by the general formula (VI):

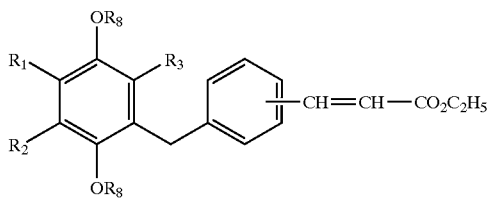

(VI)

wherein $R_1$, $R_2$, $R_3$ and $R_8$ are as defined above.

Compound (VI) is hydrolyzed or is further esterified or amidated in a conventional method to prepare a compound represented by the general formula (VII):

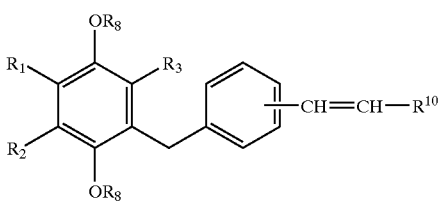

(VII)

wherein $R_1$, $R_2$, $R_3$ and $R_8$ are as defined above, and $R_{10}$ represents a carboxyl group which is optionally esterified or amidated.

The compound (VII) is then oxidized with ceric ammonium nitrate (hereinafter referred to as CAN) to yield the compound to be used as an active ingredient of the present invention represented by the general formula (Ia):

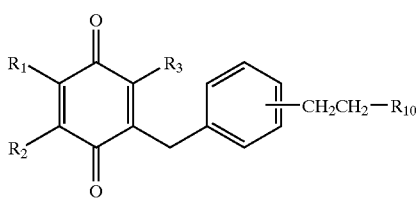

(Ia)

wherein $R_1$, $R^2$, $R_3$ and $R_{10}$ are as defined above. Using the compound of formula (Ia) wherein $R_{10}$ is a carboxyl group, an ester or an amide derivative may be obtained by a conventionally used esterification or amidation reaction, respectively.

Method 2

The compound represented by the general formula (VI) obtained in the above method is subjected to a catalytic hydrogenation and then is hydrolyzed or is further esterified or amidated in a conventional method to prepare a compound represented by the general formula (VIII):

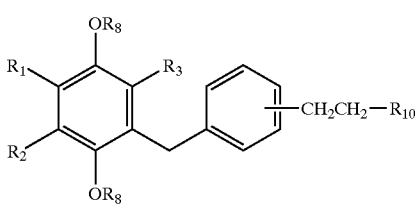

(VIII)

wherein $R_1$, $R_2$, $R_3$, $R_8$ and $R_{10}$ are as defined above.

Subsequently, compound (VIII) can be oxidized with CAN to yield the compound to be used asian active ingredient of the present invention represented by the general formula (Ib):

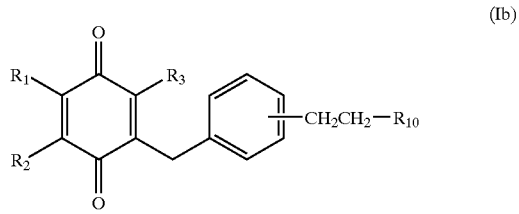

(Ib)

wherein $R_1$, $R_2$, $R_3$ and $R_{10}$ are as defined above.

The compound of formula (Ib) wherein $R_{10}$ is a carboxyl group may be converted to an ester or an amide derivative through a conventional procedure of esterification or amidation, respectively.

A benzoquinone derivative of the general formula (I) wherein $R_1$ and $R_2$ are a hydrogen atom, a methyl group or a methoxy group; $R_3$ is a hydrogen atom or a methyl group; $R_4$ is a carboxyl group which is optionally esterified or amidated; Z is

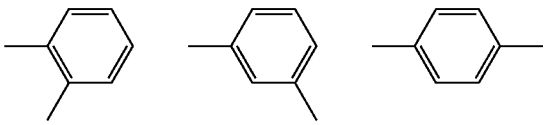

and n is an integer 0 may also be prepared by the following synthetic procedure.

Method 3

An aldehyde obtained in the above method represented by the general formula (V):

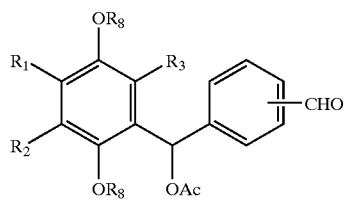

(V)

wherein $R^1$, $R_2$, $R_3$ and $R_8$ are as defined above, is oxidized using an oxidizing agent such as potassium permanganate, silver oxide, activated manganese dioxide and pyridinium dichromate, preferably silver oxide in an aqueous solution of sodium hydroxide to prepare a carboxylic acid represented by the general formula (IX):

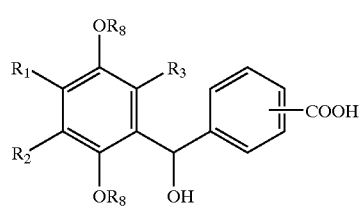

(IX)

wherein $R_1$, $R_2$, $R_3$ and $R_8$ are as defined above.

The carboxylic acid is reduced using a reducing agent such as triethylsilane in the presence of an acidic catalyst such as TMSOTf to yield a compound represented by the general formula (X):

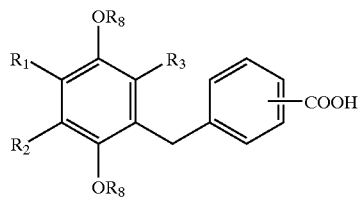

wherein $R_1$, $R_2$, $R_3$ and $R_8$ are as defined above. Compound (X) may be further esterified or amidated to prepare a compound represented by the general formula (XI):

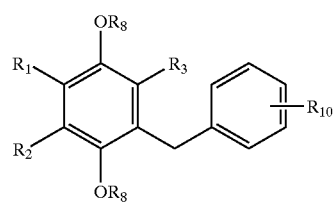

wherein $R_1$, $R_2$, $R_3$ and $R_8$ are as defined above, and $R_{10}$ is a carboxyl group which is optionally esterified or amidated.

Subsequently, compound (XI) can be oxidized with CAN to yield the compound to be used as an active ingredient of the present invention represented by the general formula (Ic):

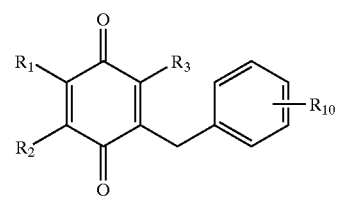

wherein $R_1$, $R_2$, $R_3$ and $R_{10}$ are as defined above. The compound of formula (Ic) wherein $R_{10}$ is a carboxyl group may be converted to an ester or an amide derivative through a conventional procedure of esterification or amidation, respectively.

Method 4

An aldehyde represented by the general formula (II):

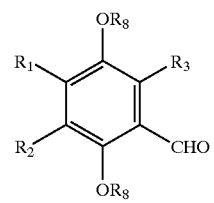

wherein $R_1$, $R_2$, $R_3$ and $R_8$ are as defined above, and an iodobenzoic acid ester represented by the general formula (XII):

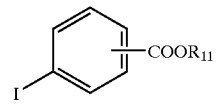

wherein $R_{11}$ represents an alkyl group such as a methyl group and an ethyl group, may be reacted in the presence of zinc chloride and an alkyllithium reagent such as methyllithium, n-butyllithium, or t-butyllithium to prepare an ester represented by the general formula (XIII):

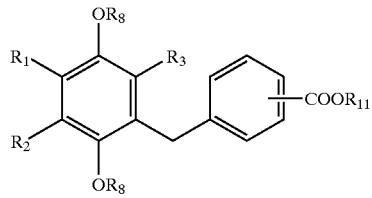

wherein $R_1$, $R_2$, $R_3$, $R_8$ and $R_{11}$ are as defined above.

The ester is reduced in a method similar to the one described above and then hydrolyzed or is further esterified or amidated in a conventionally used method to prepare a compound represented by the general formula (XI):

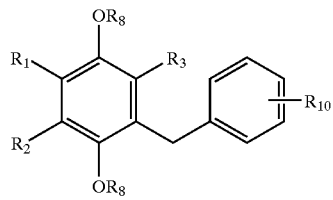

wherein $R_1$, $R_2$, $R^3$ and $R_8$ are as defined above, and $R_{10}$ is a carboxyl group which is optionally esterified or amidated.

Subsequently, compound (XI) can be oxidized with CAN to yield the compound to be used as an active ingredient of the present invention represented by the general formula (Ic):

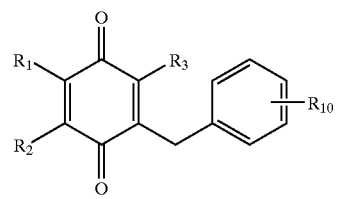

wherein $R_1$, $R_2$, $R_3$ and $R_{10}$ are as defined above. The compound of formula (Ic) wherein $R_{10}$ is a carboxyl group may be converted to an ester or an amide derivative through a conventional procedure of esterification or amidation, respectively.

A benzoquinone derivative of the general formula (I) wherein $R_1$ and $R_2$ are a hydrogen atom, a methyl or a methoxy group; $R_3$ is a hydrogen atom or a methyl group; $R_4$ is a carboxyl group which is optionally esterified or amidated; Z is

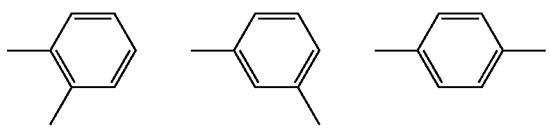

and n is an integer 1 or 3, may also be prepared by the, following synthetic procedure.

Method 5

A carboxylic acid obtained in the above method represented by the general formula (XIV):

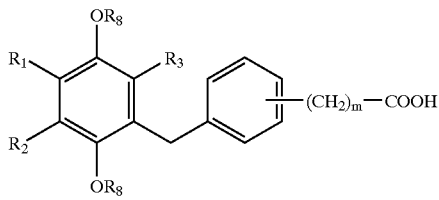

(XIV)

wherein $R_1$, $R_2$, $R_3$ and $R_8$ are as defined above and m is an integer 0 or 2, is reacted with oxalyl chloride or thionyl chloride to prepare an acid chloride, which is then reacted with an excess of diazomethane to convert to the corresponding diazomethyl ketone. The diazomethyl ketone can be then subjected to Wolff rearrangement reaction in the presence of silver oxide or a silver salt catalyst such as silver acetate to yield a carboxylic acid derivative represented by the general formula (XV):

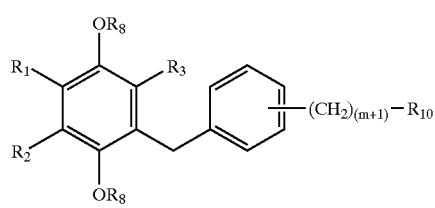

(XV)

wherein. $R_1$, $R_2$, $R_3$ and $R_8$ are as defined above and m is an integer 0 or 2, $R_{10}$ is a carboxyl group which is optionally esterified or amidated, said derivative having a carbon chain increased by one carbon. Through this rearrangement reaction, carboxylic acids, esters, and amides can be synthesized using water, alcohols, and amines as reaction solvent, respectively.

Subsequently, compound (XV) can be oxidized with CAN to yield the compound to be used as an active ingredient of the present invention represented by the general formula (Id):

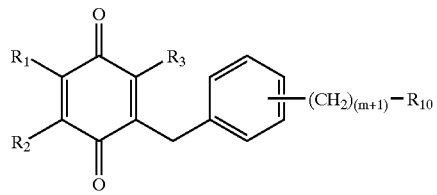

(Id)

wherein $R_1$, $R_2$, $R^3$, $R_{10}$ and m are as defined above. The compound of formula (Id) wherein $R_{10}$ is a carboxyl group may be converted to an ester or an amide derivative through a conventional procedure of esterification or amidation, respectively.

Method 6

In stead of the compound represented by the above general formula (XIV), a carboxylic acid represented by the general formula (XVI):

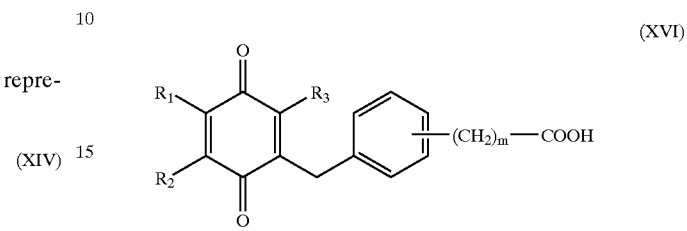

(XVI)

wherein $R_1$, $R_2$, $R_3$ and m are as defined above may be used as a starting material and treated as in Method 5 to produce a carboxylic acid derivative represented by the general formula (Id) having an increased number of carbon.

Using the above method 5 or 6, it is possible to prepare benzoquinone derivatives having a further extended methylene chain wherein m is represented by an integer 4, 5 or 6.

As specific example of indan derivatives there may be mentioned indan derivatives represented by the following the general formula (XVII):

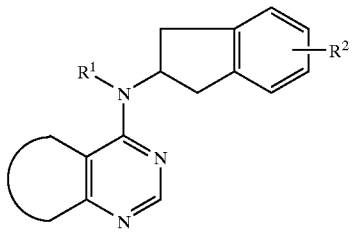

wherein
  $R^1$ represents a hydrogen atom or an alkyl group having 1 to 4 carbons, and
  $R^2$ represents a hydrogen atom,
  a —$OR^3$ group [in the group, $R^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)],
  a —$OCOR^4$ group [in the group, $R^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)],
  a —$COOR^5$ group [in the group, $R^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)), a —CONR$^6$R$^7$ group [in the group, R$^6$ and R$^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), or R$^6$ and R$^7$, together with the nitrogen atom to which they are attached, represent a heterocyclic group that may further contain a nitrogen atom, an oxygen atom, or a sulfur atom], or a —CH=CHR$^8$ group (in the group, R$^8$ represents an alkyl group having 1 to 4 carbons, or an optionally substituted phenyl group), and

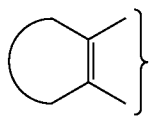

represents a skeleton selected from the group consisting of

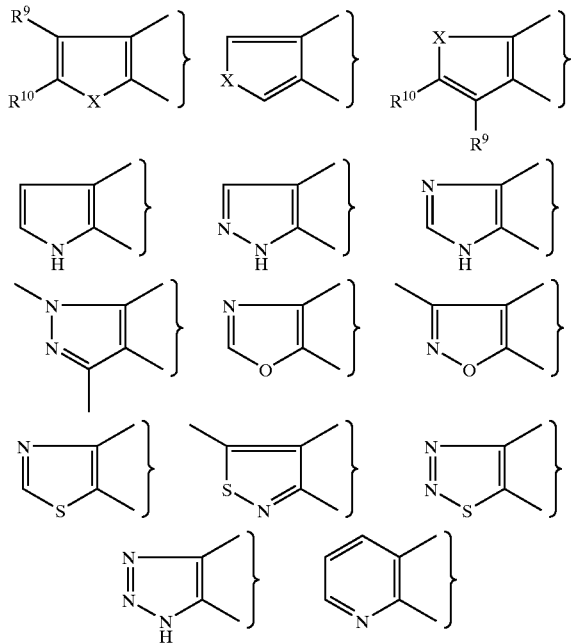

wherein R$^9$ and R$^{10}$, which may be the same or different, each represent a hydrogen atom, a halogen atom, a nitro group, a cyano group, a hydroxy group, an optionally substituted amino group, an optionally esterified or amidated carboxyl group, an alkyl group having 1 to 4 carbons, an alkyloxy group having 1 to 4 carbons, an optionally substituted phenyl group, an optionally substituted aralkyl group having 7 to 11 carbons, or an optionally substituted heterocyclic group, or R$^9$ and R$^{10}$ together form

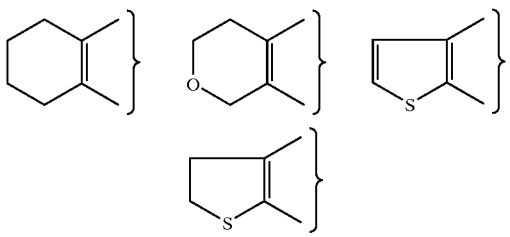

and X represents an oxygen atom or a sulfur atom;
or a pharmaceutically acceptable salt thereof.

As pharmaceutically acceptable salts, there may be mentioned, for example, a salt with an inorganic acid such as hydrochloric acid, nitric acid, sulfuric acid, phosphoric acid and hydrobromic acid, an organic acid such as maleic acid, fumaric acid, tartaric acid, lactic acid, citric acid, acetic acid, methanesulfonic acid, p-toluene sulfonic acid, adipic acid, palmitic acid and tannic acid, an inorganic metal including an alkaline metal such as lithium, sodium and potassium, and an alkaline earth metal such as calcium and magnesium, and a basic amino acid such as lysine, or a salt with an organic amine such as ammonium.

In the formula, R$^1$ represents a hydrogen atom or an alkyl group having 1 to 4 carbons. Preferred examples of the alkyl group include straight or branched saturated aliphatic hydrocarbon groups having 1 to 4 carbons such as methyl, ethyl, propyl, isopropyl, butyl, isobutyl, sec-butyl, tert-butyl, and saturated alicyclic hydrocarbon groups such as cyclopropyl and cyclobutyl, and a cyclopropyl methyl group. Preferred examples are those in which R$^1$ is a hydrogen atom, a methyl group, or an ethyl group.

As R$^2$, there can be mentioned a hydrogen atom, a —OR$^3$ group [in the group, R$^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)], a —OCOR$^4$ group [in the group, R$^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)], a —COOR$^5$ group [in the group, R$^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group)], a —CONR$^6$R$^7$ group tin the group, R$^6$ and R$^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —(CH$_2$)n A group (n is 0, or an integer of 1, 2 or 3, and A is a heterocyclic group), or R$^6$ and R$^7$, together with the nitrogen atom to which they are attached, represent a heterocyclic group that may further contain a nitrogen atom, an oxygen atom or a sulfur atom], or a —CH=CHR$^8$ group (in the group, R$^8$ represents an alkyl group having 1 to 4 carbons, or an optionally substituted phenyl group).

Specifically, as R$^3$, R$^4$, R$^5$, R$^6$ and R$^7$ that are alkyl groups having 1 to 7 carbons, there can be mentioned straight or branched saturated aliphatic hydrocarbon groups having 1 to 7 carbons such as methyl, ethyl, propyl, isopropyl, butyl, isobutyl, sec-butyl, tert-butyl, pentyl, isopentyl, neopentyl, tert-pentyl, hexyl, 3,3-dimethylbutyl, 2-ethylbutyl, 2-methylpentyl, 3-methylpentyl, 4-methylpentyl and heptyl; saturated alicyclic hydrocarbon groups such as cyclopropyl, cyclobutyl, cyclopentyl, cyclohexyl and cycloheptyl; and saturated alicyclic hydrocarbon-aliphatic hydrocarbon groups such as cyclopropylmethyl, cyclopropylethyl, cyclobutylmethyl, cyclopentylmethyl and cyclohexylmethyl, and the like.

As a bicyclic unsaturated or partially saturated hydrocarbon ring group having 9 to 11 carbons, there can be mentioned indene, indan, naphthalene, 1,2-dihydronaphthalene, 1,2,3,4-tetrahydronaphthalene, and the like.

As an aralkyl group having 7 to 11 carbons, there can be mentioned benzyl, phenethyl, 1-phenylethyl, 3-phenylpropyl, 4-phenylbutyl, 5-phenylpentyl, 1-naphthylmethyl, 2-naphthylmethyl, and the like.

A phenyl group, a bicyclic unsaturated or partially saturated hydrocarbon ring group having 9 to 11 carbons, and an aralkyl group having 7 to 11 carbons may be substituted on the ring with one to two substituents selected from:

a hydroxyl group;

a carboxyl group;

an amino group;

a halogen atom such a chlorine atom and a fluorine atom;

an alkyl group preferably having 1 to 4 carbons such as a methyl group, an ethyl group and a propyl group;

an aralkyl group preferably having 7 to 11 carbons such as a benzyl group, a phenethyl group and a 3-phenylpropyl group, and a phenyl group;

an alkyloxy group preferably having 1 to 4 carbons such as a methoxy group, an ethoxy group and a propyloxy group;

an aralkyloxy group preferably having 7 to 11 carbons such as a benzyloxy group, a phenethyloxy group, and a 3-phenylpropyloxy group, and a phenoxy group;

an alkyloxycarbonyl group preferably having 2 to 5 carbons such as a methoxycarbonyl group, an ethoxycarbonyl group and a propyloxycarbonyl group;

an aralkyloxycarbonyl group preferably having 8 to 12 carbons such as a benzyloxycarbonyl group, a phenethyloxycarbonyl group and a 3-phenylpropyloxycarbonyl group, and a phenoxycarbonyl group;

an amino group substituted with one substituent or a combination of two same or different substituents selected from an alkyl group preferably having 1 to 4 carbons such as a methyl group, an ethyl group and a propyl group, an aralkyl group preferably having 7 to 11 carbons such as a benzyl group, a phenethyl group and a 3-phenylpropyl group, and a phenyl group; or a carbamoyl group having an amino group substituted with one substituent or a combination of two same or different substituents selected from an alkyl group preferably having 1 to 4 carbons such as a methyl group, an ethyl group and a propyl group, an aralkyl group preferably having 7 to 11 carbons such as a benzyl group, a phenethyl group and a 3-phenylpropyl group, and a phenyl group, or a cyclic amino group such as a 5- to 8-membered heterocyclic group that may contain 1 to 3 heteroatoms selected from a nitrogen atom, an oxygen atom and a sulfur atom, for example, a group of pyrrolidine, piperidine, morpholine, thiomorpholine and piperazine.

As a heterocyclic group represented by A, there can be mentioned a 5 to 10-membered monocyclic or bicyclic unsaturated, partially saturated or a fully saturated heterocyclic group having 1 to 3 heteroatoms selected from a nitrogen atom, an oxygen atom and a sulfur atom, for example, a group of pyrrole, furan, thiophene, pyran, indole, benzofuran, benzothiophene, benzopyran, pyrazole, isoxazole, isothiazole, indazole, benzisoxazole, benzisothiazole, imidazole, oxazole, thiazole, benzimidazole, benzoxazole, benzothiazole, pyridine, quinoline, isoquinoline, pyridazine, pyrimidine, pirazine, cinnoline, phthalazine, quinazoline, quinoxaline, and a partially or fully saturated ring thereof.

As preferred examples of a heterocyclic group formed from R$^6$ and R$^7$, together with the nitrogen atom to which they are attached, and which may further contain a nitrogen atom, an oxygen atom or a sulfur atom, there can be mentioned a 5- to 8-membered heterocyclic group, for example, a group of pyrrolidine, piperidine, morpholine, thiomorpholine, homopiperidine, piperazine and homopiperazine.

As R$^8$ that is an alkyl group having 1 to 4 carbons and a substituent of an optionally substituted phenyl group, there can be mentioned one described above for R$^3$, R$^4$, R$^5$, R$^6$ and R$^7$.

As

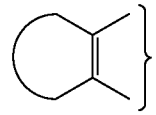

there can be mentioned

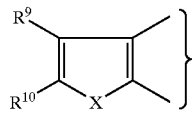 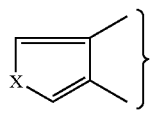

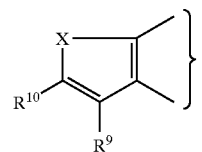 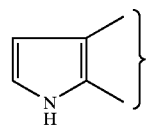 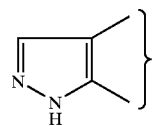

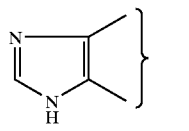 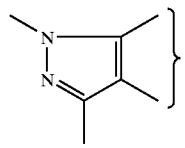

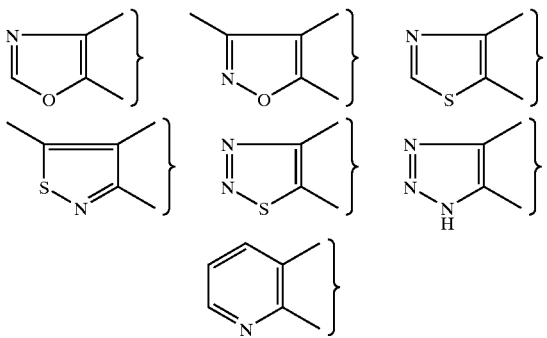

wherein $R^9$ and $R^{10}$, which may be the same or different, each represent a hydrogen atom, a halogen atom, a nitro group, a cyano group, a hydroxy group, an optionally substituted amino group, an optionally esterified or amidated carboxyl group, an alkyl group having 1 to 4 carbons, an alkyloxy group having 1 to 4 carbons, an optionally substituted phenyl group, an optionally substituted aralkyl group having 7 to 11 carbons, or an optionally substituted heterocyclic group, or $R^9$ and $R^{10}$ together form

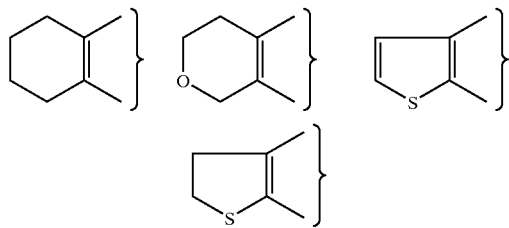

and X represents an oxygen atom or a sulfur atom.

As $R^9$ and $R^{10}$ that are a halogen atom, there can be mentioned a fluorine atom, a chlorine atom, a bromine atom, and the like.

As an optionally substituted amino group, in addition to a non-substituted amino group, there can be mentioned an amino group substituted with one substituent or a combination of two same or different substituents selected from an alkyl group preferably having 1 to 4 carbons such as a methyl group, an ethyl group and a propyl group, an aralkyl group preferably having 7 to 11 carbons such as a benzyl group, and a phenyl group, or a cyclic amino group such as a 5- to 8-membered heterocyclic group that may contain 1 to 3 heteroatoms selected from a nitrogen atom, an oxygen atom and a sulfur atom, for example, a group of pyrrolidine, piperidine, morpholine, thiomorpholine and piperazine, and the like.

As an optionally esterified or amidated carboxyl group, in addition to the carboxyl group, there can be mentioned an alkyloxy carbonyl group preferably having 2 to 5 carbons such as a methoxycarbonyl group, a ethoxycarbonyl group and a propyloxycarbonyl group, an aralkyloxycarbonyl group preferably having 8 to 12 carbons such as a benzyloxycarbonyl group, and a phenoxycarbonyl group; a carbamoyl group having, an amino group, an amino group substituted with a substituent or a combination of two same or different substituents selected from an alkyl group preferably having 1 to 4 carbons such as a methyl group, an ethyl group and a propyl group, and an aralkyl group preferably having 7 to 11 carbons such as a benzyl group and a phenyl group, or an cyclic amino group such as a 5- to 8-membered heterocyclic group that may contain 1 to 3 heteroatoms selected from a nitrogen atom, an oxygen atom and a sulfur atom, for example, a group of pyrrolidine, piperidine, morpholine, thiomorpholine and piperazine.

As an alkyl group having 1 to 4 carbons, there can be mentioned one described above for $R^1$.

As an alkyloxy group having 1 to 4 carbons, there can be mentioned a methoxy group, an ethoxy group, a propyloxy group, an isopropyloxy group, a butyloxy group, and the like.

As an optionally substituted phenyl group and an optionally substituted aralkyl group having 7 to 11 carbons, there can be mentioned one described above for $R^3$, $R^4$, $R^5$, $R^6$ and $R^7$.

As an optionally substituted heterocyclic group, there can be mentioned one described above for A, which may further contain, on the ring, a substituent such as a halogen atom, an alkyl group having 1 to 4 carbons, and an alkyloxy group having 1 to 4 carbons described above for $R^9$ and $R^{10}$, for example furan, thiophene and 3-methylpyridine, and the like.

As preferred indan derivative compounds there may be mentioned indan derivatives in which $R^2$ represents a hydrogen atom or a pharmaceutically acceptable salt thereof.

There may be also mentioned the indan derivatives in which $R^2$ represents a —$OR^3$ group [in the group, $R^3$ represents a hydrogen atom, an alkyl group having 1 to 7 carbons, an optionally substituted phenyl group, an optionally substituted bicyclic unsaturated or partially saturated hydrocarbon ring group having 9 to 11 carbons, is an optionally substituted arcalkyl group having 7 to 11 carbons, or a —$(CH_2)n$ A group (n is 0, or an integer of 1, 2 or 3, and A is a heterocyclic group)], or a pharmaceutically acceptable salt thereof.

There may further be mentioned the indan derivatives in which $R^2$ represents a —$OCOR^4$ group [in the group, $R^4$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], or a pharmaceutically acceptable salt thereof.

There may still further be mentioned the indan derivatives in which $R^2$ represents a —$COOR^9$ group [in the group, $R^5$ represents a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group)], or a pharmaceutically acceptable salt thereof.

There may still further be mentioned the indan derivatives in which $R^2$ represents a —$CONR^6R^7$ group [in the group, $R^6$ and $R^7$, which may be the same or different, each represent a hydrogen atom, an alkyl group having 1 to 7 carbons, an optionally substituted phenyl group, an optionally substituted bicyclic unsaturated or partially saturated hydrocarbon ring group having 9 to 11 carbons, an optionally substituted aralkyl group having 7 to 11 carbons, or a —$(CH_2)n$ A group (n is 0, or an integer of 1, 2 or 3, and A is a heterocyclic group), or $R^6$ and $R^7$, together with the nitrogen atom to which they are attached, represent a heterocyclic group that may further contain a nitrogen atom, an oxygen atom or a sulfur atom], or a pharmaceutically acceptable salt thereof.

There may still further be mentioned the indan derivatives in which $R^2$ represents a —CH=CHR$^8$ group [in the group, $R^8$ represents an alkyl group having 1 to 4 carbons, or an optionally substituted phenyl group), or a pharmaceutically acceptable salt thereof.

As specific compounds that are particularly preferred there may be mentioned the following:

4-(2-indanylamino)-5-methylthieno[2,3-d]pyrimidine;
4-(2-indanylamino)thieno[3,4-d]pyrimidine;
4-(2-indanylamino)-7-methylthieno[3,2-d]pyrimidine;
4-(2-indanylamino)pyrrolo[2,3-d]pyrimidine;
4-(2-indanylamino)thieno[2,3-d]pyrimidine;
4-(2-indanylamino)furo[2,3-d]pyrimidine;
4-(2-indanylamino)pyrazolo[3,4-d]pyrimidine;
7-(2-indanylamino)-v-triazolo[4,5-d]pyrimidine;
7-(2-indanylamino)oxazolo[5,4-d]pyrimidine;
3-methyl-4-(2-indanylamino)isoxazolo[5,4-d]pyrimidine;
7-(2-indanylamino)thiazolo(5,4-d]pyrimidine;
2-(2-indanylamino)-1-thia-2,3,5,7-tetraazaindene;
6-(2-indanylamino)-7-methylisothiazolo[3,4-d]pyrimidine;
7-(2-indanylamino)-1,3-dimethyl-1H-pyrazolo[4,3-d]pyrimidine;
4-(2-indanylamino)pyrido[2,3-d]pyrimidine;
4-[N-(2-indanyl)-N-methylamino]-5-methylthieno[2,3-d]pyrimidine;
4-(2-indanylamino)-5-phenylthieno[2,3-d]pyrimidine;
4-(2-indanylamino)-5-(2-thienyl)thieno[2,3-d]pyrimidine;
5-(2-furyl)-4-(2-indanylamino)thieno[2,3-d]pyrimidine;
4-(2-indanylamino)-5,6-dimethylthieno[2,3-d]pyrimidine;
4-(2-indanylamino)-5-[6-(3-methylpyridyl)]thieno[2,3-d]pyrimidine;
4-(2-indanylamino)-5-isopropylthieno[2,3-d]pyrimidine;
4-(5-methoxyindan-2-yl)amino-5-methylthieno[2,3-d]pyrimidine;
4-(5-hydroxyindan-2-yl)amino-5-methylthieno[2,3-d]pyrimidine;
4-(5-phenoxyindan-2-yl)amino-5-methylthieno[2,3-d]pyrimidine 4-[5-((E)-2-(4-methylphenyl)ethanyl]indan-2-yl]amino-5-methylthieno[2,3-d]pyrimidine;
4-(5-methoxycarbonylindan-2-yl)amino-5-methylthieno[2,3-d]pyrimidine;
4-(5-carboxyindan-2-yl)amino-5-methylthieno[2,3-d]pyrimidine sodium salt;
N-propyl-2-(5-methylthieno[2,3-d]pyrimidine-4-yl)amino-5-indancarboxamide;
N-phenyl-2-(5-methylthieno[2,3-d]pyrimidine-4-yl)amino-5-indancarboxamide;
N-benzyl-2-(5-methylthieno[2,3-d]pyrimidine-4-yl)amino-5-indancarboxamide;
2-[5-methylthieno[2,3-d]pyrimidine-4-yl]aminoindan-5-carboxylic acid morpholinamide;
4-(4-methoxyindan-2-yl)amino-5-methylthieno[2,3-d]pyrimidine;
4-(4-methoxycarbonylindan-2-yl)amino-5-methylthieno[2,3-d]pyrimidine;
4-(5-acetoxyindan-2-yl)amino-5-methylthieno[2-[3-d]pyrimidine;
4-(5-benzoyloxyindan-2-yl)amino-5-methylthieno[2,3-d]pyrimidine;
6-(2-indanylamino)purine; and
4-(2-indanylamino)thieno[3,2-d]pyrimidine.

An indan derivative represented by the general formula (I) that is used as an active ingredient of the present invention may be prepared by methods described in, for example, Japanese Unexamined Patent Publication (Kokai) No. 5-310743, Japanese Unexamined Patent Publication (Kokai) No. 5-310748, J. Am Chem. Soc., 76, 6073 (1954), J. Am. Chem. Soc., 78,784 (1956), J. Am. Chem. Soc., 88,3829 (1966), J. Org. Chem., 26,4961 (1961), J. Org. Chem., 29,2116 (1964), Chem. Pharm. Bull., 16,750 (1968), J. Chem. Soc.(C), 1856 (1967), Angew. Chem., internat. Edit., 6,83 (1967), Arch. Pharm. Ber. Dtsch. Pharm. Ges., 301,611 (1968), J. Med. Chem., 31,454 (1988), J. Heterocyclic Chem., 30,509 (1993), and the like, and methods based on these.

Method 1

An indan derivative represented by the general formula (I) may be prepared by a method shown, for example, in Scheme 1.

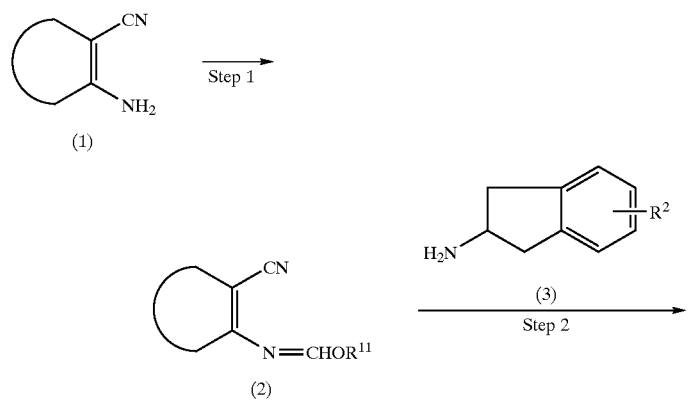

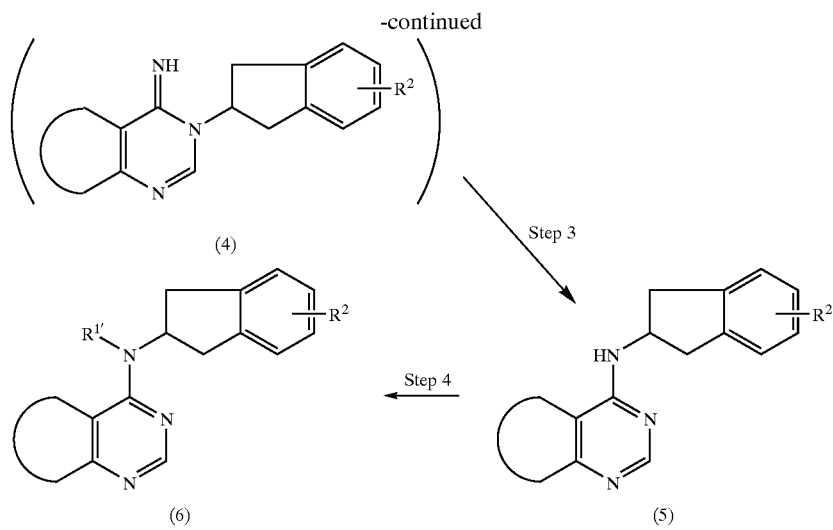

(4)

Step 3

(6) Step 4 (5)

First, aminonitrile (1) is condensed with an orthoester such as trimethyl orthoformate or triethyl orthoformate to yield an iminoether (2) ($R^{11}$ represents an alkyl group having 1 to 4 carbons, preferably methyl or ethyl) (step 1). In some instances, this reaction is conducted in the presence of acetic anhydride. Reaction of the iminoether (2) ($R^{11}$ represents an alkyl group having 1 to 4 carbons, preferably methyl or ethyl) with an aminoindan derivative represented by formula (3) ($R^2$ has the same meaning as the general formula (XVII)) or a salt thereof under a basic condition gives, via an imine product (4), an indan derivative represented by formula (5) ($R^2$ has the same meaning as the general formula (XVII)) by Dimroth rearrangement. The reaction temperature is preferably 80° C. to 140° C.

It is also possible to prepare an indan derivative represented by formula (5) ($R^2$ has the same meaning as the general formula (XVII)), without isolating the iminoether (2), by carrying out the following step 2 and step 3 in the absence of solvents.

By alkylating the amino group of the indan derivative represented by formula (5) ($R^2$ has the same meaning as the general formula (XVII)) thus obtained, an indan derivative represented by formula (6) ($R^1$ represents an alkyl group having 1 to 4 carbons and $R^2$ has the same meaning as the general formula (XVII)) can be prepared (step 4). As a method of alkylation, there can be applied a nucleophilic displacement reaction of a halogenated alkyl, an alkylsulfonate ester and an alkysulfate, or a reductive alkylation in which the corresponding aldehyde or ketone is reacted in the presence of a reducing agent such as sodium borohydride or sodium cyanoborohydride.

Method 2

The indan derivative of formula (5) ($R^2$ has the same meaning as the general formula (XVII)) may also be synthesized by the method shown in Scheme 2.

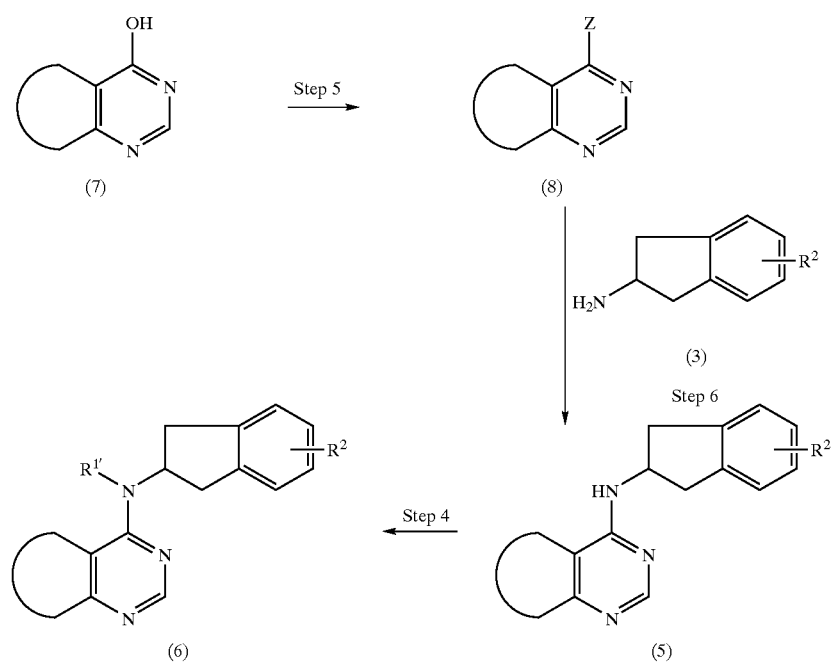

First, a 4-substituted pyrimidine derivative represented by formula (8) (in the formula, Z represents a leaving group, preferably a chlorine atom or a methylthio group) is synthesized from a 4-hydroxypyrimidine derivative represented by formula (7) (step 5). For example, the compound represented by formula (8) in which Z is a chlorine atom can be synthesized by heating formula (7) with phosphorus oxychloride or thionyl chloride in the presence or absence of a base such as diethyl aniline. The compound represented by formula (8) in which Z is a methylthio group can also be synthesized by reacting formula (7) with diphosphorus pentasulfide, followed by methyl iodide in the presence of a base such as sodium hydroxide.

Formula (8) (in the formula, Z represents a leaving group, preferably a chlorine atom or a methylthio group) thus obtained is aminated with an aminoindan derivative represented by formula (3) ($R^2$ has the same meaning as the general formula (XVII)) or a salt thereof in the presence or absence of a base such as triethylamine at a reaction temperature of room temperature to 180° C. to yield an indan derivative of formula (5) ($R^2$ has the same meaning as the general formula (XVII)) (step 6). The reaction is carried out in the absence of a solvent or preferably in a non-reactive solvent such as ethanol.

The alkylation of the amino group of the indan derivative represented by formula (5) ($R^2$ has the same meaning as the general formula (XVII)) thus obtained may be conducted by the method described above (step 4).

The aminoindan derivative (3) to be used as a starting material for synthesis of the compounds of interest by these methods can be prepared in the following synthetic method according to and based on the methods described in Japanese Unexamined Patent Publication (Kokai) No. 63-23853, J. Med. Chem., 25,1142 (1982), J. Med. Chem., 33,703 (1990), Synthesis, 285 (1995), Chem. Rev., 95,2457 (1995), J. Org. Chem., -58,2201 (1993), Synthesis, 47-(1989), J. Am Chem. Soc., 90,5616 (1968), J. Am Chem. Soc., 119,7974 (1997), Jikken Kagaku Koza (Experimental Chemistry Series), Vol. 20, Fourth edition, page 187 (1992, Maruzen K. K.), Jikken Kagaku Koza (Experimental Chemistry Series), Vol. 22, Fourth edition, pages 3, 43, and 137 (1992, Maruzen K. K.), and Jikken Kagaku Koza (Experimental Chemistry Series), Vol. 23, Fourth edition, page 7 (1992, Maruzen K. K.).

The α position of the carbonyl group of a ketone derivative represented by the general formula (9):

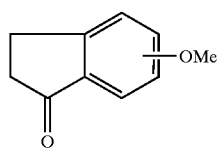

(9)

is converted to an oxime using a nitrite ester such as isoamyl nitrite, butyl nitrite and ethyl nitrite, in the presence of an acid catalyst such as hydrochloric acid in a non-reactive solvent such as diethyl ether, ethanol, methanol, tetrahydrofuran, benzene and methylene chloride at room temperature to 60° C. Preferably the reaction is conducted using isoamyl nitrite or hydrochloric acid in methanol at 40° C.

The oxime derivative of the general formula (10) thus obtained:

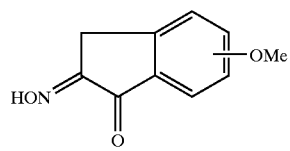

(10)

is subjected to catalytic hydrogenation in acetic acid by adding sulfuric acid or perchloric acid in the presence or absence of palladium chloride with palladium carbon as a catalyst at ordinary pressure or an atmosphere of pressurized hydrogen at a temperature of room temperature to 60° C. to yield an amine derivative of the general formula (11):

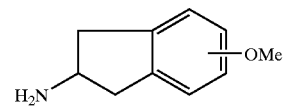

(11)

The amine derivative (11) is then subjected to a demethylation reaction at room temperature or under heating, using boron tribromide, boron trichloride, hydroiodic acid, hydrobromic acid and the like, preferably by heating to reflux, using hydrobromic acid in acetic acid to produce a compound represented by the general formula (12):

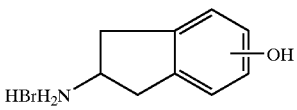

(12)

A compound represented by the general formula (13):

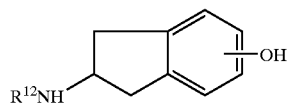

(13)

(wherein $R^{12}$ is a protecting group of an amino group, preferably a tert-butoxycarbonyl group or a benzyloxycarbonyl group) can be synthesized by an introduction reaction of a protecting group into the amino group of compound (12), the method described in Peputido Goseino Kisoto Jikken (The Basic and Experimental Peptide Synthesis), Nobuo Izumiya, Tetsuo Kato, Haruhiko Aoyagi, Michinori Waki, (1985, Maruzen K. K.).

A compound represented by the general formula (14):

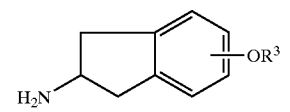

(14)

(wherein $R^3$ has the same meaning as the above) is obtained by etherification and deprotection of the amino protecting group of compound (13). Etherification can be carried out according to the method such as is described in Jikken Kagaku Koza (Experimental Chemistry Series), Vol. 20, Fourth edition, page 187 (1992, Maruzen K. K.). The deprotection reaction of the amino protecting group can also be carried out by a conventionally used method such as the method described in Peputido Goseino Kisoto Jikken (The Basic and Experimental Peptide Synthesis), Nobuo Izumiya, Tetsuo Kato, Haruhiko Aoyagi, Michinori Waki, (1985, Maruzen K. K.), and preferably it is a deprotection reaction by acid or catalytic hydrogenation. When an acid is used in the deprotection reaction, the ether derivative (14) can be prepared as a salt with the acid used.

A ester derivative represented by the general formula (15):

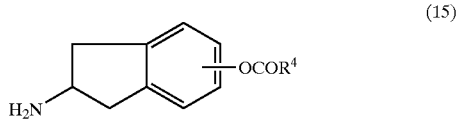

(15)

(wherein $R^4$ has the same meaning as the above) can be obtained by esterification followed by deprotection reaction of the amino protecting group of compound (13).

Esterification can be carried out by conventionally used method such as the method described in Jikken Kagaku Koza (Experimental Chemistry Series), Vol. 22, Fourth edition, page 43 (1992, Maruzen K. K.). The deprotection reaction of the amino protecting group can also be carried out by a method similar to the one described above.

A compound represented by the general formula (16):

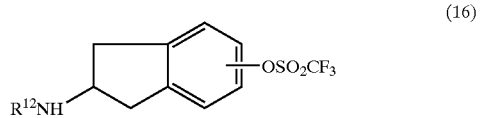

(16)

(wherein $R^{12}$ has the same meaning as the above) is a trifluoromethanesulfonate of a phenolic hydroxy group of compound (13), prepared by using trifluoromethanesulfonic anhydride and pyridine.

A vinyl derivative represented by the general formula (17):

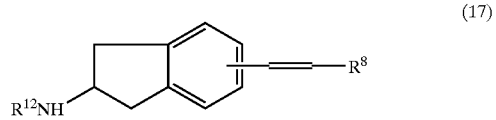

(17)

(wherein $R^8$ and $R^{12}$ have the same meaning as the above) can be prepared by a cross coupling reaction of a trifluoromethanesulfonate (16) and a catechol borane derivative represented by the general formula (18):

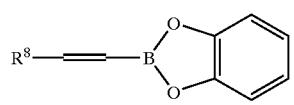

(18)

(wherein $R^2$ has the same meaning as the above) or a boronic acid derivative represented by the general formula (19):

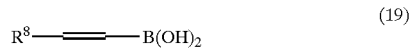

(19)

(wherein $R^8$ has the same meaning as the above) using a palladium catalyst and a base. The palladium catalyst as used herein is $Pd(PPh_3)_4$, $PdCl_2(dppf)$ (dppf=1,1'-bis (diphenylphosphino)ferrocene, $Pd(DBA)_2$/diphenyl (2,4,6-trimethoxyphenyl)phosphine (DBA=dibenzalacetone), $Pd(DBA)_2$/bis(2,4,6-trimethoxyphenyl)phenylphosphine, and the like, the base is tripotassium phosphate, potassium carbonate, sodium carbonate, potassium hydroxide, sodium hydroxide, sodium ethoxide, and the like, and the solvent used is tetrahydrofuran, dioxane, dimethylformamide, toluene, benzene, dimethoxyethane, ethanol, and the like.

Furthermore, in order to prevent the decomposition of palladium catalysts, potassium iodide, potassium bromide, lithium chloride, and the like may be added. Preferably, any of the above palladium catalysts is used, any of tripotassium phosphate, potassium carbonate and sodium carbonate is used as the base, any of tetrahydrofuran, dioxane, dimethylformamide and a mixed solvent of toluene and ethanol is used as the solvent, and any of potassium bromide and lithium chloride is used as the additive. Preferred reaction temperature is room temperature to 120° C.

A compound represented by the general formula (20):

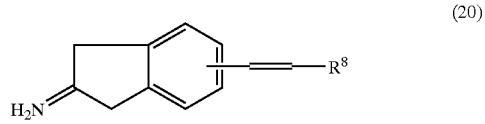

(20)

(wherein $R^0$ has the same meaning as the above) can be obtained by removing the amino protecting group of compound (17) with an acid such as trifluoromethanesulfonic acid, methanesulfonic acid, hydrogen bromide, hydrochloric acid, trifluoroacetic acid, and the like, wherein the compound is obtained as a salt with the acid used.

A carboxylic acid represented by the general formula (21):

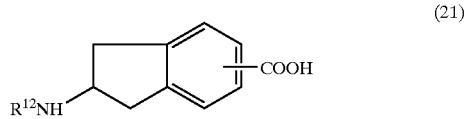

(21)

(wherein $R^{12}$ has the same meaning as the above) is synthesized from the vinyl derivative (17) via 1) the formation of an aldehyde by oxidative cleavage, 2) the oxidation of the aldehyde to a carboxylic acid or carboxylic acid ester, and 3) the hydrolysis of the carboxylic acid ester (when oxidized to the carboxylic acid ester).

In the formation of an aldehyde by oxidative cleavage in 1), preferably an oxidizing agent of osmium tetraoxide and sodium periodate are used, and the reaction is conducted in a mixed solvent of any of organic solvent such as ether, dioxane, acetone, tetrahydrofuran, and water.

In the oxidation in 2), preferably any of manganese dioxide, silver oxide, and argentic oxide (AgO) as the oxidizing agent, an alcohol such as methanol and ethanol as the solvent is used, and the reaction is carried out at room temperature to 50° C. Alternatively, reaction is carried out using sodium chlorite, sodium hydrogen phosphate, isobutylene, or hydrogen peroxide, an aqueous solvent such as tert-butanol/water or acetonitrile/water. When manganese dioxide is used as the oxidizing agent, a carboxylic acid ester corresponding to the alcohol used is formed, which is hydrolyzed in a known method using an alkali to produce a carboxylic acid.

The carboxylic acid is also produced directly by reacting the vinyl derivative (17) with potassium permanganate.

An amide derivative represented by the general formula (22):

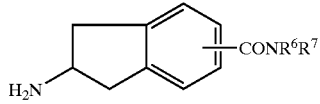

(22)

(wherein $R^6$ and $R^7$ have the same meaning as the above) can be prepared by the amidation of the carboxylic acid (21) followed by the deprotection reaction of the amino protecting group. Amidation is carried out using a conventionally used method such as is described in Jikken Kagaku Koza (Experimental Chemistry Series), Vol. 22, Fourth edition, pages 137 (1992, Maruzen K. K.) or Peputido Goseino Kisoto Jikken (The Basic and Experimental Peptide Synthesis), Nobuo Izumiya, Tetsuo Kato, Haruhiko Aoyagi, Michinori Waki, (1985, Maruzen K. K.). The deprotection reaction of the amino protecting group can be carried out in a similar method as described above. When an acid is used in the deprotection reaction, the amide derivative (22) can be prepared as a salt with the acid used.

An ester derivative represented by the general formula (23):

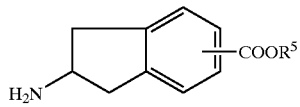

(23)

(wherein $R^5$ has the same meaning as the above) can be prepared by the esterification of the carboxylic acid (21) followed by the deprotection reaction of the amino protecting group. The esterification and the deprotection reaction of the amino protecting group can be carried out in a similar general method as described above. When an acid is used in the deprotection reaction, it can be prepared as a salt with the acid used.

A compound represented by the general formula (22):

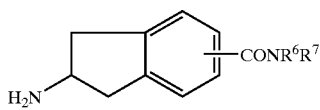

(22)

(wherein $R^6$ and $R^7$ have the same meaning as the above), and some of a compound represented by the general formula (23):

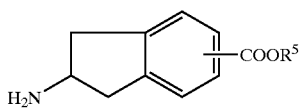

(23)

(wherein $R^5$ has the same meaning as the above) can also be prepared by the following method:

First, an acetyl group is introduced into the benzene ring of a compound (24):

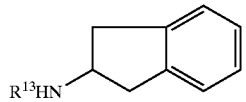

(24)

(wherein $R^{13}$ is a protecting group of an amino group, preferably an acetyl group or a benzoyl group), to be converted to compound (25):

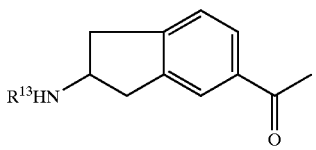

(25)

(wherein $R^{13}$ has the same meaning as the above). The acetylation is preferably carried out using acetyl chloride, acetic anhydrous, or a Lewis acid such as aluminum chloride, iron (III) chloride, and titanium (IV) chloride, and a solvent such as nitrobenzene, carbon disulfide, methylene chloride and ethylene chloride. The acetyl derivative (25) obtained is then reacted with a hypohalite. Preferably, it is reacted with a hypohalite such as sodium hypochlorite or sodium hypobroinite at room temperature in a aqueous solvent such as dioxane/water, tetrahydrofuran/water. This produces compound (26):

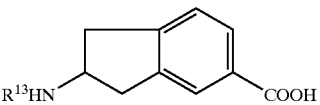

(26)

(wherein $R^{13}$ has the same meaning as the above), and then the protecting group of the amino group is removed with an acid to yield a deprotection derivative (27):

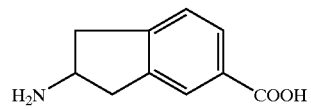

(27)

as a salt with the acid used.

Another protecting group is introduced to the amino group to produce a compound (28):

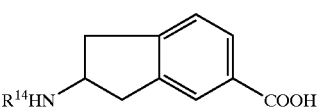

(28)

(wherein $R^{14}$ is, for example, a tert-butoxycarbonyl group or a benzyloxycarbonyl group), which is then esterified and deprotected again to obtain an ester derivative represented by the general formula (29):

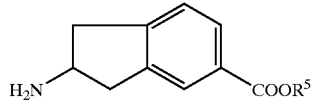

(29)

(wherein R⁵ has the same meaning as the above), and a salt thereof, or which is then amidated and deprotected again to obtain an amide derivative represented by the general formula (30):

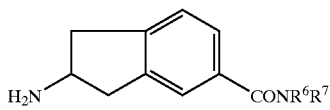

(30)

(wherein R⁶ and R⁷ have the same meaning as the above), and a salt thereof. The ester derivative represented by the general formula (29) can also be prepared by heating compound (27) in an alcohol in the presence of thionyl chloride, or an acid such as hydrogen chloride or toluenesulfonic acid.

Compound (I) or compound (XVII) to be used as an active ingredient of the present invention thus obtained can be converted as desired to various salts, and can be purified by means of recrystallization, column chromatography, and the like.

Furthermore, some of the compound (I) and compound (XVII) to be used as an active ingredient of the present invention have an asymmetric center and these optical isomers are also included as compounds to be used as an active ingredient of the present invention, and can be obtained as single optical active isomers by separating from the racemates using various methods. Examples of the methods used include:

(1) a method of separation using optically active columns;
(2) a method of using optically active acids or bases to produce a salt, which is then separated by recrystallization;
(3) a method of separation using enzymatic reactions; and
(4) a method of separation using combinations of the above (1) to (3).

The drug effects of these compounds can be evaluated in animal models of myocarditis, dilated cardiomyopathy or heart failure using common administration methods. The animal models used must exhibit an increase in NO or TNF-α in the blood or biopsy tissue and allow observation of abnormal cardiac function, and the widely used EMC virus-infected mice (Shioi T, et al. (1997) J. Mol. Cell Cardiol. 29, 2327–2334) may be suitably utilized. These compounds exhibit an improving effect on some or all cardiac functions in such animal models.

The NF-κB inhibitors of the invention are characterized by suppressing production of NO and TNF-α and are therefore useful for inflammatory heart diseases, among which there may be specifically mentioned acute myocarditis and chronic myocarditis resulting from chronic acute myocarditis, as well as dilated cardiomyopathy advanced from acute myocarditis. Acute myocarditis generally includes idiopathic cardiomyopathy so classified because the cause is unknown, and viral myocarditis in which viral infection has been directly or indirectly confirmed. It may also be used for heart failure caused by excess production of inflammatory mediators such as NO and TNF-α.

When the compounds of the present invention are used as the above-mentioned pharmaceutical compositions, they can be used orally in the form of tablets, capsules, elixirs, microcapsules, and the like, or parenterally in the form of injections and the like such as solutions or suspensions with water or other pharmaceutically acceptable liquids. For example, they can be prepared by mixing the invention compound with pharmaceutically acceptable carriers, flavoring agents, excipients, stabilizers, and the like in a commonly recognized form. Additives that can be blended into tablets etc. include, for example, binders such as gelatin, swelling agents such as corn starch, excipients such as crystalline cellulose, lubricants such as magnesium stearate, and the like when formulated into capsules, the above compositions may further include liquid carriers. Aseptic compositions for injection can also be formulated in the conventional manner.

As aqueous solutions for injection, there may be mentioned isotonic solutions that contain glucose etc., and they may be used in combination with suitable solubilizer such as polyethyleneglycol. Buffers, stabilizers, preservatives, antioxidants, soothing agents, and the like may also be blended. The pharmaceutical preparations thus obtained can be administered to mammals including humans. Though the dosage varies depending on the route of administration, the disease to which it is applied, the symptoms being treated and the patient undergoing treatment etc. the daily dose per human adult, it is, when given orally, generally about 0.01 to 100 mg, preferably about 0.1 to 50 mg, and more preferably about 1.0 to 25 mg. When they are given parenterally, the daily dose per human adult is generally intravenously administered at amounts of about 0.001 to 50 mg, preferably about 0.01 to 25 mg, more preferably about 0.1 to 10 mg.

According to the invention, the NF-κB inhibitors may be administered alone without combination of other active ingredients, but administration may be carried out in the form of drug preparations containing other active ingredients, considering the nature of the target disease, symptoms and complications. The inhibitors may also be used together with drugs comprising these other active ingredients. Examples of other active ingredients that may be used for such cases include immunosuppressants, ACE inhibitors, beta blockers, diuretics, cardiac stimulants and the like.

The use of such other active ingredients may be expected to exhibit an even more excellent therapeutic effect for graft rejection reaction, autoimmune diseases, chronic rheumatoid arthritis, nephritis, etc. in the case of immunosuppressants, for hypertension, arteriosclerosis, etc. in the case of ACE inhibitors, for hypertension, arteriosclerosis, etc. in the case of beta blockers, for nephritis, renal failure, etc. in the case of diuretics, and for acute heart failure, autoimmune diseases, chronic rheumatoid arthritis, graft rejection reaction, etc. in the case of cardiac stimulants.

There are no particular restrictions on the amounts of other active ingredients used, and for example, they may be determined in consideration of their minimum effective dosages alone, exhibited side-effects, etc.

For treatment, a preparation containing the NF-κB inhibitor alone as the active ingredient, a preparation containing it together with other active ingredients and the method of combination therapy may be appropriately selected by a physician depending on the age and symptoms of the patient, etc.

EXAMPLES

The present invention will now be explained in further detail by way of examples.

Production Example 1

3-[4-(5,6-Dimothoxy-3-methyl-1,4-benzoquinon-2-ylmethyl)phenyl]propionic Acid

Step 1. 2-{4-[Hydroxy-(2,3,5-tetramethoxy-6-methylphenyl)methyl]phenyl}-1,3-dioxolane To an ice-cold solution of 2,3,4,5-tetramethoxy-6-methylbenzaldehyde (5.03 g, 20.94 mmol) in THF (200 ml) was added dropwise a Grignard reagent prepared from 2-(4-bromophenyl)-1,3-dioxolane (12.0 g, 52.4 mmol) and magnesium (1.40 g, 57.6 mmol), and then stirred at room temperature for 4 hours. The reaction mixture was poured into water and was extracted with ether. After the extract was washed with water and dried, and then the solvent was distilled off. The residue was purified by a silica gel column chromatography (hexane:ethyl acetate=3:1) to yield the title compound (7.80 g, 20.0 mmol, yield 96%).

Step 2. 4-[Acetoxy-(2,3,4,5-tetramethoxy-6-methylphenyl)methyl]benzaldehyde

The compound (7.80 g, 20.0 mmol) obtained in Step 1 was dissolved in methylene chloride (300 ml), and then acetic anhydride (6.12 g, 60.0 mmol), pyridine (4.74 g, 59.9 mmol), and 4-dimethylaminopyridine (1.22 g, 10.0 mmol) were added thereto, which was then stirred at room temperature for 16 hours.

After the reaction mixture was washed with a 5% aqueous solution of hydrochloric acid and saturated saline, it was dried and the solvent was distilled off. The residue and p-toluenesulfonic acid monohydrate (200 mg) were dissolved in acetone (300 ml), which was stirred at room temperature for 6 hours. After the reaction mixture was concentrated under reduced pressure, water and ether were added for extraction. The extract was washed with water, dried, and then the solvent was distilled off. The residue was purified by a silica gel column chromatography (hexane:ethyl acetate=3:1) to yield the title compound (3.97 g, 10.2 mmol, yield 51%).

Step 1. 3-{4-[Acetoxy-(2,3,4,5-tetramethoxy-6-methylphenyl)ethyl]phenyl}acrylic Acid Ethylester Triethyl phosphonoacetate (1.70 g, 7.58 mmol) was dissolved in THF (150 ml) and sodium hydride (303 mg, 60%, 7.58 mmol) was added at room temperature and then the mixture was stirred for 40 minutes. To the reaction mixture was added dropwise under ice-cooling a solution of the compound (2.26 g, 5.82 mmol) obtained in Step 2 in THF (50 ml) and the mixture was stirred at room temperature for 16 hours. The reaction mixture was poured into water and extracted with ether. The extract was washed with water, dried, and then the solvent was distilled off. The residue was purified by a silica gel column chromatography (hexane:ethyl acetate=3:1) to yield the title compound (2.37 g, 5.17 mmol, yield 89%).

Step 4. 3-[4-(2,3,4,5-Tetramethoxy-6-methylbenzyl)phenyl]acrylic Acid Ethylester To a solution of triethylsilane (720 mg, 6.21 mmol) and trimethylsilyl trifluoromethanesulfonate (TMSOTf) in methylene chloride (250 ml) was added dropwise a solution of the compound (2.37 g, 5.17 mmol) obtained in Step 3 in methylene chloride (50 ml) and the mixture was stirred at room temperature for 30 minutes. The reaction mixture was washed with water, dried, and then the solvent was distilled off. The residue was purified by a silica gel column chromatography (hexane:ethyl acetate=4:1) to yield the title compound (1.90 g, 4.74 mmol, yield 92%).

Step 5. 3-[4-(2,3,4,5-Tetramethoxy-6-methylbenzyl)phenyl]progionic Acid Ethylester The compound (1.07 g, 2.67 mmol) obtained in step 4 was dissolved inmethanol (100 ml) and 5% Pd-carbon (200 mg) was added thereto, which was then stirred under a stream of hydrogen at room temperature for 16 hours. The reaction mixture was filtered and the filtrate was concentrated to yield the title compound (914 mg, 2.27 mmol, yield 85%).

Step 6. 3-[4-(2,3,4,5-Tetramethoxy-6-methylbenzyl)phenyl]propionic Acid

The compound (914 mg, 2.27 mmol) obtained in Step 5 was dissolved in a mixture of an aqueous solution of 2 N sodium hydroxide (30 ml) and 1,4-dioxane (15 ml) and the mixture was stirred at 70° C. for 3 hours. The reaction mixture was acidified by adding concentrated hydrochloric acid and then was extracted with ethyl acetate. The extract was washed with water, dried, and then the solvent was distilled off to yield the title compound (731 mg, 1.95 mmol, yield 86%).

Step 7. 3-[4-(5,6-Dimethoxy-3-methyl-1,4-benzoquinon-2-ylmethyl)phenyl]yropionic Acid The compound (1.00 g, 2.67 mmol) obtained in Step 6 was dissolved in a mixture of acetonitrile (30 ml) and water (10 ml), to which was added CAN (ceric ammonium nitrate) (2.34 g, 4.27 mmol) and the mixture was stirred at room temperature for 30 minutes. The reaction mixture was poured into water and was extracted with ether. After the extract was washed with water and dried, the solvent was distilled off. The residue was purified by a silica gel column chromatography (5% methanol-methylene chloride) and then was crystallized in ethanol/hexane to yield the title compound (662 mg, 1.92 mmol, yield 72%).

Production Example 2

3-[4-(5,6-Dimethoxy-3-methyl-1,4-benzoquinon-2-ylmethyl)phenyl]acrylic Acid

Step 1. 3-[4-(2,3,4,5-Tetramethoxy-6-methylbenzylophenyl]acrylic Acid

The compound (1.35 g, 3.36 mmol) obtained in step 4 of Production Example 1 was dissolved in a mixture of an aqueous solution of 2 N sodium hydroxide (30 ml) and 1,4-dioxane (15 ml), and the mixture was stirred at 70° C. for 3 hours. The reaction mixture was acidified by adding concentrated hydrochloric acid and then was extracted with ethyl acetate. The extract was washed with water, dried, and then the solvent was distilled off to yield the title compound (1.20 g, 3.23 mmol, yield 96%).

Step 2. 3-[4-(5,6-Dimethoxy-3-methyl-1,4-benzoquinon-2-ylmethyl)phenyl]acrylic Acid The compound (589 mg, 1.58 mmol) obtained in Step 1 was dissolved in a mixture of acetonitrile (30 ml) and water (10 ml), to which was added CAN (1.38 g, 2.52 mmol) and the mixture was stirred at room temperature for 1 hour. The reaction mixture was poured into water and was extracted with ether. After the extract was washed with water and dried, the solvent was distilled off. The residue was purified by a silica gel column chromatography (5% methanol-methylene chloride) to yield the title compound (452 mg, 1.32 mmol, yield 84%).

Production Example 3

N-[3-[4-(5,6-Dimethoxy-3-methyl-1,4-benzoquinon-2-ylmethyl)phenyl]propionyl]morpholine To a solution of 3-[4-(5,6-dimethoxy-3-methyl-1,4-benzoquinon-2-ylmethyl)phenyl]propionic acid (100 mg, 0.29 mmol) obtained in Production Example 1 and morpholine (30 mg, 0.35 mmol) in methylene chloride (10 ml) was added 1-ethyl-3-(3-dimethylaminopropyl)carbodiimide hydrochloride (84 mg, 0.44 mmol) and the mixture was stirred at room temperature for 3 hours. The reaction mixture was concentrated under reduced pressure and was purified by a middle-pressure column chromatography using silica gel (hexane:ethyl acetate=1:2).

The yellow powder thus obtained was crystallized from methylene chloride-diethylether to yield the title compound (89 mg, 0.22 mmol, yield 74%) as a yellow crystal.

Production Example 4

N-[3-[4-(5,6-Dimethoxy-3-methyl-1,4-benzoquinon-2-ylmethyl)phenyl]propionyl]thimorpholine To a solution of 3-[4-(5,6-dimethoxy-3-methyl-1,4-benzoquinon-2-ylmethyl)phenyl]propionic acid (27 mg, 0.078 mmol) obtained in Production Example 1 and ethyl chlorocarbonate (15 mg, 0.139 mmol) in THF (10 ml) was added triethylamine (14 mg, 0.139 mmol) at −10° C. followed by stirring for 30 minutes, and then thiomorpholine (20 mg, 0.194 mmol) was added thereto followed by stirring at room temperature for 1 hour. The reaction mixture was diluted with water and extracted with ether. The extract was washed with water, dried, and then the solvent was distilled off. The resulting residue was purified by a middle-pressure column chromatography using silica gel (hexane:ethyl acetate=1:1). The yellow powder thus obtained was crystallized from methylene chloride-diethylether to yield the title compound (26 mg, 0.061 mmol, yield 77%) as a yellow crystal.

Production Examples 5 and 6

N-[3-[4-(5,6-Dimethoxy-3-methyl-1,4-benzoquinon-2-ylmethyl)phenyl]propionyl]thiomorpholine S-Oxide (Production Example 5) and N-[3-[4-(5,6-Dimethoxy-3-methyl-1,4-benzoquinon-2-ylmethyl) phenyl]propionyl]thiomorpholine S-Dioxide (Production Example 6)

To a solution of the compound (200 mg, 0.47 mmol) obtained in Production Example 4 in methylene chloride (50 ml) was added m-chloroperbenzoic acid (121 mg, 0.70 mmol) and the mixture was stirred at room temperature for 5 hours. The reaction mixture was washed with water, dried, and then concentrated under reduced pressure. The crude product thus obtained was purified by a silica gel column chromatography (5% methanol-methylene chloride) to yield the compound (60 mg, yield 28%) of Production Example 5 and the compound (50 mg, yield 24%) of Production Example 6.

Production Examples 7 to 20

According to the method of Production Example 3, the compounds of Production Examples 7 to 20 were synthesized.

Production Example 7

N-[3-[4-(5,6-Dimethoxy-3-methyl-1,4-benzoquinon-2-ylmethyl phenyl]propionyl]piperidine 3-[4-(5,6-dimethoxy-3-methyl-1,4-benzoquinon-2-ylmethyl)phenyl]propionic acid (200 mg, 0.58 mmol) obtained in Production Example 1 and piperidine (64 mg, 0.75 mmol) were used, and a method similar to that described in Production Example 3 was employed to obtain the title compound (118 mg, 0.79 mmol, yield 50%).

Production Example 8

N-[3-[4-(5,6-Dimethoxy-3-methyl-1,4-benzoquinon-2-ylmethyliphenyl]propionyl]dimethylamine 3-[4-(5,6-dimethoxy-3-methyl-1,4-benzoquinon-2-ylmethyl)phenyl]propionic acid (200 mg, 0.58 mmol) obtained in Production Example 1 and dimethylamine hydrochloride (62 mg, 0.75 mmol) and triethylamine (76 mg, 0.75 mmol) were used, and a method similar to that described in Production Example 3 was employed to obtain the title compound (38 mg, 0.10 mmol, yield 18%).

Production Example 9

N-[3-[4-(5,6-Dimethoxy-3-methyl-1,4-benzoquinon-2-ylmethyl)phenyl]propionyl]isopropylamine 3-[4-(5,6-dimethoxy-3-methyl-1,4-benzoquinon-2-ylmethyl)phenyl]propionic acid (200 mg, 0.58 mmol) obtained in Production Example 1 and isopropylamine (44 mg, 0.75 mmol) were used, and a method similar to that described in Production Example 3 was employed to obtain the title compound (46 mg, 0.12 mmol, yield 21%).

Production Example 10

N-[3-[4-(5,6-Dimethoxy-3-methyl-1,4-benzoquinon-2-ylmethyliphenyl]propionyl]ethanolamine 3-[4-(5,6-dimethoxy-3-methyl-1,4-benzoquinon-2-ylmethyl)phenyl]propionic acid (200 mg, 0.58 mmol) obtained in Production Example 1 and ethanolamine (47 mg, 0.75 mmol) were used, and a method similar to that described in Production Example 3 was employed to obtain the title compound (65 mg, 0.18 mmol, yield 29%).

Production Example 11

N-[3-[4-(5,6-Dimethoxy-3-methyl-1,4-benzoquinon-2-ylmethyl)phenyl]propionyl]benzylamine 3-[4-(5,6-dimethoxy-3-methyl-1,4-benzoquinon-2-ylmethyl)phenyl]propionic acid (200 mg, 0.58 mmol) obtained in Production Example 1 and benzylamine (80 mg, 0.75 mmol) were used, and a method similar to that described in Production Example 3 was employed to obtain the title compound (33 mg, 0.08 mmol, yield 13%).

Production Example 12

N-[3-[4-(5,6-Dimethoxy-3-methyl-1,4-benzoquinon-2-ylmethyl)phenyl]propionyl]phenethylamine 3-[4-(5,6-dimethoxy-3-methyl-1,4-benzoquinon-2-ylmethyl)phenyl]propionic acid (200 mg, 0.58 mmol) obtained in Production Example 1 and phenethylamine (91 mg, 0.75 mmol) were used, and a method similar to that described in Production Example 3 was employed to obtain the title compound (61 mg, 0.14 mmol, yield 24%).

Production Example 13

N-[3-[4-(5,6-Dimethoxy-3-methyl-1,4-benzoquinon-2-ylmethyl)phenyl]acryloyl]morpholine 3-[4-(5,6-dimethoxy-3-methyl-1,4-benzoquinon-2-ylmethyl)phenyl]acrylic acid (200 mg, 0.58 mmol) obtained in Production Example 2 and morpholine (65 mg, 0.75 mmol) were used, and a method similar to that described in Production Example 3 was employed to obtain the title compound (102 mg, 0.25 mmol, yield 43%).

Production Example 14

N-[3-[4-(5,6-Dimethoxy-3-methyl-1,4-benzoquinon-2-ylmethyl)phenyl]acryloyl]thimorpholine 3-[4-(5,6-dimethoxy-3-methyl-1,4-benzoquinon-2-ylmethyl)phenyl]acrylic acid (200 mg, 0.58 mmol) obtained in Production Example 2 and thiomorpholine (77 mg, 0.75 mmol) were used, and a method similar to that described in Production Example 3 was employed to obtain the title compound (140 mg, 0.33 mmol, yield 56%).

Production Example 15

N-[3-[4-(5,6-Dimethoxy-3-methyl-1,4-benzoquinon-2-ylmethyl)phenyl]acryloyl]piperidine 3-[4-(5,6-dimethoxy-3-methyl-1,4-benzoquinon-2-ylmethyl)phenyl]acrylic acid (200 mg, 0.58 mmol) obtained in Production Example 2 and piperidine (65 mg, 0.76 mmol) were used, and a method similar to that described in Production Example 3 was employed to obtain the title compound (129 mg, 0.32 mmol, yield 54%).

Production Example 16

N-[3-[4-(5,6-Dimethoxy-3-methyl-1,4-benzoquinon-2-ylmethyl)phenyl]acryloyl]dimethylamine 3-[4-(5,6-dimethoxy-3-methyl-1,4-benzoquinon-2-ylmethyl)phenyl]acrylic acid (200 mg, 0.58 mmol) obtained in Production Example 2 and dimethylamine hydrochloride (61 mg, 0.75 mmol) and triethylamine (76 mg, 0.75 mmol) were used, and a method similar to that described in Production Example 3 was employed to obtain the title compound (23 mg, 0.06 mmol, yield 11%).

Production Example 17

N-[3-[4-(5,6-Dimethoxy-3-methyl-1,4-benzoquinon-2-ylmethyl)phenyl]acryloyl]isopropylamine 3-[4-(5,6-dimethoxy-3-methyl-1,4-benzoquinon-2-ylmethyl)phenyl]acrylic acid (200 mg, 0.58 mmol) obtained in Production Example 2 and isopropylamine (44 mg, 0.75 mmol) were used, and a method similar to that described in Production Example 3 was employed to obtain the title compound (48 mg, 0.13 mmol, yield 22%).

Production Example 18

N-[3-[4-(5,6-Dimethoxy-3-methyl-1,4-benzoquinon-2-ylmethyl)phenyl]acryloyl]ethanolamine 3-[4-(5,6-dimethoxy-3-methyl-1,4-benzoquinon-2-ylmethyl)phenyl]acrylic acid (200 mg, 0.58 mmol) obtained in Production Example 2 and ethanolamine (46 mg, 0.75 mmol) were used, and a method similar to that described in Production Example 3 was employed to obtain the title compound (14 mg, 0.04 mmol, yield 6%).

Production Example 19

N-[3-[4-(5,6-Dimethoxy-3-methyl-1,4-benzoquinon-2-ylmethyl)phenyl]acryloyl]benzylamine 3-[4-(5,6-dimethoxy-3-methyl-1,4-benzoquinon-2-ylmethyl)phenyl]acrylic acid (200 mg, 0.58 mmol) obtained in Production Example 2 and benzylamine (80 mg, 0.75 mmol) were used, and a method similar to that described in Production Example 3 was employed to obtain the title compound (104 mg, 0.24 mmol, yield 42%).

Production Example 20

N-[3-[4-(5,6-Dimethoxy-3-methyl-1,4-benzoquinon-2-ylmethyl)phenyl]acryloyl]phenethylamine 3-[4-(5,6-dimethoxy-3-methyl-1,4-benzoquinon-2-ylmethyl)phenyl]acrylic acid (200 mg, 0.58 mmol) obtained in Production Example 2 and phenethylamine (91 mg, 0.75 mmol) were used, and a method similar to that described in Production Example 3 was employed to obtain the title compound (170 mg, 0.38 mmol, yield 65%).

Production Example 21

4-(5,6-Dimethoxy-3-methyl-1,4-benzoquinon-2-ylmethyl)benzoic Acid

Method A
Step 1. 4-(Hydroxy-(2,3,4,5-tetramethoxy-6-methylphenyl)methyl]benzoic Acid After adding dropwise an aqueous solution (20 ml) of silver nitrate (3.06 g, 18.00 mmol) to an aqueous solution of 1 N sodium hydroxide (36 ml), a solution of 4-[acetoxy-(2,3,4,5-tetramethoxy-6-methylphenyl)methyl]benzaldehyde (2.34 g, 6.00 mmol) obtained in Step 2 of Production Example 1 in THF (30 ml) was added dropwise and the mixture was stirred at room temperature for 5 hours. The reaction mixture was filtered and the solid was washed with hot water. The filtrate and the wash solution were combined, which was then acidified with concentrated hydrochloric acid and then was extracted with ether. The extract was dried and the solvent was distilled off to yield the title compound (2.3 g, 6.37 mmol, yield 100%).

NMR (CDCl$_3$): 2.27 (3H, s), 3.30 (3H, s), 3.75 (1H, m), 3.82 (3H, s), 3.85 (3H, s), 3.94 (3H, s), 6.04 (1H, broad), 7.42 (2H, m), 8.06 (2H, m); FABMS (m/z): 362 (M)$^+$.

Step 2. 4-(2,3,4,5-Tetramethoxy-6-metylenzyl)benzoic Acid

To a solution of triethylsilane (1.39 ml, 8.74 mmol) and TMSOTf (0.056 ml, 0.31 mmol) in methylene chloride (30 ml) was added dropwise a solution of the compound (2.26 g, 6.24 mmol) obtained in Step 1 in methylene chloride (12 ml) and the mixture was stirred at room temperature for 4 hours. The reaction mixture was washed with water, dried, and then the solvent was distilled off to yield the title compound (1.98 g, 5.75 mmol, yield 96%).

NMR (CDCl$_3$): 2.07 (3H, s), 3.70 (3H, s), 3,79 (3H, s), 3.92 (3H, s), 3.95 (3H, s), 4.07 (2H, s), 7.20 (2H, m), 7.99 (2H, m); FABMS (m/z): 346 (M+H)$^+$.

Step 3. 4-(5,6-Dimethoxy-3-methyl-1,4-benzoquinon-2-ylmethyl)benzoic Acid

The compound (1.98 g, 5.75 mmol) obtained in Step 2 was dissolved in a mixture of acetonitrile (40 ml) and water (15 ml), to which was added CAN (7.90 g, 14.5 mmol) and the mixture was stirred at room temperature for 40 minutes. The reaction mixture was poured into water and was extracted with ethyl acetate. After the extract was washed with water and dried, the solvent was distilled off. Ether was added to the residue and the resulting precipitate was filtered to yield the title compound (1.82 9, 5.76 mmol, yield 99%).

Method B
Step 1. p-Iodobenzoic Acid Methylester p-iodobenzoic acid (500 mg, 2.02 mmol) was dissolved in methanol (30 ml), to which was added 2M trimethylsilyl diazomethane/hexane solution (13 ml) and the mixture was stirred at room temperature for 2 hours. The reaction mixture was concentrated under reduced pressure to yield a crude product (500 mg) of the title compound. This was used as a raw material in the subsequent reaction without purification.

NMR (CDCl$_3$): 3.91 (3H, s), 7.74 (2H, d, J=8.4 Hz), 7.80 (2H, d, J=8.5 Hz); FABMS (m/z): 263 (M+H)$^+$.

Step 2. 4-[Hydroxy-(2,3,4,5-tetramethoxy-6-methylphenyl)methyl]benzoic Acid Methylester To a solution of zinc chloride (1.91 mmol) in dry tetrahydrofuran (9.6 ml) was added under ice-cooling a 1.4 M methyllithium/ether solution (4.1 ml, 5.73 mmol), and the mixture was stirred at 0° C. for 30 minutes. The reaction mixture was cooled to −78° C., to which was added a solution of the compound (500 mg, 1.91 mmol) obtained in Step 1 in dry tetrahydrofuran (2.0 ml) and the mixture was further stirred at −78° C. for 4 hours. Subsequently, a solution of 2,3,4,5-tetramethoxy-6-methylbenzaldehyde (1.38 g, 5.73 mmol) in dry tetrahydrofuran (2 ml) was added and the mixture was stirred overnight at room temperature. To the reaction mixture an aqueous solution of saturated ammonium chloride (2.5 ml) was added at 0° C. After concentrating under reduced pressure, the concentrate was diluted with water and extracted three times with chloroform. After the organic layer was dried, the solvent was distilled off. After purification by a silica gel column chromatography (ethyl acetate:hexane=1:2), the title compound (237 mg, 0.63 mmol, yield 33%) was obtained.

NMR (CDCl$_3$): 2.26 (3H, s), 3.28 (3H, s), 3,82 (3H, s), 3.85 (3H, s), 3.90 (3H, s), 3.94 (3H, s), 5.03 (1H, m), 6.01 (1H, d, J=10.5 Hz), 7.38 (2H, d, J=8.2 Hz), 7.99 (2H, d, J=8.4 Hz); FABMS (m/z): 376 (M+H)$^+$.

Step 3. 4-(2,3,4,5-Tetramethoxy-6-methylbenzyl)benzoic Acid Methylester

To a solution of triethylsilane (88 mg, 0.76 mmol) and THSOTf (0.004 ml) in methylene chloride (2 ml) was added dropwise a solution of the compound (237 mg, 0.63 mmol) obtained in Step 2 in methylene chloride (2 ml) and the mixture was stirred at room temperature for 4 hours. The reaction mixture was washed with saturated saline, dried, and then the solvent was distilled off. The residue was purified by a silica gel column chromatography (ethyl acetate:hexane=1:6) to yield the title compound (160 mg, 0.45 mmol, yield 71%).

NMR (CDCl$_3$): 2.06 (3H, s), 3.68 (3H, s), 3,78 (3H, s), 3.88 (3H, s), 3.92 (3H, s), 3.94 (3H, s), 4.05 (2H, s), 7.16 (2H, d, J=8.1 Hz), 7.91 (2H, d, J=8.1 Hz); FABMS (m/z): 360 (M+H)$^+$.

Step 4. 4-(2,3,4,5-Tetraethoxy-6-methylbenzyl)benzoic Acid

The compound (160 mg, 0.45 mmol) obtained in Step 3 was dissolved in a mixture of an aqueous solution of potassium carbonate (91 mg, 0.66 mmol) in water (1 ml) and methanol (2 ml) and the mixture was stirred at 70° C. for 3 hours. The reaction mixture was acidified by adding concentrated hydrochloric acid and then was extracted with diethylether. The extract was washed with water, dried, and then the solvent was distilled off to yield the title compound (116 mg, 0.34 mmol, yield 76%).

Step 5. 4-(5,6-Dimethoxy-3-methyl-1,4-benzoquinon-2-ylmethyl Benzoic Acid

The compound (116 mg, 0.34 mmol) obtained in Step 4 was dissolved in a mixture of acetonitrile (2.2 ml) and water (0.81 ml), to which was added CAN (447 mg, 0.82 mmol). The mixture was stirred at room temperature for 30 minutes. The reaction mixture was poured into water and was extracted with methylene chloride. After the extract was washed with water and dried, the solvent was distilled off. The residue was purified by a silica gel column chromatography (methylene chloride:methanol=8:1) to yield the title compound (92 mg, 0.29 mmol, yield 85%).

Production Example 22

N-[4-(5,6-Dimethoxy-3-methyl-1,4-benzoquinon-2-ylmethyl)benzoyl]morpholine

To 4-(5,6-dimethoxy-3-methyl-1,4-benzoquinon-2-ylmethyl)benzoic acid (100 mg, 0.31 mmol) obtained in Production Example 21 was added oxalyl chloride (0.3 ml) and the mixture was stirred at room temperature for 1 hour. After distilling off the solvent and drying under reduced pressure, an acid chloride was obtained which was dissolved in methylene chloride (2 ml). Morpholine (0.28 ml, 3.3 mmol) was added under ice-cooling and then the mixture was stirred at the same temperature for 30 minutes. The residue obtained after distilling off the solvent was purified by a silica gel column chromatography (hexane:ethyl acetate=1:5) to yield the title compound (56 mg, 0.15 mmol, yield 44%).

Production Example 23

N-[4-(5,6-Dimethoxy-3-methyl-1,4-benzoquinon-2-ylmethyl)benzoyl]isopropylamine 4-(5,6-dimethoxy-3-methyl-1,4-benzoquinon-2-ylmethyl)benzoic acid (100 mg, 0.31 mmol) obtained in Production Example 21 and isopropylamine (0.28 ml, 3.3 mmol) were used, and a method similar to that described in Production Example 22 was employed to obtain the title compound (58 mg, 0.16 mmol, yield 49%).

Production Example 24

N-[4-(5,6-Dimethoxy-3-methyl-1,4-benzoquinon-2-ylmethyl)benzoyl]piperidine

To a solution of 4-(5,6-dimethoxy-3-methyl-1,4-benzoquinon-2-ylmethyl)benzoic acid (50 mg, 0.16 mmol) obtained in Production Example 21 and piperidine (0.021 ml, 0.21 mmol) in methylene chloride (2 ml) was added 1-ethyl-3-(3-dimethylaminopropyl)carbodiimide hydrochloride (46 mg, 0.24 mmol), and then the mixture was stirred at room temperature for 1 hour. The reaction mixture was concentrated under reduced pressure and was purified by a silica gel column chromatography (hexane:ethyl acetate=1:2) to yield the title compound (30 mg, 0.08 mmol, yield 50%).

Production Example 25

N-[4-(5,6-Dimethoxy-3-methyl-1,1-benzoquinon-2-ylmethyl)benzoyl]thiomorpholine 4-(5,6-dimethoxy-3-methyl-1,4-benzoquinon-2-ylmethyl)benzoic acid (100 mg, 0.32 mmol) obtained in Production Example 21 and thiomorpholine (0.035 ml, 0.35 mmol) were used, and a method similar to that described in Production Example 24 was employed to obtain the title compound (65 mg, 0.16 mmol, yield 51%).

Production Example 26

4-[4-(5,6-Dimethoxy-3-methyl-1,4-benzoquinon-2-ylmethyl]phenyl-n-butyric Acid

Method A

Step 1. 3-[4-(2,3,4,5-Tetramethoxy-6-methylbenzyl)phenyl] progionic Acid Diazomethyl Ketone 3-(4-(2,3,4,5-tetramethoxy-6-methylbenzyl)phenyl) propionic acid (750 mg, 2.00 mmol) obtained in Step 6 of Production Example 1 was dissolved in methylene chloride (2 ml), to which was added oxalyl chloride (2 ml) and the mixture was stirred at room temperature for 1 hour. The acid chloride obtained after distilling off the solvent was dried under reduced pressure. To a diazomethane solution [prepared using p-toluenesulfonyl-N-methyl-N-nitrosoamide (8.6 g), potassium hydroxide (2.4 g), carbitol (14 ml), water (5 ml), and ether (100 ml)] was added under ice-cooling triethylamine (0.7 ml) and then an ether solution of the above acid chloride (10 ml) was added. The reaction mixture was stirred at the same temperature for 2 hours.

After the solvent was distilled off, the residue was purified by a silica gel column chromatography (hexane ethyl acetate=2:1 to 1:1) to yield the title compound (380 mg, 0.98 mmol, yield 49%).

NMR (CDCl$_3$): 2.07 (3H, 9), 2.60 (2H, m), 2.90 (2H, m), 3.69 (3H, s), 3.78 (3H, s), 3.91 (3H, s), 3.93 (3H, s), 3.97 (2H, s), 5.16 (1H, broad), 7.04 (4H, m); FABMS (m/z): 398 (M)$^+$.

Step 2. 4-[4-(2,3,4,5-Tetramethoxy-6-methylbenzyl) phenyl]-n-butyric Acid

Sodium thiosulfate pentahydrate (230 mg, 0.93 mmol) and silver oxide (130 mg, 0.56 mmol) were dissolved in water (5 ml) and the mixture was heated to 50° C. to 70° C. A solution of the compound (380 mg, 0.98 mmol) obtained in Step 1 in dioxane (3.5 ml) was added dropwise, and the mixture was stirred at the same temperature for 10 minutes. The reaction mixture was cooled and was acidified with an aqueous solution of diluted nitric acid and then was extracted with ether. The extract was washed with water, dried, and then the solvent was distilled off to yield the title compound (210 mg, 0.54 mmol, yield 93%).

NMR (CDCl$_3$): 1.92 (2H, m), 2.08 (3H, s), 2.34 (2H, m), 2.61 (2H, m), 3.70 (6H, s), 3.78 (2H, s), 3.91 (3H, s), 3.93 (3H, s), 7.03 (4H, m); FABMS (m/z): 388 (M)$^+$.

Step 3. 4-[4-(5,6-Dimethoxy-3-methyl-1,4-benzoquinon-2-ylmethyl)phenyl]-n-butyric Acid The compound (260 mg, 0.67 mmol) obtained in Step 2, acetonitrile (5 ml), water (1.6 ml), and CAN (920 mg, 1.70 mmol) were used, and a method similar to that described in Step 3 of Production Example 21 was employed and then the reaction mixture was purified by a silica gel column chromatography (methylene chloride:methanol=9:1) to yield the title compound (154 mg, 0.43 mmol, yield 74%).

Method B

Step 1. 3-[4-(5,6-Dimethoxy-3-methyl-1,4-benzoquinon-2-ylmethyl)phenyl]propionic Acid Diazomethyl Ketone The 3-[4-(5,6-dimethoxy-3-methyl-1,4-benzoquinon-2-ylmethyl)phenyl]propionic acid (340 mg, 1.00 mmol) obtained in Step 7 of Production Example 1, oxalyl chloride (0.5 ml), and triethylamine (0.14 ml) were used, and a method similar to that described in Step 1 of Method A of Production Example 26 was employed to obtain the title compound (140 mg, 0.38 mmol, yield 38%).

NMR (CDCl$_3$): 2.07 (3H, s), 2.59 (2H, m), 2.90 (2H, m), 3.80 (2H, s), 3.98 (3H, s), 3.99 (3H, s), 5.17 (1H, broad), 7.08 (4H, m); FABMS (m/z): 369 (M+H)$^+$.

Step 2. 4-[4-(5,6-Dimethoxy-3-methyl-1,4-benzoquinon-2-ylmethyl)phenyl]-n-butyric Acid The compound (70 mg, 0.20 mmol) obtained in Step 1, sodium thiosulfate pentahydrate (81 mg, 0.33 mmol), and silver oxide (44 mg, 0.19 mmol) were used, and a method similar to that described in Step 2 of Method A of Production Example 26 was employed to obtain the title compound (13 mg, 0.04 mmol, yield 20%).

Production Example 27

N-[4-[4-(5,6-Dimethoxy-3-methyl-1,4-benzoquinon-2-ylmethyl)phenyl]butanoyl]morpholine 3-[4-(5,6-dimethoxy-3-methyl-1,4-benzoquinon-2-ylmethyl)phenyl]propionic acid diazomethyl ketone (70 mg, 0.20 mmol) obtained in Step 1 of Method B of Production Example 26 was dissolved in dry ethanol (5 ml), to which were added silver nitrate (34 mg, 0.20 mmol) and morpholine (0.090 ml, 1.0 mmol), and the mixture was heated to reflux for 20 minutes. The reaction mixture was filtered and the solid was washed with ethanol. The filtrate and the wash solution were combined and the solvent was distilled off, the resulting residue was purified by a silica gel column chromatography (hexane:ethyl acetate=1:3) to yield the title compound (42 mg, 0.098 mmol, yield 49%).

Production Example 28

N-[4-[4-(5,6-Dimethoxy-3-methyl-1,4-benzoquinon-2-ylmethyl)phenyl]butanoyl]thiomorpholine 4-[4-(5,6-dimethoxy-3-methyl-1,4-benzoquinon-2-ylmethyl)phenyl)-n-butyric acid (50 mg, 0.14 mmol) obtained in Production Example 26 and thiomorpholine (0.016 ml, 0.15 mmol) were used, a method similar to that described in Production Example 24 was employed to obtain the title compound (15 mg, 0.034 mmol, yield 24%).

Production Example 29

N-[4-[4-(5,6-Dimethoxy-3-methyl-1,4-benzoquinon-2-ylmethyl)phenyl]butanoyl]piperidine 4-[4-(5,6-dimethoxy-3-methyl-1,4-benzoquinon-2-ylmethyl)phenyl]-n-butyric acid (50 mg, 0.14 mmol) obtained in Production Example 26 and piperidine (0.015 ml, 0.15 mmol) were used, and a method similar to that described in Production Example 24 was employed to obtain the title compound (19 mg, 0.045 mmol, yield 32%).

Production Example 30

N-[4-[4-(5,6-Dimethoxy-3-methyl-1,4-benzoquinon-2-ylmethyl)phenyl]butanoyl]isopropylamine 4-[4-(5,6-dimethoxy-3-methyl-1,4-benzoquinon-2-ylmethyl)phenyl]-n-butyric acid (50 mg, 0.14 mmol) obtained in Production Example 26 and isopropylamine (0.013 ml, 0.15 mmol) were used, and a method similar to that described in Production Example 24 was employed to obtain the title compound (30 mg, 0.075 mmol, yield 54%).

Production Example 31

3-[3-(5,6-Dimethoxy-3-methyl-1,4-benzoquinon-2-ylmethyl)phenyl]propionic Acid 2,3,4,5-tetramethoxy-6-methylbenzaldehyde (960 mg, 4.00 mmol) and 2-(3-bromophenyl)-1,3-dioxolane (2.3 g, 10 mmol) were used, and a method similar to that described in Production Example 1 was employed to obtain the title compound (300 mg, 0.87 mmol).

Production Example 32

N-[3-[3-(5,6-Dimethoxy-3-methyl-1,4-benzoquinon-2-ylmethyl)phenyl]propionyl]piperidine 3-[3-(5,6-dimethoxy-3-methyl-1,4-benzoquinon-2-ylmethyl)phenyl]propionic acid (65 mg, 0.19 mmol) obtained in Production Example 31 and piperidine (0.022 ml, 0.21 mmol) were used, and a method similar to that described in Production Example 24 was employed to obtain the title compound (27 mg, 0.066 mmol, yield 35%).

Production Example 33

N-[3-[3-(5,6-Dimethoxy-3-methyl-1,4-benzoquinon-2-ylmethyl)phenyl]propionyl]thiomorpholine 3-[3-(5,6-dimethoxy-3-methyl-1,4-benzoquinon-2-ylmethyl)phenyl]propionic acid (65 mg, 0.19 mmol)

obtained in Production Example 31 and thiomorpholine (0.022 ml, 0.21 mmol) were used, and a method similar to that described in Production Example 24 was employed to obtain the title compound (26 mg, 0.061 mmol, yield 32%).

Production Example 34

N-[3-[3-(5,6-Dimethoxy-3-methyl-1,4-benzoquinon-2-ylmethyl)phenyl]propionyl]morpholine 3-[3-(5,6-dimethoxy-3-methyl-1,4-benzoquinon-2-ylmethyl)phenyl]propionic acid (65 mg, 0.19 mmol) obtained in Production Example 31 and morpholine (0.019 ml, 0.21 mmol) were used, and a method similar to that described in Production Example 24 was employed to obtain the title compound (29 mg, 0.069 mmol, yield 36%).

Production Example 35

N-[3-[3-(5,6-Dimethoxy-3-methyl-1,4-benzoquinon-2-ylmethyl)phenyl]propionyl]isopropylamine 3-[3-(5,6-dimethoxy-3-methyl-1,4-benzoquinon-2-ylmethyl)phenyl]propionic acid (65 mg, 0.19 mmol) obtained in Production Example 31 and isopropylamine (0.019 ml, 0.21 mmol) were used, and a method similar to that described in Production Example 24 was employed to obtain the title compound (12 mg, 0.031 mmol, yield 16%).

Production Example 36

3-[3-(5,6-Dimethoxy-3methyl-1,4-benzoquinon-2-ylmethyl)phenyl]acrylic Acid

3-[3-(2,3,4,5-tetramethoxy-6-methylbenzyl)phenyl] acrylic acid ethylester (300 mg, 0.75 mmol) was used, and a method similar to that described in Production Example 2 was employed to obtain the title compound (220 mg, 0.64 mmol, yield 85%).

Production Example 37

N-[3-[3-(5,6-Dimethoxy-3-methyl-1,4-benzoquinon-2-ylmethyl)phenyl]acryloyl]piperidine 3-[3-(5,6-dimethoxy-3-methyl-1,4-benzoquinon-2-ylmethyl)phenyl]acrylic acid (55 mg, 0.16 mmol) obtained in Production Example 36 and piperidine (0.018 ml, 0.18 mmol) were used, and a method similar to that described in Production Example 24 was employed to obtain the title compound (30 mg, 0.073 mmol, yield 46%).

Production Example 38

N-[3-[3-(5,6-Dimethoxy-3-methyl-1,4-benzoquinon-2-ylmethyl)phenyl]acryloyl]morpholine 3-(3-(5,6-dimethoxy-3-methyl-1,4-benzoquinon-2-ylmethyl)phenyl]acrylic acid (55 mg, 0.16 mmol) obtained in Production Example 36 and morpholine (0.016 ml, 0.18 mmol) were used, and a method similar to that described in Production Example 24 was employed to obtain the title compound (36 mg, 0.088 mmol, yield 55%).

Production Example 39

N-[3-[3-(5,6-Dimethoxy-3-methyl-1,4-benzoquinon-2-ylmethyl)phenyl]acryloyl]isopropylamine 3-[3-(5,6-dimethoxy-3-methyl-1,4-benzoquinon-2-ylmethyl)phenyl]acrylic acid (55 mg, 0.16 mmol) obtained in Production Example 36 and isopropylamine (0.016 ml, 0.18 mmol) were used, and a method similar to that described in Production Example 24 was employed to obtain the title compound (21 mg, 0.055 mmol, yield 34%).

Production Example 40

N-[3-[3-(5,6-Dimethoxy-3-methyl-1,4-benzoquinon-2-ylmethyl)phenyl]acryloyl]thiomorpholine 3-[3-(5,6-dimethoxy-3-methyl-1,4-benzoquinon-2-ylmethyl)phenyl]acrylic acid (55 mg, 0.16 mmol) obtained in Production Example 36 and thiomorpholine (0.018 ml, 0.18 mmol) were used, and a method similar to that described in Production Example 24 was employed to obtain the title compound (32 mg, 0.075 mmol, yield 47%).

Production Example 41

3-(5,6-Dimethoxy-3-methyl-1,4-benzoquinon-2-ylmethyl)benzoic Acid

Step 1. m-Iodobenzoic Acid Methylester m-iodobenzoic acid (1 g, 4.03 mmol) was used, and a method similar to that described in Step 1 of Method B of Production Example 21 was employed to obtain the title compound as a crude product (1.08 g). This was used as a raw material for the subsequent reaction without purification.

NMR (CDCl$_3$): 3.92 (3H, s), 7.18 (1H, m), 7,88 (1H, d, J=8.0 Hz), 8.00 (1H, d, J=7.8 Hz), 8.38 (1H, s); FABMS (m/z): 263 (M+H)$^+$.

Step 2. 3-[Hydroxy-(2,3,4,5-tetramethoxy-6-methylphenyl) methyl]benzoic Acid Methylester Method 1

The compound (1.08 g, 4.1 mmol) obtained in Step 1 was used, and a method similar to that described in Step 2 of Method B of Production Example 21 was employed to obtain the title compound (490 mg, 1.30 mmol, yield 32%).

NMR (CDCl$_3$): 2.26 (3H, s), 3.32 (3H, s), 3.82 (3H, s), 3.86 (3H, s), 3.90 (3H, s), 3.94 (3H, s), 6.02 (1H, d, J=10.6 Hz), 7.39 (1H, m), 7.47 (1H, d, J=7.6 Hz), 7.91 (1H, J=7.4 Hz), 8.04 (1H, s); FABMS (m/z): 376 (M+H)$^+$.

Method 2

A 1.54 M solution of t-butyllithium/pentane and the compound (1.05 g, 4.00 mmol) obtained in Step 1 were used, and a method similar to that described in Step 2 of Method B of Production Example 21 was employed to obtain the title compound (684 mg, 1.28 mmol, yield 32%).

Step 3. 3-(2,3,4,5-Tetramethoxy-6-methylbenzyl)benzoic Acid Methylester

The compound (245 mg, 0.65 mmol) obtained in Step 2 was used, and a method similar to that described in Step 3 of Method B of Production Example 21 was employed to obtain the title compound (170mg, 0.47 mmol, yield 72%).

NMR (CDCl$_3$): 2.08 (3H, s), 3.70 (3H, s), 3.78 (3H, s), 3.89 (3H, s), 3.92 (3H, s), 3.94 (3H, s), 4.05 (2H, s), 7.26–7.32 (2H, m), 7.83 (2H, m); FABMS (m/z): 360 (M+H)$^+$.

Step 4. 3-(2,3,4,5-Tetramethoxy-6-methylbenzyl)benzoic Acid

The compound (170 mg, 0.47 mmol) obtained in Step 3 was used, and a method similar to that described in Step 4 of Method B of Production Example 21 was employed to obtain the title compound (150 mg, 0.43 mmol, yield 91%).

NMR (CDCl$_3$): 2.09 (3H, s), 3.71 (3H, s), 3.79 (3H, s), 3.92 (3H, s), 3.94 (3H, s), 4.06 (2H, s), 7.33 (2H, m), 7.90 (2H, m); FABMS (m/z): 346 (M+H)$^+$.

Step 5. 3-(5,6-Dimethoxy-3-methyl-1,4-benzoquinon-2-ylmethyl)benzoic Acid

The compound (150 mg, 0.43 mmol) obtained in Step 4 was used, and a method similar to that described in Step 5 of Method B of Production Example 21 was employed to obtain the title compound (117 mg, 0.37 mmol, yield 86%).

Production Example 42

N-[3-(5,6-Dimethoxy-3-methyl-1,4-benzoquinon-2-ylmethyl)benzoyl]isopropylamine 3-(5,6-dimethoxy-3-methyl-1,4-benzoquinon-2-ylmethyl)benzoic acid (85 mg, 0.27 mmol) obtained in Production Example 41, isopropylamine (0.035 ml, 0.41 mmol), and 1-ethyl-3-(3-dimethylaminopropyl)carbodiimide hydrochloride (78 mg, 0.41 mmol) in dry methylene chloride (3.4 ml) were stirred at room temperature for 1 hour. The reaction mixture was concentrated under reduced pressure and then was purified by a silica gel column chromatography (methylene chloride:methanol= 20:1) to obtain the title compound (37 mg, 0.10 mmol, yield 37%).

Production Example 43

N-[3-(5,6-Dimethoxy-3-methyl-1,4-benzoquinon-2-ylmethyl)benzoyl]piperidine 3-(5,6-dimethoxy-3-methyl-1,4-benzoquinon-2-ylmethyl)benzoic acid (85 mg, 0.27 mmol) obtained in Production Example 41 and piperidine (0.036 ml, 0.41 mmol) were used, and a method similar to that described in Production Example 42 was employed to obtain the title compound (40 mg, 0.10 mmol, yield 37%).

Production Example 44

N-[3-(5,6-Dimothoxy-3-methyl-1,4-benzoquinon-2-ylmethyl)benzoyl]morpholine 3-(5,6-dimethoxy-3-methyl-1,4-benzoquinon-2-ylmethyl)benzoic acid (85 mg, 0.27 mmol) obtained in Production Example 41 and morpholine (0.036 ml, 0.41 mmol) were used, and a method similar to that described in Production Example 42 was employed to obtain the title compound (57 mg, 0.15 mmol, yield 54%).

Production Example 45

N-[3-(5,6-Dimethoxy-3-methyl-1,4-benzoquinon-2-ylmethyl)benzoyl]thiomorpholine 3-(5,6-dimethoxy-3-methyl-1,4-benzoquinon-2-ylmethyl)benzoic acid (85 mg, 0.27 mmol) obtained in Production Example 41 and thiomorpholine (0.041 ml, 0.41 mmol) were used, and a method similar to that described in Production Example 42 was employed to obtain the title compound (61 mg, 0.15 mmol, yield 54%).

Production Example 46

N-[3-[4-(3,5,6-Trimethyl-1,4-benzoquinon-2-ylmethyl)phenyl]thiomorpholine

3-[4-(3,5,6-trimethyl-1,4-benzoquinon-2-ylmethyl)phenyl]propionic acid (25 mg, 0.08 mmol), isopropylamine (0.010 ml, 0.12 mmol), and 1-ethyl-3-(3-dimethylaminopropyl)carbodiimide hydrochloride (28 mg, 0.12 mmol) in dry methylene chloride (1 ml) were stirred at room temperature for 1 hour. The reaction mixture was concentrated under reduced pressure and was purified by a silica gel column chromatography (methylene chloride ethyl acetate=4:1) to obtain the title compound (18 mg, 0.051 mmol, yield 64%).

Production Example 47

N-[3-[4-(3,5,6-Trimethyl-1,4-benzoquinon-2-ylmethyl)phenyl]propionyl]piperidine

3-[4-(3,5,6-trimethyl-1,4-benzoquinon-2-ylmethyl)phenyl]propionic acid (25 mg, 0.08 mmol) and piperidine (0.012 ml, 0.12 mmol) were used, and a method similar to that described in Production Example 46 was employed to obtain the title compound (53 mg, 0.14 mmol, yield 59%).

Production Example 48

N-[3-[4-(3,5,6-Trimethyl-1,4-benzoquinon-2-ylmethyl)phenyl]propionyl]morpholine

3-[4-(3,5,6-trimethyl-1,4-benzoquinon-2-ylmethyl)phenyl]propionic acid (25 mg, 0.08 mmol) and morpholine (0.010 ml, 0.12 mmol) were used, and a method similar to that described in Production Example 46 was employed to obtain the title compound (21 mg, 0.055 mmol, yield 69%).

Production Example 49

N-[3-[3-(3,5,6-Trimethyl-1,4-benzoquinon-2-ylmethyl)phenyl]propionyl]isopropylamine 3-[3-(5,6-dimethoxy-3-methyl-1,4-benzoquinon-2-ylmethyl)phenyl]propionic acid (30 mg, 0.096 mmol) and isopropylamine (0.010 ml, 0.12 mmol) were used, and a method similar to that described in Production Example 46 was employed to obtain the title compound (14 mg, 0.040 mmol, yield 42%).

Production Example 50

N-[3-[3-(3,5,6-Trimethyl-1,4-benzoquinon-2-ylmethyl)phenyl]propionyl]piperidine

3-[3-(5,6-dimethoxy-3-methyl-1,4-benzoquinon-2-ylmethyl)phenyl]propionic acid (30 mg, 0.096 mmol) and piperidine (0.010 ml, 0.12 mmol) were used, and a method similar to that described in Production Example 46 was employed to obtain the title compound (19 mg, 0.050 mmol, yield 52%).

Production Example 51

N-[3-[3-(3,5,6-Trimethyl-1,4-benzoquinon-2-ylmethyl)phenyl]propionyl]morpholine

3-[3-(5,6-dimethoxy-3-methyl-1,4-benzoquinon-2-ylmethyl)phenyl]propionic acid (30 mg, 0.096 mmol) and morpholine (0.010 ml, 0.12 mmol) were used, and a method similar to that described in Production Example 46 was employed to obtain the title compound (25 mg, 0.066 mmol, yield 69%).

Production Example 52

4-(5,6-Dimethoxy-3-methyl-1,4-benzoquinon-2-ylmethyl)phenylacetic Acid

Step 1. 4-[2,3,4,5-Tetramethoxy-6-methlbenzyl)benzoic Acid Diazomethyl Ketone 4-(2,3,4,5-tetramethoxy-6-methylbenzyl)benzoic acid (700 mg, 2.02 mmol) obtained in Step 2 of Method A of Production Example 21 was used, and a method similar to that described in Step 1 of Method A of Production Example 26 was employed to obtain the title compound (96 mg, 0.26 mmol).

NMR (CDCl$_3$): 2.07 (3H, s), 3.70 (3H, s), 3.79 (3H, s), 3.92 (3H, s), 3.95 (3H, s), 4.05 (2H, s), 5.85 (1H, s), 7.18 (2H, d, J=8.0 Hz), 7.65 (2H, d, J=8.0 Hz); FABMS (m/z): 370 (M)$^+$.

Step 2. 4-(5,6-Dimethoxy-3-methyl-1,4-benzoquinon-2-ylmethyl)phenylacetic Acid

The compound (96 mg, 0.26 mmol) obtained in Step 1 was used, and a method similar to that described in Step 2 of Method A of Production Example 26 was employed to obtain 4-(2,3,4,5-tetramethoxy-6-methylbenzyl)phenylacetic acid as a crude product. This was used without further purification, and a method similar to that described in Step 3 of Method A of Production Example 26 was employed to obtain the title compound (63 mg, 0.19 mmol).

Production Example 53

N-[4-(5,6-Dimethoxy-3-methyl-1,4-benzoquinon-2-ylmethyl)phenylacetyl]morpholine 4-(5,6-dimethoxy-3-methyl-1,4-benzoquinon-2-ylmethyl)benzoic acid (100 mg, 0.32 mmol) obtained in Production Example 21 was used, and a method similar to that described in Step 1 of Method A of Production Example 26 was employed to obtain 4-(5,6-dimethoxy-3-methyl-1,4-benzoquinon-2-ylmethyl)benzoic acid diazomethyl ketone as a crude product. Without further purification, this was dissolved in dry ethanol (5 ml). Silver nitrate (56 mg, 0.33 mmol) and morpholine (0.14 ml, 1.65 mmol) were added thereto and the mixture was heated to reflux for one hour. The resulting residue obtained after the distilling off the solvent was purified by a silica gel column chromatography (hexane:ethyl acetate=1:3 to 1:4) to yield a crude fraction containing the title compound. The fraction was purified again by silica gel column chromatography (methylene chloride:methanol=20:1) to obtain the title compound (9 mg, 0.02 mmol, yield 7%).

Production Example 54

N-[4-(5,6-Dimethoxy-3-methyl-1,4-benzoquinon-2-ylmethyl)phenylacetyl]piperidine 4-(5,6-dimethoxy-3-methyl-1,4-benzoquinon-2-ylmethyl)phenylacetic acid (21 mg, 0.063 mmol) obtained in Production Example 52 and piperidine (0.0094 ml, 0.095 mmol) were used, and a method similar to that described in Production Example 46 was employed to obtain the title compound (7.8 mg, 0.020 mmol, yield 32%).

Production Example 55

N-[4-(5,6-Dimethoxy-3-methyl-1,4-benzoquinon-2-ylmethyl)phenylacetyl]thiomorpholine 4-(5,6-dimethoxy-3-methyl-1,4-benzoquinon-2-ylmethyl)phenylacetic acid (21 mg, 0.063 mmol) obtained in Production Example 52 and thiomorpholine (0.0096 ml, 0.095 mmol) were used, and a method similar to that described in Production Example 46 was employed to obtain the title compound (5.1 mg, 0.012 mmol, yield 19%).

Production Example 56

N-[4-(5,6-Dimethoxy-3-methyl-1,4-benzoquinon-2-ylmethyl)phenylacetyl]isopropylamine 4-(5,6-dimethoxy-3-methyl-1,4-benzoquinon-2-ylmethyl)phenylacetic acid (21 mg, 0.063 mmol) obtained in Production Example 52 and isopropylamine (0.008 ml, 0.095 mmol) were used, and a method similar to that described in Production Example 46 was employed to obtain the title compound (5.1 mg, 0.014 mmol, yield 22%).

Production Example 57

3-(5,6-Dimethoxy-3-methyl-1,4-benzoquinon-2-ylmethyl)phenylacetic Acid

Step 1. 3-(2,3,4,5-Tetramethoxy-6-methylbenzyl)benzoic Acid Diazomethyl Ketone 3-(2,3,4,5-tetramethoxy-6-methylbenzyl)benzoic acid (560 mg, 1.6 mmol) obtained in Step 4 of Production Example 41 was used, and a method similar to that described in Step 1 of Method A of Production Example 26 was employed to obtain the title compound (410 mg, 1.1 mmol, yield 69%).

NMR (CDCl$_3$): 2.08 (3H, s), 3.71 (3H, s), 3.78 (3H, s), 3.93 (3H, s), 3.94 (3H, s), 4.05 (2H, s), 5.84 (1H, s), 7.26 (1H, m), 7.32 (1H, m), 7.53 (1H, m), 7.58 (1H, m); FABMS (m/z): 370 (M)$^+$.

Step 2. 3-(2,3,4,5-Tetramethoxy-6-methylbenzyl)phenylacetic Acid

The compound (410 mg, 1.11 mmol) obtained in Step 1 was used, and a method similar to that described in Step 2 of Method A of Production Example 26 was employed to obtain the title compound (370 mg, 1.03 mmol, yield 93%).

NMR (CDCl$_3$): 2.08 (3H, s), 3.60 (2H, s), 3.68 (3H, s), 3.78 (3H, s), 3.92 (3H, s), 3.94 (3H, s), 4.00 (2H, s), 6.99–7.09 (3H, m), 7.21 (1H, m); FABMS (m/z): 360 (M)$^+$.

Step 3. 3-(5,6-Dimethoxy-3-methyl-1,4-benzoquinon-2-ylmethyl)phenylacetic Acid

The compound (370 mg, 1.03 mmol) obtained in Step 2 was used, and a method similar to that described in Step 3 of Method A of Production Example 26 was employed to obtain the title compound (330 mg, 1.00 mmol, yield 97%).

Production Example 58

N-[3-(5,6-Dimethoxy-3-methyl-1,4-benzoquinon-2-ylmethyl)phenylacetyl]piperidine 3-(5,6-dimethoxy-3-methyl-1,4-benzoquinon-2-ylmethyl)phenylacetic acid (90 mg, 0.27 mmol) obtained in Production Example 57 and piperidine (0.040 ml, 0.41 mmol) were used, and a method similar to that described in Production Example 46 was employed to obtain the title compound (35 mg, 0.088 mmol, yield 33%).

Production Example 59

N-[3-(5,6-Dimethoxy-3-methyl-1,4-benzoquinon-2-ylmethyl)phenylacetyl]thiomorpholine 3-(5,6-dimethoxy-3-methyl-1,4-benzoquinon-2-ylmethyl)phenylacetic acid (90 mg, 0.27 mmol) obtained in Production Example 57 and thiomorpholine (0.040 ml, 0.41 mmol) were used, and a method similar to that described in Production Example 46 was employed to obtain the title compound (47 mg, 0.11 mmol, yield 41%).

Production Example 60

N-[3-(5,6-Dimethoxy-3-methyl-1,4-benzoquinon-2-ylmethyl)phenylacetyl]morpholine 3-(5,6-dimethoxy-3-methyl-1,4-benzoquinon-2-ylmethyl)phenylacetic acid (90 mg, 0.27 mmol) obtained in Production Example 57 and morpholine (0.035 ml, 0.41 mmol) were used, and a method similar to that described in Production Example 46 was employed to obtain the title compound (41 mg, 0.10 mmol, yield 37%).

Production Example 61

N-[3-(5,6-Dimethoxy-3-methyl-1,4-benzoquinon-2-ylmethyl)phenylacetyl]isopropylamine 3-(5,6-dimethoxy-3-methyl-1,4-benzoquinon-2-ylmethyl)phenylacetic acid (90 mg, 0.27 mmol) obtained in Production Example 57 and isopropylamine (0.035 ml, 0.41 mmol) were used, and a method similar to that described in Production Example 46 was employed to obtain the title compound (43 mg, 0.12 mmol, yield 44%).

Production Example 62

4-[3-(5,6-Dimethoxy-3-methyl-1,4-benzoquinon-2-ylmethyl]phenyl-n-butyric Acid

Step 1. 3-[3-(2,3,4,5-Tetramethoxy-6-methylbenzyl)phenyl] propionic Acid Diazomethyl Ketone 3-[3-(2,3,4,5-tetramethoxy-6-methylbenzyl)phenyl] propionic acid (500 mg, 1.34 mmol) obtained as an intermediate in the synthesis of the compound of Production Example 31 was used, and a method similar to that described in Step 1 of Method A of Production Example 26 was employed to obtain the title compound (330 mg, 0.83 mmol, yield 62%).

NMR (CDCl$_3$): 2.07 (3H, s), 2.58 (2K, broad), 2.89 (2H, m), 3.65 (3H, s), 3.78 (3H, s), 3.93 (31i, s), 3.94 (3H, s), 3.98 (2H, s), 5.17 (1H, broad), 6.91–6.99 (3H, m), 7.16 (1H, m); FABMS (m/z): 398 (M)$^+$.

Step 2. 4-[3-(2,3,4,5-Tetramethoxy-6-methylbenzyl) phenyl]-n-butyric Acid

The compound (330 mg, 0.83 mmol) obtained in Step 1 was used, and a method similar to that described in Step 2 of Method A of Production Example 26 was employed to obtain the title compound (320 mg, 0.83 mmol, yield 10.0%).

NMR (CDCl$_3$): 1.93 (2H, m), 2.08 (3H, s), 2.35 (2H, m), 2.62 (2H, m), 3.69 (3H, s), 3.78 (3H, s), 3.92 (3H, s), 3.94 (3H, s), 3.99 (2H, s), 6.91 6.98 (3H, m), 7.16 (1H, m); FABMS (m/z): 388 (M)$^+$.

Step 3. 4-[3-(5,6-Dimethoxy-3-methyl-1,4-benzoquinon-2-ylmethyl)phenyl]-n-butyric Acid The compound (330 mg, 0.85 mmol) obtained in Step 2 was used, and a method similar to that described in Step 3 of Method A of Production Example 26 was employed to obtain the title compound (290 mg, 0.81 mmol, yield 98%).

Production Example 63

N-[4-[3-(5,6-Dimethoxy-3-methyl-1,4-benzoquinon-2-ylmethyl)phenyl]butanoyl]piperidine 4-[3-(5,6-dimethoxy-3-methyl-1,4-benzoquinon-2-ylmethyl)phenyl]-n-butyric acid (73 mg, 0.20 mmol) obtained in Production Example 62 and piperidine (0.030 ml, 0.30 mmol) were used, and a method similar to that described in Production Example 46 was employed to obtain the title compound (16 mg, 0.038 mmol, yield 19%).

Production Example 64

N-[4-[3-(5,6-Dimethoxy-3-methyl-1,4-benzoquinon-2-ylmethyl)phenyl]butanoyl]thiomorpholine 4-[3-(5,6-dimethoxy-3-methyl-1,4-benzoquinon-2 ylmethyl)phenyl]-n-butyric acid (73 mg, 0.20 mmol) obtained in Production Example 62 and thiomorpholine (0.030 ml, 0.30 mmol) were used, and a method similar to that described in Production Example 46 was employed to obtain the title compound (26 mg, 0.059 mmol, yield 29%).

Production Example 65

N-[4-[3-(5,6-Dimethoxy-3-methyl-1,4-benzoquinon-2-ylmethyl)phenyl]butanoyl]morpholine 4-[3-(5,6-dimethoxy-3-methyl-1,4-benzoquinon-2-ylmethyl)phenyl]-n-butyric acid (73 mg, 0.20 mmol) obtained in Production Example 62 and morpholine (0.026 ml, 0.30 mmol) were used, and a method similar to that described in Production Example 46 was employed to obtain the title compound (28 mg, 0.066 mmol, yield 33%).

Production Example 66

N-[4-[3-(5,6-Dimethoxy-3-methyl-1,4-benzoquinon-2-ylmethyl)phenyl]butanoyl]isopropylamine 4-[3-(5,6-dimethoxy-3-methyl-1,4-benzoquinon-2-ylmethyl)phenyl]-n-butyric acid (73 mg, 0.20 mmol) obtained in Production Example 62 and isopropylamine (0.019 ml, 0.30 mmol) were used, and a method similar to that described in Production Example 46 was employed to obtain the title compound (17 mg, 0.043 mmol, yield 21%).

Production Example 67

3-[2-(5,6-Dimethoxy-3-methyl-1,4-benzoquinon-2-ylmethyl)phenyl]acrylic Acid

Step 1. 2-[2-[Hydroxy-(2,3,4,5-tetramethoxy-6-methylphenyl)methyl]phenyl]-1,3-dioxolane 2-(2-bromophenyl)-1,3-dioxolane (2.03 g, 8.90 mmol) was used, and a method similar to that described in Step 1 of Production Example 1 was employed to obtain the title compound (1.64 g, 4.20 mmol, yield 47%).

NMR (CDCl$_3$): 2.14 (3H, s), 3.64 (3H, s), 3.79 (3H, s), 3.90 (3H, s), 3.96 (3H, s), 4.08–4.19 (2H, m), 4.43 (1H, d, J=8.8 Hz), 6.37 (1H, s), 6.46 (1H, d, J=8.8 Hz), 6.97 (1H, d, J=7.6 Hz), 7.24–7.30 (2H, m), 7.70 (1H, d, J=7.6 Hz); FABMS (m/z): 390 (M+H)$^+$.

Step 2. 2-[2-[Acetoxy-(2,3,4,5-tetramethoxy-6-methylphenyl)methyl]benzaldehyde

The compound (640 mg, 1.64 mmol) obtained in Step 1 was used, and a method similar to that described in Step 2 of Production Example 1 was employed to obtain the title compound (590 mg, 1.51 mmol, yield 92%).

NMR (CDCl$_3$): 2.15 (3H, s), 2.17 (3H, s), 3.64 (3H, s), 3.79 (3H, s), 3.87 (3H, s), 3.95 (3H, s), 7.33 (1H, d, J=7.7 Hz), 7.45 (1H, m), 7.53 (1H, m), 7.88 (1H, m), 7.94 (1H, s), 10.20 (1H, s); FABMS (m/z): 388 (M+H)$^+$.

Step 3. 3-[2-[Acetoxy-(2,3,4,5-tetramethoxy-6-methylphenyl)methyl]phenyl]acrylic Acid Ethylester The compound (590 mg, 1.51 mmol) obtained in Step 2 was used, and a method similar to that described in Step 3 of Production Example 1 was employed to obtain the title compound (490 mg, 1.07 mmol, yield 71%).

NMR (CDCl$_3$): 1.32 (3H, s), 2.15 (3H, s), 2.21 (3H, s), 3.58 (3H, s), 3.78 (3H, s), 3.86 (3H, s), 3.94 (3H, s), 4.22 (2H, m), 6.19 (1H, d, J=15.7 HZ), 7.24–7.33 (2H, m), 7.49 (1H, m), 7.60 (1H, s), 7.80 (1H, d, J=15.7 Hz); FABMS (M/z): 458 (M+H)$^+$.

Step 4. 3-[2-(6-Methyl-2,3,4,5-tetramethoxybenzyl)phenyl Acid Ethylester

The compound (490 mg, 1.07 mmol) obtained in Step 3 was used, and a method similar to that described in Step 4 of Production Example 1 was employed to obtain the title compound (230 mg, 0.58 mmol, yield 54%).

NMR (CDCl$_3$): 1.36 (3H, m), 2.00 (3H, a), 3.64 (3H, s), 3.80 (3H, s), 3.92 (3H, s), 3.96 (3H, s), 4.11 (2H, s), 4.29 (2H, m), 6.40 (1H, d, J=15.8 Hz), 6.71 (1H, broad), 7.19 (2H, m), 7.59 (1H, m), 8.22 (1H, d, J=15.8 Hz); FABMS (m/z): 400 (M+H)$^+$.

Step 5. 3-[2-(6-Methyl-2,3,4,5-tetramethoxybenzyl)phenyl] acrylic Acid

The compound (137 mg, 0.34 mmol) obtained in Step 4 was used, and a method similar to that described in Step 1 of Production Example 2 was employed to obtain the title compound (71 mg, 0.19 mmol, yield 56%).

NMR (CDCl$_3$): 2.02 (3H, s), 3.64 (3H, s), 3.80 (3H, s), 3.92 (3H, s), 3.96 (3H, s), 4.12 (2H, s), 6.42 (1H, d, J=15.8 Hz), 6.75 (1H, m), 7.21–7.25 (2H, m), 7.60 (1H, m), 8.32 (1H, d, J=15.8 Hz); FABMS (m/z): 372 (M+H)$^+$.

Step 6. 3-[2-(5,6-Dimethoxy-3-methyl-1,4-benzoquinon-2-ylmethyl)phenyl]acrylic Acid The compound (71 mg, 0.34 mmol) obtained in Step 5 was used, and a method similar to that described in Step 2 of Production Example 2 was employed to obtain the title compound (23 mg, 0.067 mmol, yield 35%).

Production Example 68

N-[3-[2-(5,6-Dimethoxy-3-methyl-1,4-benzoquinon-2-ylmethyl)phenyl]acryloyl]thiomorpholine 3-[2-(5,6-dimethoxy-3-methyl-1,4-benzoquinon-2-ylmethyl)phenyl]acrylic acid (20 mg, 0.058 mmol) obtained in Production Example 67 and thiomorpholine (0.009 ml, 0.087 mmol) were used, and a method similar to that described in Production Example 46 was employed to obtain the title compound (10 mg, 0.023 mmol, yield 40%).

Production Example 69

3-[2-(5,6-Dimethoxy-3-methyl-1,4-benzoquinon-2-ylmethyl)phenyl]propionic Acid

Step 1. 3-[2-(6-Methyl-2,3,4,5-tetramethoxybenzyl)phenyl] propionic Acid Ethylester 3-(2-(6-methyl-2,3,4,5-tetramethoxybenzyl)phenyl] acrylic acid ethylester (85 mg, 0.21 mmol) obtained in Step 4 of Production Example 67 was used, and a method similar to that described in Step 5 of Production Example 1 was employed to obtain the title compound (80 mg, 0.20 mmol, yield 95%).

NMR (CDCl$_3$): 1.27 (3H, m), 2.03 (3H, s), 2.66 (2H, m), 3.11 (2H, m), 3.61 (3H, m), 3.81 (3H, s), 3.92 (3H, s), 3.96 (3H, s), 3.98 (2H, s), 4.17 (2H, m), 6.63 (1H, d, J=7.6 Hz), 7.04 (1H, m), 7.11 (1H, m), 7.18 (1H, m); FABMS (m/z): 402 (M+H)$^+$.

Step 2. 3-[2-(6-Methyl-2,3,4,5-tetramethoxybenzyl)phenyl] propionic Acid

The compound (80 mg, 0.20 mmol) obtained in Step 1 was used, and a method similar to that described in Step 6 of Production Example 1 was employed to obtain the title compound (63 mg, 0.17 mmol, yield 85%).

NMR (CDCl$_3$): 2.03 (3H, s), 2.75 (2H, m), 3.12 (2H, m), 3.61 (3H, s), 3.81 (3H, s), 3.91 (3H, s), 3.96 (3H, s), 3.98 (2H, s), 6.65 (1H, d, J=7.6 Hz), 7.06 (1H, m), 7.13 (1H, m), 7.20 (1H, d, J=7.2 Hz); FABMS (m/z): 374 (M+H)$^+$.

Step 3. 3-[2-(5,6-Dimethoxy-3-methyl-1,4-benzoquinon-2-ylmethyl)phenyl]propionic Acid The compound (63 mg, 0.17 mmol) obtained in Step 2 was used, and a method similar to that described in Step 7 of Production Example 1 was employed to obtain the title compound (50 mg, 0.15 mmol, yield 88%).

Production Example 70

N-[3-[2-(5,6-Dimethoxy-3-methyl-1,4-benzoquinon-2-ylmethyl)phenyl]propionyl]piperidine 3-(2-(5,6-dimethoxy-3-methyl-1,4-benzoquinon-2-ylmethyl)phenyl]propionic acid (20 mg, 0.058 mmol) obtained in Production Example 69 and piperidine (0.009 ml, 0,087 mmol) were used, and a method similar to that described in Production Example 46 was employed to obtain the title compound (8.4 mg, 0.020 mmol, yield 34%).

Production Example 71

N-[3-[2-(5,6-Dimethoxy-3-methyl-1,4-benzoquinon-2-ylmethyl)phenyl]propionyl]morpholine 3-[2-(5,6-dimethoxy-3-methyl-1,4-benzoquinon-2-ylmethyl)phenyl]propionic acid (25 mg, 0.070 mmol) obtained in Production Example 69 and morpholine (0.009 ml, 0.11 mmol) were used, and a method similar to that described in Production Example 46 was employed to obtain the title compound (10 mg, 0.024 mmol, yield 34%).

Production Example 72

N-[3-[2-(5,6-dimethoxy-3-methyl-1,4-benzoquinon-2-ylmethyl)phenyl]propionyl]thiomorpholine 3-[2-(5,6-dimethoxy-3-methyl-1,4-benzoquinon-2-ylmethyl)phenyl]propionic acid (25 mg, 0.070 mmol) obtained in Production Example 69 and thiomorpholine (0.011 ml, 0.11 mmol) were used, and a method similar to that described in Production Example 46 was employed to obtain the title compound (10 mg, 0.024 mmol, yield 34%).

Production Example 73

N-[3-[2-(5,6-Dimethoxy-3-methyl-1,4-benzoquinon-2-ylmethyl)phenyl]propionyl]isopropylamine 3-[2-(5,6-dimethoxy-3-methyl-1,4-benzoquinon-2-ylmethyl)phenyl]propionic acid (15 mg, 0.044 mmol) obtained in Production Example 69 and isopropylamine (0.005 ml, 0.066 mmol) were used, and a method similar to that described in Production Example 46 was employed to obtain the title compound (4.7 mg, 0.012 mmol, yield Production Example 74 to 189

The compounds of Production Example 74 to 189 were prepared using a synthesizer (MORITEX Corp.) in the following method:

To a solution of 3-(4-(5,6-dimethoxy-3-methyl-1,4-benzoquinon-2-ylmethyl)phenyl]propionic acid (100 mg, 30 mmol) obtained in Production Example 1 in dry methylene chloride (0.3 ml) were sequentially added triethylamine (0.2 ml, 1.40 mmol), a solution of an amine (0.4 mmol) in methylene chloride (0.6 ml) and propane phosphonic acid anhydride (a 25% solution in ethyl acetate, 0.6 ml), and the mixture was stirred at 25° C. for 1 to 2 hours. Water was added to the reaction mixture, extracted with ethyl acetate, and after drying the solvent was distilled off. The resulting residue was purified by a silica gel column chromatography (methylene chloride—methanol) to yield the desired compound.

| Production Example No. | Structure | Property (Melting point °C.) | FABMS (m/z) | NMR(CDCl$_3$, δ) |
| --- | --- | --- | --- | --- |
| 1 | 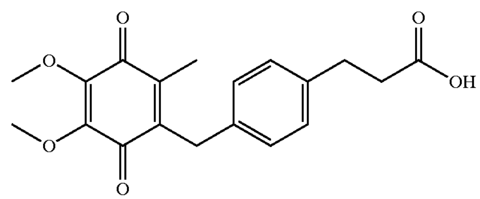 | Crystal (139–141) | 344(M)$^+$(EIMS) | 2.09(3H, s), 2.62(2H, m), 2.89(2H, m), 3.80(2H, s), 3.99(6H, s), 6.95–7.30(4H, m) |
| 2 | 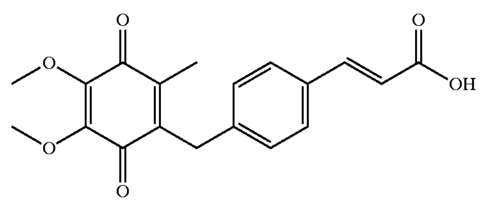 | Crystal (203–205) | 343(M + H)$^+$ | 2.09(3H, s), 3.87(2H, s), 4.00(6H, s), 6.39(1H, d), 7.22(2H, d), 7.47(2H, d), 7.73(1H, d) |
| 3 | 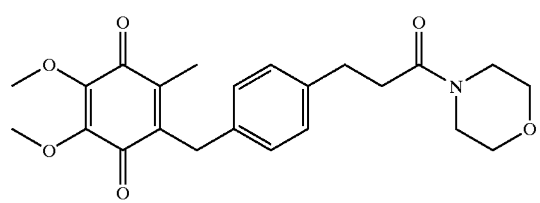 | Crystal (65–67) | 414(M + H)$^+$ | 2.08(3H, s), 2.57(2H, m), 2.93(2H, m), 3.30–3.40(2H, m), 3.45–3.55(2H, m), 3.55–3.65(4H, m), 3.81(2H, s), 3.98(3H, s), 3.99(3H, s), 7.10(4H, s) |
| 4 | 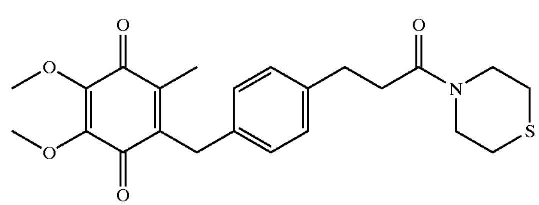 | Crystal (65–67) | 429(M)$^+$(EIMS) | 2.09(3H, s), 2.25–2.65(4H, m), 2.57(2H, m), 2.91(2H, m), 3.55–4.95(2H, m), 3.81(2H, s), 3.99(6H, s), 7.12(4H, s) |

-continued
| | | | | |
|---|---|---|---|---|
| 5 | 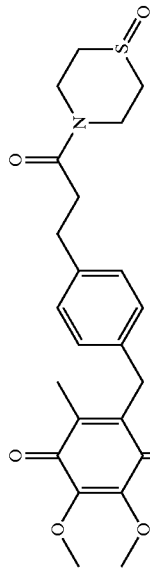 | Crystal (114–116) | 446(M + H)⁺ | 2.09(3H, s), 2.10–2.20(1H, m), 2.50–2.70(4H, m), 2.70–2.85(1H, m), 2.85–3.00(2H, m), 3.60–3.80(2H, m), 3.80(2H, s), 3.98(3H, s), 3.99(3H, s), 3.95–4.10(1H, m), 4.40–4.55(1H, m), 7.12(4H, s) |
| 6 | 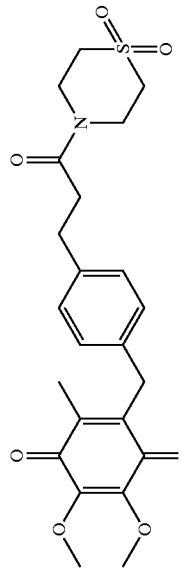 | Crystal (104–105) | 462(M + H)⁺ | 2.10(3H, s), 2.50–2.70(4H, m), 2.85–3.00(4H, m), 3.70–3.90(4H, m), 3.98(3H, s), 3.99(3H, s), 4.00–4.15(2H, m), 7.00–7.20(4H, m) |
| 7 | 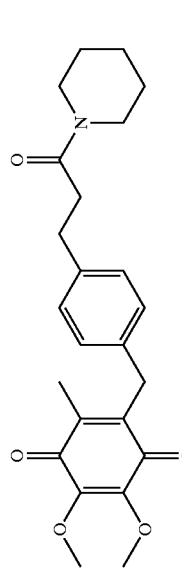 | Crystal (63–64) | 412(M + H)⁺ | 1.52(6H, m), 2.07(3H, s), 2.56(2H, m), 2.91(2H, m), 3.32(2H, m), 3.54(2H, m), 3.80(2H, s), 3.98(3H, s), 3.99(3H, s), 7.10(4H, m) |
| 8 | 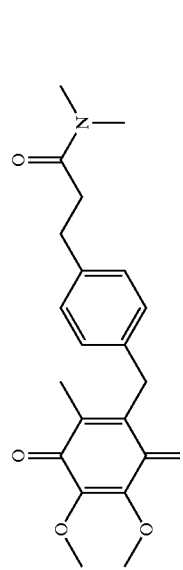 | Oil | 372(M + H)⁺ | 2.07(3H, s), 2.57(2H, m), 2.91(2H, m), 2.92(3H, s), 2.94(3H, s), 3.81(2H, s), 3.98(3H, s), 3.99(3H, s), 7.10(4H, m) |
| 9 | 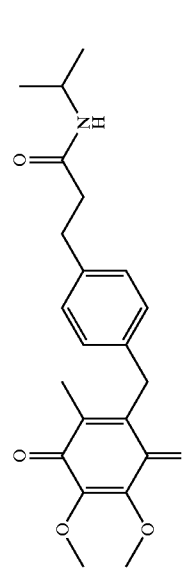 | Crystal (114–116) | 386(M + H)⁺ | 1.06(6H, d), 2.07(3H, s), 2.37(2H, m), 2.90(2H, m), 3.80(2H, s), 3.98(3H, s), 3.99(3H, s), 4.00(1H, m), 5.05(1H, broad), 7.09(4H, m) |

| | | | | |
|---|---|---|---|---|
| 10 | [structure: dimethoxy methylbenzoquinone-CH2-phenyl-CH2CH2-C(O)NH-CH2CH2OH] | Crystal (97–98) | 388(M + H)+ | 2.08(3H, s), 2.45(2H, m), 2.92(2H, m), 3.33(2H, m), 3.59(2H, m), 3.80(2H, s), 3.98(6H, s), 5.67(1H, broad), 7.10(4H, m) |
| 11 | [structure: amide with N-benzyl] | Crystal (119–121) | 434(M + H)+ | 2.06(3H, s), 2.47(2H, m), 2.94(2H, m), 3.80(2H, s), 3.98(6H, s), 4.40(2H, d, J=5.7 Hz), 5.55(1H, broad), 7.08(4H, s), 7.17(2H, m), 7.28(3H, m) |
| 12 | [structure: amide with N-phenethyl] | Crystal (118–119) | 448(M + H)+ | 2.06(3H, s), 2.37(2H, m), 2.72(2H, m), 2.88(2H, m), 3.47(2H, m), 3.80(2H, s), 3.96(6H, s), 3.97(3H, s), 5.27(1H, broad), 7.08(6H, m), 7.20–7.29(3H, m) |
| 13 | [structure: morpholine amide cinnamoyl] | Crystal (124–125) | 412(M + H)+ | 2.08(3H, s), 3.17(8H, m), 3.85(2H, s), 3.99(6H, s), 6.77(1H, d, J=15.4 Hz), 7.18(2H, m), 7.41(2H, m), 7.64(1H, d, J=15.4 Hz) |
| 14 | [structure: thiomorpholine amide cinnamoyl] | Crystal (120–121) | 428(M + H)+ | 2.08(3H, s), 2.66(4H, m), 3.85(2H, s), 3.99(6H, s), 6.77(1H, d, J=15.4 Hz), 7.18(2H, m), 7.41(2H, m), 7.61(1H, d, J=15.4 Hz) |

| | Structure | | NMR |
|---|---|---|---|
| 15 | [quinone with methyl, methoxy, methoxy substituents; benzyl linker to phenyl; CH=CH-C(=O)-N(piperidine)] | Crystal (162–163) 410(M + H)⁺ | 1.50–1.75(6H, m), 2.08(3H, s), 3.45–3.75(4H, m), 3.85(2H, s), 3.99(6H, s), 6.84(1H, d, J=15.4 Hz), 7.17(2H, m), 7.41(2H, m), 7.59(1H, d, J=15.4 Hz) |
| 16 | [quinone ... CH=CH-C(=O)-N(CH$_3$)$_2$] | Crystal (93–94) 370(M + H)⁺ | 2.08(3H, s), 3.06(3H, s), 3.15(3H, s), 3.85(2H, s), 3.99(6H, s), 6.38(1H, d, J=15.4 Hz), 7.18(2H, m), 7.42(2H, m), 7.61(1H, d, J=15.4 Hz) |
| 17 | [quinone ... CH=CH-C(=O)-NH-iPr] | Crystal (118–119) 384(M + H)⁺ | 1.22(6H, d, J=6.5 Hz) 2.08(3H, s), 3.99(6H, s), 4.21 (1H, m),5.35(1H, broad d), 6.28(1H, d, J=15.6 Hz), 7.39(2H, m), 7.55(1H, d, J=15.8 Hz) |
| 18 | [quinone ... CH=CH-C(=O)-NH-CH$_2$CH$_2$OH] | Crystal (114–115) 386(M + H)⁺ | 2.08(3H, s), 2.51(1H, broad), 3.55(2H, m), 3.80(2H, m), 3.85(2H, s), 3.98(6H, s), 6.02(1H, broad), 6.36(1H, d, J=15.6 Hz), 7.18(2H, m), 7.40(2H, m), 7.59(1H, d, J=15.6 Hz) |
| 19 | [quinone ... CH=CH-C(=O)-NH-CH$_2$-phenyl] | Crystal (124–125) 432(M + H)⁺ | 2.08(3H, s), 3.85(2H, s), 3.99(6H, s), 4.57(2H, d, J=5.7 Hz), 5.82(1H, m), 6.34(1H, d, J=15.6 Hz), 7.17(2H, m), 7.28–7.36(5H, m), 7.39(2H, m), 7.62(1H, d, J=15.6 Hz) |

-continued
| | Structure | Form (mp °C) | MS | NMR |
|---|---|---|---|---|
| 20 | 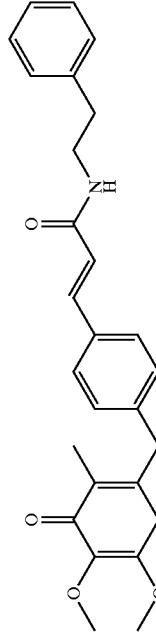 | Crystal (141–142) | 446(M + H)⁺ | 2.08(3H, s), 2.88(2H, m), 3.65(2H, m), 3.84(2H, s), 3.99(6H, s), 5.54(1H, broad), 6.25(1H, d, J=15.6 Hz), 7.16(2H, m), 7.22(3H, m), 7.32(2H, m), 7.38(2H, m), 7.55(1H, d, J=15.6 Hz) |
| 21 | 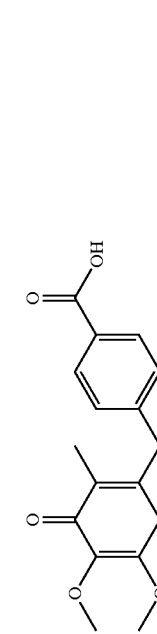 | Powder | 317(M + H)⁺ | 2.08(3H, s), 3.91(3H, s), 4.00(3H, s), 4.00(3H, s), 7.27(2H, m), 7.99(2H, m) |
| 22 | 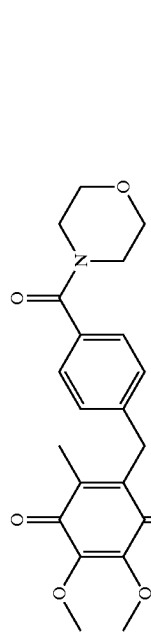 | Oil | 386(M + H)⁺ | 2.08(3H, s), 3.68(8H, broad), 3.86(2H, s), 4.00(6H, s), 7.22(2H, m), 7.31(2H, m) |
| 23 | 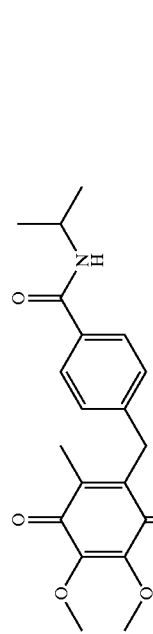 | Oil | 358(M + H)⁺ | 1.25(6H, d, J=6.6 Hz), 2.07(3H, s), 3.88(2H, s), 3.98(3H, s), 3.99(3H, s), 4.27(1H, m), 5.82(1H, broad d), 7.22(2H, m), 7.65(2H, m) |
| 24 | 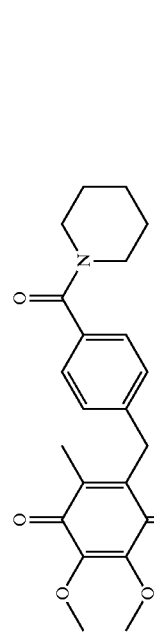 | Oil | 384(M + H)⁺ | 1.54–1.66(6H, m), 2.08(3H, s), 3.49–3.68(4H, broad), 3.86(2H, s), 4.00(6H, s), 7.19(2H, s), 7.29(2H, m) |

| # | Structure | State | MS | NMR |
|---|---|---|---|---|
| 25 | thiomorpholine amide on benzyl trimethoxy quinone | Oil | 402(M+H)+ | 2.08(3H, s), 2.64(4H, broad), 3.60–4.10(4H, broad), 3.86(2H, s), 4.00(6H, s), 7.21(2H, s), 7.28(2H, m) |
| 26 | carboxylic acid propyl on benzyl trimethoxy quinone | Oil | 359(M+H)+ | 1.92(2H, m), 2.08(3H, s), 2.34(2H, m), 2.61(2H, m), 3.80(2H, s), 3.98(3H, s), 3.98(3H, s), 7.08(4H, m) |
| 27 | morpholine amide butyl on benzyl trimethoxy quinone | Oil | 428(M+H)+ | 1.94(2H, m), 2.08(3H, s), 2.28(2H, m), 2.62(2H, m), 3.37(2H, s), 3.62(6H, m), 3.81(2H, s), 3.98(3H, s), 3.99(3H, s), 7.08(4H, s) |
| 28 | thiomorpholine amide butyl on benzyl trimethoxy quinone | Oil | 444(M+H)+ | 1.93(2H, m), 2.08(3H, s), 2.28(2H, m), 2.54–2.64(6H, m), 3.64(2H, m), 3.81(2H, s), 3.86(2H, m), 3.98(3H, s), 3.99(3H, s), 7.08(4H, m) |
| 29 | piperidine amide butyl on benzyl trimethoxy quinone | Oil | 426(M+H)+ | 1.51–1.62(6H, m), 1.92(2H, m), 2.08(3H, s), 2.22(2H, m), 2.72(2H, m), 3.31(2H, m), 3.53(2H, m), 3.81(2H, s), 3.98(3H, s), 3.99(3H, s), 7.08(4H, m) |

-continued

| # | Structure | Form | MS | NMR |
|---|---|---|---|---|
| 30 | (quinone with methyl, two methoxy, benzyl-C6H4-(CH2)3-C(O)NH-iPr) | Powder | 400(M + H)$^+$ | 1.13(6H, d, J=6.6 Hz), 1.92(2H, m), 2.08(3H, s), 2.10(2H, m), 2.59(2H, m), 3.81(2H, s), 3.98(3H, s), 3.99(3H, s), 4.08(1H, m), 5.15(1H, broad), 7.08(4H, m) |
| 31 | (quinone-benzyl-C6H4-CH2CH2-COOH) | Crystal (119–121) | 345(M + H)$^+$ | 2.08(3H, s), 2.64(2H, m), 2.90(2H, m), 3.84(2H, s), 3.98(6H, s), 6.90–7.30(4H, m) |
| 32 | (quinone-benzyl-C6H4-CH2CH2-C(O)-piperidine) | Oil | 412(M + H)$^+$ | 1.46–1.61(6H, m), 2.08(3H, s), 2.58(2H, m), 2.91(2H, m), 3.32(2H, m), 3.55(2H, m), 3.82(2H, s), 3.99(3H, s), 4.00(3H, s), 6.98–7.06(3H, m), 7.20(1H, m) |
| 33 | (quinone-benzyl-C6H4-CH2CH2-C(O)-thiomorpholine) | Oil | 430(M + H)$^+$ | 2.08(3H, s), 2.48(2H, m), 2.55–2.60(4H, m), 2.92(2H, m), 3.66(2H, m), 3.82(2H, s), 3.88(2H, m), 3.99(3H, s), 4.00(3H, s), 7.00–7.05(3H, m), 7.19(1H, m) |
| 34 | (quinone-benzyl-C6H4-CH2CH2-C(O)-morpholine) | Oil | 414(M + H)$^+$ | 2.08(3H, s), 2.58(2H, m), 2.93(2H, m), 3.36(2H, m), 3.52–3.63(6H, m), 3.82(2H, s), 3.99(3H, s), 4.00(3H, s), 6.99–7.05(3H, m), 7.19(1H, m) |

| | | | |
|---|---|---|---|
| 35 | [structure] | Oil | 386(M + H)⁺ | 1.07(6H, d, J=6.5 Hz), 2.07(3H, s), 2.38(2H, m), 2.90(2H, m), 3.81(2H, s), 3.99(3H, s), 4.00(3H, s), 4.03(1H, m), 5.13(1H, broad d), 8.98–7.04(3H, m), 7.17(1H, m) |
| 36 | [structure] | Powder | 343(M + H)⁺ | 2.11(3H, s), 3.89(2H, s), 4.00(6H, s), 6.42(1H, d, J=15.4 Hz), 7.15–7.50(4H, m), 7.73(1H, d, J=15.4 Hz) |
| 37 | [structure] | Oil | 410(M + H)⁺ | 1.61–1.71(6H, m), 2.09(3H, s), 3.57–3.66(4H, broad), 3.86(2H, s), 4.00(8H, s), 6.86(1H, d, J=15.4 Hz), 7.13–7.39(4H, m), 7.57(1H, d, J=15.4 Hz) |
| 38 | [structure] | Oil | 412(M + H)⁺ | 2.09(3H, s), 3.73(8H, broad), 3.86(2H, s), 4.00(6H, s), 6.80(1H, d, J=15.4 Hz), 7.15–7.37(4H, m), 7.63(1H, d, J=15.4 Hz) |
| 39 | [structure] | Oil | 384(M + H)⁺ | 1.22(6H, d, J=6.6 Hz), 2.09(3H, s), 3.84(2H, s), 3.99(3H, s), 4.00(3H, s), 4.21(1H, m), 5.42(1H, broad d), 6.31(1H, d, J=15.4 Hz), 7.15–7.33(4H, m), 7.54(1H, d, J=15.4 Hz) |

| | Structure | Form | MS | NMR |
|---|---|---|---|---|
| 40 | (quinone with methyl, two methoxy, benzyl-phenyl-CH=CH-C(O)-thiomorpholine) | Oil | 428(M + H)⁺ | 2.09(3H, s), 2.68(4H, m), 3.86(2H, s), 3.94(4H, broad), 4.00(6H, s), 6.80(1H, d, J=15.4 Hz), 7.14–7.37(4H, m), 7.60(1H, d, J=15.4 Hz) |
| 41 | (quinone with methyl, two methoxy, benzyl-phenyl-COOH) | Powder | 317(M + H)⁺ | 2.08(3H, s), 3.88(2H, s), 3.99(6H, s), 7.35–7.40(2H, m), 7.89–7.93(2H, m) |
| 42 | (quinone with methyl, two methoxy, benzyl-phenyl-C(O)NH-iPr) | Oil | 358(M + H)⁺ | 1.25(3H, s), 1.27(3H, s), 2.09(3H, s), 3.88(2H, s), 3.99(3H, s), 4.00(3H, s) 4.27(1H, m), 5.85(1H, broad), 7.26–7.33(2H, m), 7.51(1H, d, J=7.1 Hz) |
| 43 | (quinone with methyl, two methoxy, benzyl-phenyl-C(O)-piperidine) | Powder | 384(M + H)⁺ | 1.50(2H, broad), 1.67(4H, broad), 2.08(3H, s), 3.30(2H, broad), 3.70(2H, broad), 3.86(2H, s), 3.99(3H, s), 4.00(3H, s), 7.20(3H, m), 7.29(1H, m) |
| 44 | (quinone with methyl, two methoxy, benzyl-phenyl-C(O)-morpholine) | Oil | 386(M + H)⁺ | 2.08(3H, s), 3.47–3.82(8H, broad), 3.86(2H, s), 3.99(6H, s), 7.21–7.33(4H, m) |

-continued

| | Structure | Form | MS | NMR |
|---|---|---|---|---|
| 45 | (dimethoxy-methyl-benzoquinone-CH2-phenyl-C(O)-thiomorpholine) | Oil | 402(M + H)+ | 2.08(3H, s), 2.61–2.65(4H, broad), 3.57–3.86(6H, broad), 3.99(6H, s), 7.18–7.33(4H, m) |
| 46 | (trimethyl-benzoquinone-CH2-phenyl-CH2CH2-C(O)NH-iPr) | Powder | 354(M + H)+ | 1.05(6H, d, J=6.6 Hz), 2.01(6H, s), 2.08(3H, s), 2.37(2H, m), 2.89(2H, m) 3.82(2H, s), 4.03(1H, m), 5.05(1H, broad), 7.08(4H, s) |
| 47 | (trimethyl-benzoquinone-CH2-phenyl-CH2CH2-C(O)-piperidine) | Oil | 380(M + H)+ | 1.43–1.60(6H, broad), 2.01(6H, s), 2.09(3H, s), 2.57(2H, m), 2.90(2H, m), 3.31(2H, m), 3.54(2H, m), 3.82(2H, s), 7.10(4H, s) |
| 48 | (trimethyl-benzoquinone-CH2-phenyl-CH2CH2-C(O)-morpholine) | Oil | 382(M + H)+ | 2.01(6H, s), 2.09(3H, s), 2.57(2H, m), 2.92(2H, m), 3.35(2H, m), 3.49(2H, s), 3.61(4H, broad), 3.83(2H, s), 7.10(4H, s) |
| 49 | (trimethyl-benzoquinone-CH2-phenyl-CH2CH2-C(O)NH-iPr, meta) | Powder | 354(M + H)+ | 1.07(6H, d, J=6.5 Hz), 2.02(6H, s), 2.08(3H, s), 2.38(2H, m), 2.90(2H, m), 3.83(2H, s), 4.03(1H, m), 5.09(1H, broad), 7.00(3H, m), 7.16(1H, m) |

-continued

| | Structure | State | MS | ¹H NMR |
|---|---|---|---|---|
| 50 | [piperidine-C(O)-CH₂CH₂-phenyl-CH₂-trimethylbenzoquinone] | Oil | 380(M + H)⁺ | 1.46–1.62(6H, broad), 2.02(6H, s), 2.08(3H, s), 2.57(2H, m), 2.91(2H, m), 3.32(2H, m), 3.55(2H, m), 3.84(2H, s), 6.98–7.04(3H, m), 7.17(1H, m) |
| 51 | [morpholine-C(O)-CH₂CH₂-phenyl-CH₂-trimethylbenzoquinone] | Oil | 382(M + H)⁺ | 2.02(3H, s), 2.04(3H, s), 2.09(3H, s), 2.58(2H, m), 2.93(2H, m), 3.36(2H, broad), 3.52(2H, broad), 3.62(4H, broad), 3.84(2H, s), 7.01(3H, m), 7.18(1H, m) |
| 52 | [HOOC-CH₂-phenyl-CH₂-dimethoxymethylbenzoquinone] | Oil | 331(M + H)⁺ | 2.08(3H, s), 3.63(2H, s), 3.83(2H, s) 3.98(6H, s), 7.16(2H, d, J=7.8 Hz), 7.21(2H, d, J=7.8 Hz) |
| 53 | [morpholine-C(O)-CH₂-phenyl-CH₂-dimethoxymethylbenzoquinone] | Oil | 400(M + H)⁺ | 2.07(3H, s), 3.43(2H, m) 3.51(2H, m), 3.64(4H, broad), 3.66(2H, s), 3.82(2H, s), 3.98(6H, s), 7.13(4H, m) |
| 54 | [piperidine-C(O)-CH₂-phenyl-CH₂-dimethoxymethylbenzoquinone] | Oil | 398(M + H)⁺ | 1.38(2H, broad) 1.52(2H, broad) 1.55(2H, broad) 2.08(3H, s), 3.36(2H, m) 3.55(2H, s) 3.66(2H, s), 3.82(2H, s) 3.99(3H, s) 3.98(6H, s) 7.13(4H, m) |

| | | | |
|---|---|---|---|
| 55 | [structure: dimethoxy-methyl-benzoquinone-CH2-phenyl(para)-CH2-C(O)-N-thiomorpholine] | Oil | 416(M + H)+ | 2.08(3H, s) 2.34(2H, m) 2.58(2H, m) 3.67(2H, s) 3.69(2H, m) 3.82(2H, s) 3.88(2H, s) 3.99(6H, s) 7.14(4H, s) |
| 56 | [structure: dimethoxy-methyl-benzoquinone-CH2-phenyl(para)-CH2-C(O)-NH-isopropyl] | Powder | 372(M + H)+ | 1.07(6H, d, J=6.6 Hz) 2.09(3H, s) 3.47(2H, s) 3.84(2H, s) 3.99(3H, s) 4.00(3H, s) 4.04(1H, m) 5.14(1H, broad) 7.15(4H, s) |
| 57 | [structure: dimethoxy-methyl-benzoquinone-CH2-phenyl(meta)-CH2-COOH] | Oil | 331(M + H)+ | 2.09(3H, s) 3.62(2H, s) 3.84(2H, s) 3.99(6H, s) 7.11(3H, m) 7.24(1H, m) |
| 58 | [structure: dimethoxy-methyl-benzoquinone-CH2-phenyl(meta)-CH2-C(O)-piperidine] | Oil | 398(M + H)+ | 1.34(2H, broad) 1.53(2H, broad) 1.55(2H, broad) 2.07(3H, s) 3.35(2H, m) 3.56(2H, m) 3.68(2H, s) 3.82(2H, s) 3.99(6H, s) 3.99(1H, d, J=7.6 Hz) 7.08(2H, m) 7.21(1H, m) |
| 59 | [structure: dimethoxy-methyl-benzoquinone-CH2-phenyl(meta)-CH2-C(O)-N-thiomorpholine] | Oil | 416(M + H)+ | 2.08(3H, s) 2.29(2H, m) 2.57(2H, m) 3.68(4H, m) 3.83(2H, s) 3.88(2H, s) 3.99(6H, s) 7.06(3H, m) 7.23(1H, m) |

| | Structure | State | MS | ¹H-NMR |
|---|---|---|---|---|
| 60 | (quinone with methoxy groups, methyl, benzyl-CH₂-C(O)-morpholine) | Oil | 400(M + H)⁺ | 2.08(3H, s), 3.42(2H, m), 3.49(2H, m), 3.64(4H, s), 3.68(2H, s), 3.82(2H, s), 3.99(6H, s), 7.06(3H, m), 7.23(1H, m) |
| 61 | (quinone, N-isopropyl amide) | Powder | 372(M + H)⁺ | 1.07(6H, d, J=6.6 Hz), 2.08(3H, s), 3.49(2H, s), 3.84(2H, s), 4.00(6H, s), 4.04(1H, m), 5.14(1H, broad), 7.08(3H, m), 7.25(1H, m) |
| 62 | (quinone, propyl-COOH) | Oil | 359(M + H)⁺ | 1.93(2H, m), 2.09(3H, s), 2.36(2H, m), 2.63(2H, m), 3.82(3H, s), 3.99(6H, s), 6.99–7.03(3H, m), 7.18(1H, m) |
| 63 | (quinone, propyl-C(O)-piperidine) | Oil | 426(M + H)⁺ | 1.51–1.63(6H, m), 1.92(2H, m), 2.08(3H, s), 2.31(2H, m), 2.62(2H, m), 3.33(2H, m), 3.54(2H, m), 3.82(2H, s), 3.99(3H, s), 4.00(3H, s), 6.97–7.04(3H, m), 7.18(1H, m) |
| 64 | (quinone, propyl-C(O)-thiomorpholine) | Oil | 444(M + H)⁺ | 1.94(2H, m), 2.08(3H, s), 2.29(2H, m), 2.56–2.65(6H, m), 3.66(2H, m), 3.82(2H, s), 3.87(2H, m), 3.99(3H, s), 4.00(3H, s), 6.98–7.03(3H, m), 7.18(1H, m) |

| | Structure | State | MS | NMR |
|---|---|---|---|---|
| 65 | (quinone with methyl, two methoxy, benzyl-phenyl-propyl-morpholine amide) | Oil | 428(M + H)⁺ | 1.94(2H, m), 2.08(3H, s), 2.30(2H, m), 2.63(2H, m), 3.39(2H, m), 3.61–3.65(6H, m), 3.82(2H, s), 3.99(3H, s), 4.00(3H, s), 6.98–7.03(3H, m), 7.18(1H, m) |
| 66 | (quinone with methyl, two methoxy, benzyl-phenyl-propyl-isopropylamide) | Oil | 400(M + H)⁺ | 1.15(6H, d, J=6.5 Hz), 1.93(2H, m), 2.10(3H, s), 2.10(2H, m), 2.60(2H, m), 3.81(2H, s), 3.99(6H, s), 4.09(1H, m), 5.32(1H, broad), 6.97–7.02(3H, m), 7.18(1H, m) |
| 67 | (quinone with methyl, two methoxy, benzyl-phenyl-cinnamic acid) | Powder | 343(M + H)⁺ | 2.00(3H, S) 3.99(5H, s) 4.02(3H, s) 6.39(1H, d, J=15.7 Hz) 6.96(1H, d, J=7.0 Hz) 7.25–7.31(2H, m) 7.59(1H, d, J=7.2 Hz) 8.22(1H, d, J=15.7 Hz) |
| 68 | (quinone with methyl, two methoxy, benzyl-phenyl-acryloyl-thiomorpholine) | Powder | 428(M + H)⁺ | 1.97(3H, s) 2.70(4H, broad) 3.97(2H, s) 3.98(2H, s) 3.99(3H, s) 4.02(3H, s) 6.75(1H, d, J=15.1 Hz) 6.89(1H, m) 1.23(2H, m) 7.51(1H, m) 8.07(1H, d, J=15.1 Hz) |

| | | | |
|---|---|---|---|
| 69 | [structure: dimethoxy-methyl-benzoquinone with CH2-phenyl-CH2CH2COOH] | Oil | 345(M+H)+ | 2.02(3H, s) 2.77(2H, m) 3.10(2H, m) 3.85(2H, s) 3.98(3H, s) 4.03(3H, s) 6.81(1H, d, J=7.5 Hz) 7.10–7.21(3H, m) |
| 70 | [structure: dimethoxy-methyl-benzoquinone with CH2-phenyl-CH2CH2C(O)-piperidine] | Oil | 412(M+H)+ | 1.47–1.62(6H, broad) 2.00(3H, s) 2.70(2H, m) 3.10(2H, m) 3.38(2H, m) 3.58(2H, m) 3.86(2H, s) 3.98(3H, s) 4.03(3H, s) 6.78(1H, d, J=7.4 Hz) 7.09(1H, m) 7.14(1H, m) 7.20(1H, m) |
| 71 | [structure: dimethoxy-methyl-benzoquinone with CH2-phenyl-CH2CH2C(O)-morpholine] | Oil | 414(M+H)+ | 2.02(3H, s) 2.73(2H, m) 3.11(2H, m) 3.42(2H, m) 3.49(2H, m) 3.64(4H, m) 3.85(2H, s) 3.98(3H, s) 4.03(3H, s) 6.79(1H, d, J=7.5 Hz) 7.10–7.19(3H, m) |

| No. | Structure | Property | FABMS (m/z) | NMR(CDCl₃, δ) |
|---|---|---|---|---|
| 72 | [structure: dimethoxy methyl benzoquinone with benzyl-CH₂CH₂C(O)-thiomorpholine] | Powder | 430(M + H)⁺ | 2.02(3H, s) 2.44(2H, m) 2.60(2H, m) 2.72(2H, m) 3.10(2H, m) 3.68(2H, m) 3.85(2H, s) 3.90(2H, m) 3.98(3H, s) 4.03(3H, s) 6.79(1H, d, J=7.5 Hz) 7.08–7.21(3H, m) |
| 73 | [structure: dimethoxy methyl benzoquinone with benzyl-CH₂CH₂C(O)NH-isopropyl] | Powder | 386(M + H)⁺ | 1.02(6H, d, J=6.6 Hz) 2.06(3H, s) 2.56(2H, m) 3.08(2H, m) 3.85(2H, s) 3.97(3H, s) 4.00(1H, m) 4.04(3H, s) 5.52(1H, broad) 6.79(1H, d, J=7.4 Hz) 7.10(2H, m) 7.18(1H, d, J=7.3 Hz) |

| Production Example No. | Structure | Weight (yield) | Property | FABMS (m/z) | NMR(CDCl₃, δ) |
|---|---|---|---|---|---|
| 74 | [structure: dimethoxy methyl benzoquinone with para-substituted benzene-CH₂CH₂C(O)-pyrrolidine with methoxymethyl substituent] | 38 mg(29%) | Oil | 442(M + H)⁺ | 1.82–1.98(4H, m), 2.08(3H, s), 2.52(2H, m), 2.93(3H, m), 3.15–3.23(1H, m), 3.33(3H, s), 3.36–3.40(1H, m), 3.50–5.53(1H, m), 3.81(2H, s), 3.98(3H, s), 3.99(3H, s), 4.24(1H, m), 7.10(4H, m) |

-continued

| # | Structure | Yield | Form | MS / NMR |
|---|---|---|---|---|
| 75 | (structure) | 34 mg (25%) | Powder | 460(M + H)+ 1.66(1H, m), 2.07(3H, s), 2.37(2H, m), 2.53(1H, m), 2.86(2H, m)2.96(2H, m), 3.81(2H, s), 3.98(3H, s), 3.99(3H, s), 5.46(1H, m), 5.50(1H, d, J=8.4 Hz), 7.10–7.22(5H, m) |
| 76 | (structure) | 36 mg (27%) | Oil | 442(M + H)+ 1.82–1.98(4H, m), 2.08(3H, s), 2.52(2H, m), 2.92(3H, m), 3.15–3.23(1H, m), 3.33(3H, s), 3.36–3.40(1H, m), 3.50–5.54(1H, m), 3.81(2H, s), 3.98(3H, s), 3.99(3H, s), 4.24(1H, m), 7.10(4H, m) |
| 77 | (structure) | 79 mg (58%) | Oil | 456(M + H)+ 1.90–2.16(4H, m), 2.08(3H, s), 2.38–2.63(2H, m), 2.93(2H, m), 3.37(1H, m), 3.56(1H, m), 3.73(3H, s), 3.81(2H, s), 3.98(3H, s), 3.99(3H, s), 4.48(1H, m), 7.12(4H, m) |
| 78 | (structure) | 61 mg (23%) | Powder | 531(M + H)+ 2.17(3H, s), 2.53(3H, s), 2.63(2H, m), 2.95(2H, m), 3.24(2H, m), 3.22(2H, m), 3.54(2H, m), 3.78(2H, m), 3.80(2H, m), 3.98(6H, s), 6.84(2H, m), 7.11(4H, m), 7.89(2H, m) |

| # | Structure | Yield | Form | MS | ¹H NMR |
|---|---|---|---|---|---|
| 79 | 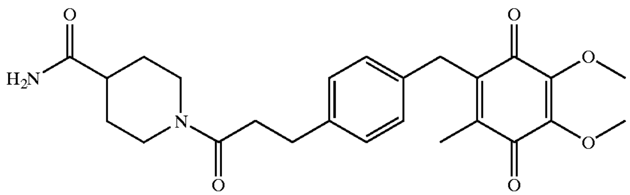 | 41 mg(30%) | Powder | 455(M + H)⁺ | 1.43–1.60(2H, m), 1.80–1.92(2H, m), 2.08(3H, s), 2.34(1H, m), 2.58(2H, m), 2.67(1H, m), 2.89–2.97(3H, m), 3.78(1H, m), 3.81(2H, s), 3.99(6H, s), 4.59(1H, m), 5.38(1H, broad s), 5.51(1H, broad s), 7.10(4H, m) |
| 80 | 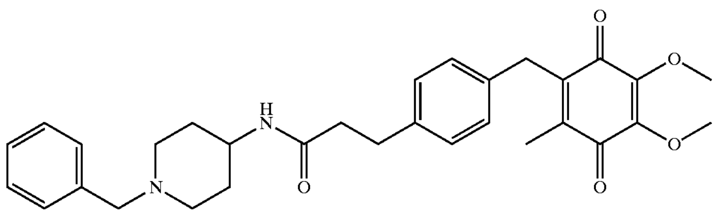 | 59 mg(38%) | Powder | 517(M + H)⁺ | 1.29–1.35(2H, m), 1.82(2H, m), 2.07(3H, s), 2.09(2H, m), 2.38–2.42(2H, m), 2.76(2H, m), 2.87–2.91(2H, m), 3.47(2H, s), 3.76(1H, m), 3.80(2H, s), 3.98(6H, s), 5.14(1H, d, J=8.1 Hz), 7.08(4H, s), 7.24–7.33(4H, m) |
| 81 | 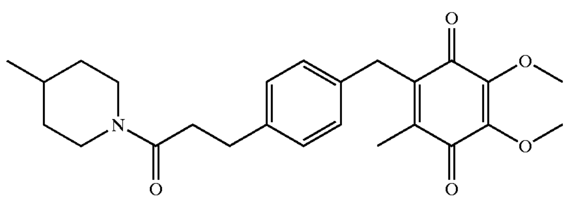 | 68 mg(53%) | Oil | 426(M + H)⁺ | 0.92(3H, t, J=6.5 Hz), 0.96–1.10(2H, m), 1.55–1.66(3H, m), 2.08(3H, s), 2.52–2.59(3H, m), 2.89–2.94(3H, m), 3.74(1H, m), 3.81(2H, s), 3.98(3H, s), 3.99(3H, s), 4.58(1H, s), 7.07–7.13(4H, m) |
| 82 | 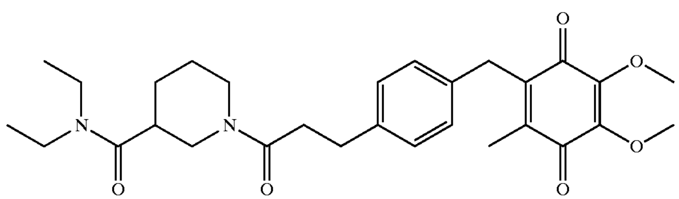 | 120 mg(78%) | Oil | 511(M + H)⁺ | 1.10 and 1.21(total 6H, both d, J=7.1 Hz), 1.71–1.92(3H, m), 2.08(3H, s), 2.43–2.69(4H, m), 2.89–3.00(3H, m), 3.20–3.49(5H, m), 3.78(1H, m), 3.81(2H, s), 3.98(3H, s), 3.99(3H, s), 4.65(1H, m), 7.08–7.11(1H, m) |
| 83 | 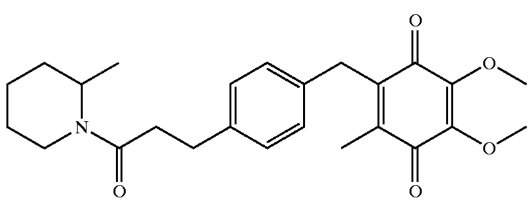 | 59 mg(46%) | Oil | 426(M + H)⁺ | 1.10–1.17(3H, m), 1.24–1.37(1H, broad), 1.50–1.58(5H, m), 2.08(3H, s), 2.53–2.67(2.5H, m), 2.90–3.13(2.5H, m), 3.56(0.5H, m), 3.81(2H, s), 3.98(3H, s), 3.99(3H, s), 4.06(0.5H, m), 4.52(0.5H, m), 4.93(0.5H, broad), 7.08–7.13(4H, m) |

| | | | | |
|---|---|---|---|---|
| 84 | [structure] | 63 mg(46%) | Powder | 460(M + H)+ 2.07(3H, s), 2.37(2H, m), 2.65–2.70(2H, m), 2.89(2H, m), 3.23–3.29(2H, m), 3.80(2H, s), 3.98(6H, s), 4.71(1H, m), 5.51(1H, d, J=7.4 Hz), 7.07(4H, s), 7.16–7.22(4H, m) |
| 85 | [structure] | 69 mg(54%) | Oil | 426(M + H)+ 0.85 and 0.83(total 3H, both d, J=6.6 Hz), 1.03–1.14(1H, m), 1.24–1.67(3H, m), 1.78(1H, m), 2.08(3H, s), 2.17–2.23(0.5H, m), 2.55–2.60(3H, m), 2.83–2.93(2.5H, m), 3.60(0.5H, m), 3.68(0.5H, m), 3.81(2H, s), 3.98(3H, s), 3.99(3H, s), 4.44(1H, m), 7.09–7.13(4H, m) |
| 86 | [structure] | 20 mg(15%) | Oil | 440(M + H)+ 1.19(6H, d, J=7.0 Hz), 1.42–1.63(5H, m), 1.73–1.79(1H, m), 2.08(3H, s), 2.53–2.64(2H, m), 2.91–2.95(2H, m), 3.81(2H, s), 3.98(3H, s), 3.99(3H, s), 4.00(1H, broad), 4.77(1H, broad), 7.08–7.14(4H, m) |
| 87 | [structure] | 64 mg(50%) | Oil | 428(M + H)+ 1.52–1.57(1H, m), 1.74–1.88(2H, m), 1.95–2.02(1H, m), 2.08(3H, s), 2.53–2.59(2H,m), 2.90–2.96(2H, m), 3.27–3.41(2H, m), 3.51–3.57(1H, m), 3.62–3.68(1H, m), 3.81 (2H, s), 3.99(6H, s), 4.18–4.21(1H, m), 5.05–5.30(1H, m), 7.09–7.14(4H, m) |

| | | | | |
|---|---|---|---|---|
| 88 | [structure] | 48 mg (36%) | Oil | 442(M + H)+ 1.01–1.93(6H, m), 2.08(3H, s), 2.43–2.71(3H, m), 2.89–3.11(3H, m), 3.58–3.66(2H, m), 3.78–3.91(1H, m), 3.81(2H, s), 3.98(3H, s), 3.99(3H, s), 4.59–4.79(1H, m), 7.08–7.13(4H, m) |
| 89 | [structure] | 120 mg (86%) | Oil | 464(M + H)+ 2.07(3H, s), 2.58(2H, m), 2.99(2H, m), 3.81(2H, s), 3.98(6H, s), 5.94(2H, s), 6.65(1H, m), 6.71(1H, m), 6.87(1H, broad), 7.12(5H, m) |
| 90 | [structure] | 110 mg (77%) | Oil | 478(M + H)+ 2.07(3H, s), 2.58(2H, m), 2.99(2H, m), 3.81(2H, s), 3.98(6H, s), 4.23(4H, broad s), 6.77(2H, m), 6.81(1H, broad), 7.12(4H, m) |
| 91 | [structure] | 46 mg (30%) | Powder | 505(M + H)+ 2.07(3H, s), 2.59(2H, m), 3.00(2H, m), 3.11(4H, m), 3.84(6H, m), 3.98(6H, s), 6.85(4H, m), 7.12(4H, m), 7.28(1H, m) |

| | | | | |
|---|---|---|---|---|
| 92 | [structure] | 136 mg (52%) Oil | 524 (M + H)+ | 2.08(3H, s), 2.68(2H, m), 3.02(2H, m), 3.81(3H, s), 3.97(6H, s), 7.12(4H, s), 7.41(1H, broad s), 7.46–7.60(4H, m), 7.78(4H, m) |
| 93 | [structure] | 59 mg (43%) Powder | 462 (M + H)+ | 2.08(3H, s) 2.57(3H, s) 2.67(2H, m) 3.01(2H, m) 3.81(2H, s) 3.98(6H, s) 7.13(4H, s) 7.21(1H, broad) 7.53(2H, m) 7.91(2H, m) |
| 94 | [structure] | 79 mg (59%) Powder | 450 (M + H)+ | 2.08(3H, s), 2.60(2H, m), 3.00(2H, m), 3.78(3H, s), 3.81(2H, s), 3.98(6H, s), 6.83(2H, m), 6.86(1H, broad), 7.12(4H, m), 7.30(2H, m) |
| 95 | [structure] | 63 mg (45%) Powder | 463 (M + H)+ | 2.08(3H, s), 2.58(2H, m), 2.91(6H, s), 3.00(2H, m), 3.81(2H, s), 3.98(6H, s), 6.67(2H, d, J=9.0 Hz), 6.81(1H, broad), 7.12(4H, m), 7.24(2H, d, J=8.9 Hz) |

| | | | | |
|---|---|---|---|---|
| 96 | [structure] | 45 mg(34%) | Powder | 436(M + H)+ 2.08(3H, s), 2.72(2H, m), 3.02(2H, m), 3.82(2H, s), 3.98(3H, s), 3.99(3H, s), 6.82(2H, d, J=4.2 Hz), 6.99(1H, d, J=7.9 Hz), 7.08–7.19(6H, m), 8.58(1H, broad) |
| 97 | [structure] | 60 mg(46%) | Oil | 436(M + H)+ 2.12(3H, s) 2.62(2H, m) 3.00(2H, m) 3.83(2H, s) 3.98(3H, s) 3.99(3H, s) 6.61(1H, d, J=8.1 Hz) 6.66(1H, broad) 6.78(1H, d, J=8.1 Hz) 7.11–1.17(5H, m) 8.02(1H, broad) |
| 98 | [structure] | 94 mg(64%) | Oil | 488(M + H)+ 2.08(3H, s), 2.62(2H, m), 2.99(2H, m), 3.81(2H, s), 3.98(6H, s), 7.00(1H, s), 7.08(1H, broad), 7.12(4H, s), 7.40(2H, s) |
| 99 | [structure] | 120 mg(84%) | Oil | 480(M + H)+ 2.07(3H, s), 2.61(2H, m), 3.00(2H, m) 3.75(3H, s) 3.77(3H, s) 3.81(2H, s) 3.98(6H, s) 6.22(1H, broad) 6.69(2H, broad) 6.95(1H, broad) 7.12(4H, m) |

-continued

| | | | | |
|---|---|---|---|---|
| 100 | [structure] | 71 mg (48%) | Powder | 492(M + H)+ 1.38(3H, m), 2.08(3H, s), 2.66(2H, m), 3.01(2H, m), 3.81(2H, s), 3.98(6H, s), 4.35(2H, m), 7.11(4H, m), 7.15(1H, broad), 7.51(2H, d, J=8.5 Hz), 7.98(2H, d, J=8.7 Hz) |
| 101 | [structure] | 63 mg (41%) | Powder | 510(M + H)+ 2.08(3H, s), 2.61(2H, m), 3.00(2H,m), 3.81(5H, s), 3.84(6H, s), 3.98(6H, s), 6.76(2H, s), 6.98(1H, broad), 7.12(4H, m) |
| 102 | [structure] | 94 mg (56%) | Oil | 556(M + H)+ 2.07(3H, s), 2.67(2H, m), 3.01(2H, m), 3.81(2H, s), 3.98(6H, s), 7.12(4H, s), 7.43(1H, broad), 7.59(1H, broad), 7.95(2H, s) |
| 103 | [structure] | 31 mg (20%) | Powder | 480(M + H)+ 2.08(3H, s), 2.60(2H, m), 3.00(2H, m), 3.81(2H, s), 3.85(3H, s), 3.88(3H, s), 3.98(6H, s), 6.71(1H, m), 6.78(1H, m), 6.91(1H, broad), 7.13(4H, m), 7.31(1H, broad) |

| | | | | |
|---|---|---|---|---|
| 104 | [structure] | 46 mg(40%) | Oil | 402(M + H)⁺ 1.06(3H, d, J=7.0 Hz), 2.41–2.46(2H, m) 2.91(2H, m), 2.08(3H, s), 3.40–3.44(1H, m), 3.52–3.56(1H, m), 3.81(2H, s), 3.99(6H, s), 5.40(1H, m), 7.10(4H, s) |
| 105 | [structure] | 91 mg(63%) | Oil | 484(M + H)⁺ 1.27(3H, t, J=7.1 Hz), 1.28–1.70(4H, m), 2.08(3H, s), 2.25(1H, m), 2.64(2H, m), 2.92(2H, m), 3.19–3.36(1H, m), 3.71(1H, m), 3.81(2H, s), 3.98(3H, s), 3.99(3H, s), 4.15–4.21(3H, m), 5.37(1H, m), 7.08–7.14(4H, m) |
| 106 | [structure] | 93 mg(70%) | Oil | 441(M + H)⁺ 1.78(1H, m), 1.93(1H, m), 2.04(1H, m), 2.08(3H, s), 2.40(1H, m), 2.60(2H, m), 2.94(2H, m), 3.29(1H, m), 3.45(1H, m), 3.81(2H, m), 3.98(3H, s), 3.99(3H, s), 4.58(1H, m), 5.30(1H, broad s), 6.92(1H, broad s), 7.11(4H, m) |
| 107 | [structure] | 110 mg(76%) | Oil | 484(M + H)⁺ 1.25(3H, t, J=7.1 Hz), 1.29–1.48(1H, m), 1.58–1.78(2H, m), 2.02(1H, m), 2.08(3H, s), 2.25–2.43(1H, m), 2.56–2.67(2H, m), 2.78–3.01(3.5H, m), 3.28–3.34(0.5H, m), 3.66–3.75(1H, m), 3.81(2H, s), 3.98(3H, s), 3.99(3H, s), 4.11–4.16(3H, m), 4.65(0.5H, m), 7.10(4H, m) |
| 108 | [structure] | 140 mg(90%) | Powder | 512(M + H)⁺ 2.07(3H, s), 2.61(2H, m), 3.00(2H, m), 3.81(2H, s), 3.98(6H, s), 6.92–6.98(4H, m), 7.04–7.15(6H, m), 7.30–7.38(4H, m) |

| | | | | |
|---|---|---|---|---|
| 109 | [structure] | 59 mg(43%) | Oil | 466(M + H)+ 0.98–1.76(13H, broad) 2.07(1H, broad) 2.08(3H, s) 2.56(2H, m) 2.92(2H, m) 3.14(2H, broad) 3.81(2H, s) 3.98(3H, s) 3.99(3H, s) 7.11(4H, m) |
| 110 | [structure] | 130 mg(88%) | Oil | 492(H + H)+ 1.38(3H, t, J=7.1 Hz), 2.07(3H, s), 2.64(2H, m), 3.00(2H, m), 3.81 (2H, s), 3.98(6H, s), 4.32–4.39(3H, m), 7.12(4H, m), 7.20(1H, m), 7.36(1H, m), 7.76–7.93(3H, m) |
| 111 | [structure] | 72 mg(52%) | Powder | 459(M + H)+ 2.07(3H, s), 2.63(2H, m), 3.00(2H, m), 3.71(2H, s), 3.81(2H, s), 3.99(6H, s), 7.02(2H, m), 7.11(4H, m), 7.25(2H, m), 7.44(2H, m) |
| 112 | [structure] | 130 mg(94%) | Powder | 462(M + H)+ 1.22(0H, d, J=6.9 Hz), 2.07(3H, s), 2.60(2H, m), 2.86(1H, m), 3.00(2H, m), 3.81 (2H, s), 3.98(6H, s), 6.96(1H, broad s), 7.09–7.16(6H, m), 7.32(2H, m) |

-continued

| # | Structure | Yield | Form | MS / NMR |
|---|---|---|---|---|
| 113 | (4-pentylphenyl propanamide, 2,3-dimethoxy-5-methyl-1,4-benzoquinone) | 60 mg (41%) | Powder | 490(M + H)⁺ 0.88(3H, t, J=6.7 Hz), 1.27–1.35(4H m), 1.56–1.61(2H, m), 2.07(3H, s), 2.53–2.62(4H, m), 3.00(2H, m), 3.81(2H, s), 3.98(6H, s), 6.96(1H, broad s), 7.11–7.15(6H, m), 7.31(2H, m) |
| 114 | (3,5-dibromo-4-hydroxyphenyl propanamide, 2,3-dimethoxy-5-methyl-1,4-benzoquinone) | 84 mg (28%) | Powder | 594(M + H)⁺ 2.08(3H, s), 2.59(2H, m), 2.98(2H, m), 3.82(2H, s), 3.98(6H, s), 5.75(1H, broad s), 6.95(1H, broad s), 7.11(4H, s), 7.58(2H, s) |
| 115 | (3-hydroxy-4-methoxyphenyl propanamide, 2,3-dimethoxy-5-methyl-1,4-benzoquinone) | 42 mg (30%) | Powder | 446(M + H)⁺ 2.08(3H, s), 2.58(2H, m), 2.99(2H, m), 3.81(2H, s), 3.86(3H, s), 3.98(6H, s), 6.76(1H, d, J=8.6 Hz), 6.90–7.09(3H, m), 7.11(4H, m) |
| 116 | (4-propoxyphenyl propanamide, 2,3-dimethoxy-5-methyl-1,4-benzoquinone) | 92 mg (62%) | Powder | 492(M + H)⁺ 0.97(3H, t, J=7.4 Hz), 1.45–1.52(2H, m), 1.71–1.78(2H, m), 2.08(3H, s), 2.59(2H, s), 3.00(2H, m), 3.81(2H, s), 3.92(2H, m), 3.98(6H, s), 6.82(2H, m), 7.12(4H, m), 7.29(2H, m) |

| | | | | |
|---|---|---|---|---|
| 117 | [structure] | 85 mg (58%) | Powder | 488(M + H)⁺ 2.08(3H, s), 2.65(2H, m), 3.00(2H, m), 3.81(2H, s), 3.98(6H, s), 7.12(5H, m), 7.54(4H, m) |
| 118 | [structure] | 71 mg (60%) | Powder | 445(M + H)⁺ 2.08(3H, s), 2.66(2H, m), 3.00(2H, m), 3.81(2H, s), 3.99(6H, s), 7.10–7.15(5H, m), 7.53–7.60(4H, m) |
| 119 | [structure] | 88 mg (33%) | Oil | 536(M + H)⁺ 1.60(9H, s), 2.08(3H, s), 2.63(2H, m), 2.99(2H, m), 3.81(2H, s), 3.98(6H, s), 6.99–7.13(7H, m), 7.68(1H, m), 11.12(1H, s) |

| | | | | |
|---|---|---|---|---|
| 120 | [structure] | 75 mg(61%) | Oil | 448(M + H)⁺ 1.40(3H, d, J=6.8 Hz) 2.07(3H, s) 2.43(2H, m) 2.91(2H, m) 3.81(2H, s) 3.98(3H, s) 3.99(3H, s) 5.09(1H, m) 5.49(1H, broad) 7.07(4H, s) 7.21(2H, m) 7.24–7.33(3H, m) |
| 121 | [structure] | 80 mg(58%) | Oil | 448(M + H)⁺ 1.40(3H, d, J=7.0 Hz) 2.08(3H, s) 2.43(2H, m) 2.91(2H, m) 3.81(2H, s) 3.98(3H, s) 3.99(3H, s) 5.09(1H, m) 5.48(1H, broad) 7.07(4H, s) 7.21(2H, m) 7.25–7.33(3H, m) |
| 122 | [structure] | 39 mg(28%) | Powder | 457(M + H)⁺ 2.07(3H, s) 2.38–2.48(8H, m) 2.90(2H, m) 3.32(2H, m) 3.67(4H, m) 3.80(2H, s) 3.98(3H, s) 3.99(3H, s) 5.88(1H, broad) 7.10(4H, m) |
| 123 | [structure] | 68 mg(53%) | Oil | 428(M + H)⁺ 0.90(9H, s) 1.32(2H, m) 2.07(3H, s) 2.40(2H, m) 2.90(2H, m) 3.21(2H, m) 3.80(2H, s) 3.98(3H, s) 3.99(3H, s) 5.19(1H, broad) 7.09(4H, s) |

| | | | | |
|---|---|---|---|---|
| 124 | [structure] | 59 mg(48%) | Powder | 414(M + H)+ 0.78(6H, m) 1.27(2H, m) 1.46(2H, m) 2.07(3H, s) 2.43(2H, m) 2.92(2H, m) 3.74(1H, m) 3.80(2H, s) 3.98(3H, s) 3.99(3H, s) 4.96(1H, broad) 7.10(4H, m) |
| 125 | [structure] | 22 mg(18%) | Powder | 418(M + H)+ 2.10(3H, s) 2.47(2H, m) 2.93(2H, m) 3.59(2H, m) 3.73(2H, m) 3.81(2H, s) 3.85(1H, m) 3.98(3H, s) 3.99(3H, s) 5.96(1H, broad) 7.10(1H, m) |
| 126 | [structure] | 49 mg(40%) | Powder | 416(M + H)+ 0.84(2H, m) 1.38(1H, m) 1.49(1H, m) 2.08(3H, s) 2.33(1H, broad) 2.46(2H, m) 2.92(2H, m) 3.52(2H, m) 3.78(1H, broad) 3.81(2H, s) 3.99(6H, s) 5.37(1H, broad) 7.10(4H, s) |
| 127 | [structure] | 53 mg(44%) | Powder | 400(M + H)+ 0.80(3H, m) 1.02(3H, d, J=6.6 Hz) 1.36(2H, m) 2.07(3H, s) 2.40(2H, m) 2.91(2H, m) 3.80(2H, s) 3.87(1H, m) 3.98(3H, s) 3.99(3H, s) 5.03(1H, broad) 7.09(4H, s) |
| 128 | [structure] | 61 mg(48%) | Oil | 428(M + H)+ 0.86(6H, m) 1.02(3H, d, J=6.5 Hz) 1.12–1.27(2H, m) 1.46(1H, m) 2.07(3H, s) 2.39(2H, m) 2.90(2H, m) 3.80(2H, s) 3.98(3H, s) 3.99(3H, s) 4.01(1H, m) 4.99(1H, broad) 7.09(4H, s) |

| | | | | |
|---|---|---|---|---|
| 129 | [structure] | 62 mg (45%) | Powder | 456(M + H)⁺ 0.87(3H, m) 1.03(3H, d, J=6.5 Hz) 1.24–1.32(10H, broad) 2.07(3H, s) 2.39(2H, m) 2.90(2H, m) 3.80(2H, s) 3.93(1H, m) 3.98(3H, s) 3.99(3H, s) 5.03(1H, broad) 7.09(4H, s) |
| 130 | [structure] | 59 mg (43%) | Oil | 458(M + H)⁺ 1.114(3H, d, J=6.7 Hz) 1.26(3H, m) 2.07(3H, s) 2.38–2.45(4H, m) 2.89(2H, m) 3.80(2H, s) 3.98(3H, s) 3.99(3H, s) 4.13(2H, m) 4.32(1H, m) 5.98(1H, broad) 7.09(4H, s) |
| 131 | [structure] | 49 mg (39%) | Powder | 444(M + H)⁺ 0.87(3H, m) 1.22–1.37(6H, m) 2.08(3H, s) 2.33(1H, m) 2.46(2H, m) 2.92(2H, m) 3.48(1H, m) 3.54(1H, m) 3.81(2H, s) 3.86(1H, m) 3.99(6H, s) 5.37(1H, broad) 7.10(4H, s) |
| 132 | [structure] | 49 mg (41%) | Oil | 398(M + H)⁺ 1.80–1.90(4H, m) 2.08(3H, s) 2.52(2H, m) 2.93(2H, m) 3.28(2H, m) 3.45(2H, m) 3.80(2H, s) 3.98(3H, s) 3.99(3H, s) 7.11(4H, m) |

| | | | | |
|---|---|---|---|---|
| 133 | (structure) | 43 mg(32%) | Powder | 455(M + H)+ 1.39(2H, broad) 1.82(2H, broad) 2.07(3H, s) 2.50(2H, m) 2.91(2H, m) 3.25(2H, broad) 3.80(2H, s) 3.99(3H, s) 3.99(3H, s) 4.48(1H, m) 5.87(1H, broad) 6.80(1H, broad) 7.09(4H, s) |
| 134 | (structure) | 70 mg(56%) | Oil | 414(M + H)+ 1.76–2.00(3H, broad) 2.08, 2.09(total 3H, both s) 2.53(2H, m) 2.93(2H, m) 3.15(0.4H, m) 3.34–3.62(3.6H, m) 3.81(2H, s) 3.98(3H, s) 3.99(3H, s) 4.46(1H, broad) 7.10(4H, m) |
| 135 | (structure) | 25 mg(19%) | Oil | 426(M + H)+ 1.08, 1.13, 1.29(total 6H, all d, J=6.4, 6.5, 6.3 Hz) 1.48–1.66(2.5H, m) 1.80–1.88(0.7H, m) 1.99–2.06(1.3H, m) 2.08(3H, s) 2.53(2H, m) 2.94(2H, m) 3.81(2H, s) 3.82(3H, s) 3.98(3H, s) 3.99(3H, s) 4.05–4.23(0.5H, m) 7.11(4H, m) |
| 136 | (structure) | 79 mg(60%) | Powder | 440(M + H)+ 1.30(2H, m) 1.45–1.58(5H, broad) 1.82(2H, broad) 2.07(3H, s) 2.18(3H, s) 2.38(2H, m) 2.90(2H, m) 3.80(2H, s) 3.91(1H, m) 3.98(3H, s) 3.99(3H, s) 5.19(1H, broad) 7.09(4H, s) |
| 137 | (structure) | 72 mg(55%) | Oil | 440(M + H)+ 0.71(1H, m) 0.83, 0.88(total 6H, both d, J=6.6, 6.5 Hz) 1.37–1.54(1.8H, broad) 1.75–1.98(2.2H, m) 2.09(3H, s) 2.40(0.7H, m) 2.58(2H, m) 2.90(2H, m) 3.05(0.3H, m) 3.30(0.2H, broad) 1.95(1H, broad) 2.09(2H, s) 3.98(3H, s) 3.99(3H, s) 4.59(0.8H, broad) 7.11(4H, m) |

| | | | | |
|---|---|---|---|---|
| 138 | [structure] | 35 mg(27%) | Oil | 428(M + H)+ 1.33–1.92(4.7H, m) 2.09, 2.08(total 3H, both s) 2.61 (2H, m) 2.92(2H, m) 3.02–3.89(5.3H, m) 3.81(2H, s) 3.98(3H, s) 3.99(3H, s) 7.11(4H, m) |
| 139 | [structure] | 27 mg(21%) | Oil | 427(M + H)+ 2.08(3H, s) 2.28(5H, s) 2.34(2H, m) 2.58(2H, m) 2.91(2H, m) 3.40(2H, m) 3.63(2H, broad) 3.81(2H, s) 3.98(3H, s) 3.99(3H, s) 7.11(4H, s) |
| 140 | [structure] | 140 mg(95%) | Oil | 491(M + H)+ 1.86(3H, s), 2.07(3H, s), 2.65(2H, m), 3.01(2H, m), 3.23(3H, s), 3.81(2H, s), 3.98(6H, s), 7.12(6H, m), 7.36(1H, broad s), 7.49(2H, m) |
| 141 | [structure] | 114 mg(76%) | Oil | 501(M + H)+ 2.08(3H, s), 2.40(2H, m), 2.46(2H, m), 2.57(4H, m), 2.91(2H, m), 3.42(2H, s), 3.60–3.71(8H, m), 3.81(2H, s), 3.98(3H, s), 3.99(3H, s), 7.11(4H, m) |

| | | | | |
|---|---|---|---|---|
| 142 | [structure] | 44 mg(33%) | Oil | 441(M + H)+ 2.08(3H, s), 2.62(2H, m), 2.93(2H, m), 3.15–3.65(8H, m), 3.80(2H, s), 3.98(3H, s), 3.99(3H, s), 7.11(4H, m), 8.06(1H, s) |
| 143 | [structure] | 80 mg(59%) | Oil | 455(M + H)+ 2.08(3H, s), 2.11(3H, s), 2.61(2H, m), 2.93(2H, m), 3.29–3.65(8H, m), 3.81(2H, s), 3.99(6H, s), 7.11(4H, m) |
| 144 | [structure] | 57 mg(42%) | Oil | 455(M + H)+ 1.25–1.92(4H, m), 2.09(3.8H, m), 2.38(0.7H, m), 2.53–2.72(2.5H, m), 2.90(2H, m), 3.30–3.42(1.4H, m), 3.66–3.71(0.7H, m), 3.81(3H, m), 3.97, 3.98, 3.99, 4.00(total 6H, all s), 4.51(0.2H, broad s), 5.30(1H, broad s), 5.80(0.2H, broad s), 6.47(0.6H, broad s), 7.10(4H, m) |
| 145 | [structure] | 102 mg(74%) | Oil | 460(M + H)+ 1.85(2H, m), 2.07(3H, s), 2.57(2H, broad), 2.77(2H, m), 2.93(2H, m), 3.73(2H, m), 3.79(2H, s), 3.98(3H, s), 3.99(3H, s), 6.98–7.16(4H, m) |
| 146 | [structure] | 110 mg(76%) | Oil | 484(M + H)+ 1.25(3H, t, J=7.1 Hz), 1.55–1.64(2H, m), 1.83–1.94(2H, m), 2.08(3H, s), 2.49(1H, m), 2.58(2H, m), 2.80(1H, m), 2.91(2H, m), 3.03(1H, m), 3.75(1H, m), 3.81(2H, s), 3.98(3H, s), 3.99(3H, s), 4.14(2H, q, J=7.1 Hz), 4.42(1H, m), 7.11(4H, m) |

| | | | | |
|---|---|---|---|---|
| 147 | (structure) | 91 mg(63%) | Oil | 485(M + H)+ 1.27(3H, t, J=7.1 Hz), 2.08(3H, s), 2.59(2H, m), 2.92(2H, m), 3.36(2H, m), 3.44(2H, m), 3.60(2H, m), 3.81(2H, s), 3.98(3H, s), 3.99(3H, s), 4.15(2H, q, J=7.1 Hz), 7.11(4H, m) |
| 148 | (structure) | 90 mg(62%) | Oil | 489(M + H)+ 2.07(3H, s), 2.63(2H, m), 2.94(2H, m), 3.06(2H, m), 3.12(2H, m), 3.54(2H, m), 3.80(4H, m), 3.98(3H, s), 3.99(3H, s), 6.91(3H, m), 7.11(4H, m), 7.28(2H, m) |
| 149 | (structure) | 107 mg(71%) | Oil | 502(M + H)+ 0.98-1.17(2H, m), 1.64-1.73(3H, m), 2.08(3H, s), 2.47-2.58(5H, m), 2.86-2.92(3H, m), 3.76(1H, m), 3.81(2H, s), 3.98(3H, s), 3.99(3H, s), 4.61(1H, m), 7.08-7.30(9H, m) |
| 150 | (structure) | 76 mg(52%) | Oil | 490(M + H)+ 2.07(3H, s), 2.63(2H, m), 2.95(2H, m), 3.50(6H, m), 3.75(2H, m), 3.80(2H, s), 3.98(3H, s), 3.99(3H, s), 6.65(2H, m), 7.11(4H, m), 7.50(1H, m), 8.18(1H, m) |

| | | | | |
|---|---|---|---|---|
| 151 | [structure] | 74 mg (48%) | Powder | 486(M + H)+ 1.70–1.79(4H, m), 2.00(1H, m), 2.07(3H, s), 2.63(2H, m), 2.94(2H, m), 3.09(1H, m), 3.41–3.48(1H, m), 3.66(1H, m), 3.79(2H, s), 3.98(6H, s), 4.59(1H, m), 7.12(4H, m), 7.28–7.45(5H, m) |
| 152 | [structure] | 107 mg (70%) | Oil | 503(M + H)+ 2.08(3H, s) 2.32–2.41(4H, m) 2.57(2H, m) 2.91(2H, m) 3.38(2H, m) 3.49(2H, s) 3.62(2H, m) 3.81(2H, s) 3.98(3H, s) 3.99(3H, s) 7.10(4H, m) 7.26–7.34(5H, m) |
| 153 | [structure] | 118 mg (80%) | Oil | 491(M + H)+ 2.07(3H, s) 2.64(2H, m) 2.95(2H, m) 3.44(2H, m) 3.71(4H, m) 3.79(4H, m) 3.98(6H, s) 6.54(1H, m) 7.12(4H, m) 8.32(2H, d, J=4.6 Hz) |
| 154 | [structure] | 140 mg (86%) | Oil | 520(M + H – H2O)+ 1.68–1.79(4H, m), 1.94(1H, m), 2.07(3H, s), 2.62(2H, m), 2.94(2H, m), 3.07(1H, m), 3.36–3.45(1H, m), 3.65(1H, m), 3.79(2H, s), 3.98(6H, s), 4.59(1H, m), 7.11(4H, m), 7.35(4H, m) |

| | | | | |
|---|---|---|---|---|
| 155 | [structure] | 81 mg(63%) | Oil | 428(M + H)⁺ 1.27(1H, m) 1.41(1H, m) 1.75(1H, broad) 1.85(1H, broad) 2.09(3H, s) 2.59(2H, m) 2.92(2H, m) 3.12(2H, m) 3.63(1H, broad) 3.81(2H, s) 3.86(1H, m) 3.99(6H, s) 4.12(1H, broad) 7.11(4H, m) |
| 156 | [structure] | 77 mg(58%) | Oil | 442(M + H)⁺ 1.12(3H, d, J=6.3 Hz) 1.18(3H, d, J=6.2 Hz) 2.09(3H, s) 2.28(1H, m) 2.57(2H, m) 2.68(1H, m) 2.92(2H, m) 3.31(1H, broad) 3.43–3.52(2H, broad) 3.81(2H, s) 3.98(3H, s) 3.99(3H, s) 4.45(1H, d, J=13.2 Hz) 7.11(4H, s) |
| 157 | [structure] | 62 mg(47%) | Oil | 442(M + H)⁺ 1.18–1.79(5.4H, broad) 2.08, 2.09(total 3H, both s) 2.33(0.5H, broad) 2.61 (2H, m) 2.80(0.8H, m) 2.92(2H, m) 3.26–3.53(3.9H, m) 3.76(1H, m) 3.81(2H, s) 3.98(3H, s) 3.99(3H, s) 4.32(0.4, broad) 7.11(4H, m) |
| 158 | [structure] | 59 mg(50%) | Oil | 396(M + H)⁺ 2.08(3H, s) 2.53(2H, m) 2.96(2H, m) 3.81 (2H, s) 3.98(3H, s) 3.99(3H, s) 4.13(2H, broad) 4.23(2H, broad) 5.75(1H, m) 5.86(1H, m) 7.112(4H, m) |
| 159 | [structure] | 60 mg(49%) | Oil | 410(M + H)⁺ 2.08(3H, s) 2.11(2H, broad) 2.59(2H, m) 2.93(2H, m) 3.44(1H, m) 3.63(1H, m) 3.80(2H, s) 3.84(1H, m) 3.98(3H, s) 3.99(3H, s) 4.05(1H, m) 5.63(1H, broad) 5.83(1H, m) 7.11(4H, m) |

| | Structure | Yield | Form | MS / NMR |
|---|---|---|---|---|
| 160 | [2,3-dimethoxy-5-methyl-1,4-benzoquinone with CH2-phenyl-CH2CH2-C(O)-N(piperidine-2-ethanol-OH)] | 24 mg (18%) | Oil | 456(M + H)+ 1.33(1H, m) 1.54–1.70(6H, m) 1.89(1H, m) 2.08(3H, s) 2.63(2H, m) 2.83–2.94(3H, m) 3.20(1H, m) 3.55–3.65(2H, m) 3.81 (2H, s) 3.98(3H, s) 3.99(3H, s) 4.85(1H, broad) 7.11(4H, m) |
| 161 | [2,3-dimethoxy-5-methyl-1,4-benzoquinone with CH2-phenyl-CH2CH2-C(O)-N(piperidine-4-ethanol-OH)] | 74 mg (54%) | Oil | 456(M + H)+ 0.91–1.35(3H, broad) 1.51(2H, m) 1.60–1.73(3H, m) 2.08(3H, s) 2.54(3H, m) 2.91(3H, m) 3.69(2H, m) 3.74(1H, m) 3.81(2H, s) 3.98(3H, s) 3.99(3H, s) 4.61(1H, Broad) 7.10(4H, m) |
| 162 | [2,3-dimethoxy-5-methyl-1,4-benzoquinone with CH2-phenyl-CH2CH2-C(O)-N(piperazine-ethanol-OH)] | 40 mg (29%) | Oil | 457(M + H)+ 2.08(3H, s) 2.38(2H, m) 2.45(2H, m) 2.52–2.60(4H, m) 2.92(2H, m) 3.40(2H, m) 3.63(4H, m) 3.81(2H, s) 3.98(3H, s) 3.99(3H, s) 7.10(4H, m) |
| 163 | [2,3-dimethoxy-5-methyl-1,4-benzoquinone with CH2-phenyl-CH2CH2-C(O)-N(piperazine-2-methoxyphenyl)] | 80 mg (51%) | Oil | 519(M + H)+ 2.10(3H, s) 2.63(2H, m) 2.93–3.01(6H, m) 3.58(2H, m) 3.80(4H, s) 3.87(3H, s) 3.98(3H, s) 3.99(3H, s) 6.87–6.93(3H, m) 7.03(1H, m) 7.12(4H, m) |
| 164 | [2,3-dimethoxy-5-methyl-1,4-benzoquinone with CH2-phenyl-CH2CH2-C(O)-N(piperazine-4-fluorophenyl)] | 88 mg (58%) | Oil | 507(M + H)+ 2.07(3H, s) 2.63(2H, m) 2.95(4H, m) 3.03(2H, m) 3.53(2H, m) 3.77(2H, m) 3.80(2H, s) 3.98(3H, s) 3.99(3H, s) 6.86(2H, m) 6.98(2H, m) 7.11(4H, m) |

-continued

| | | | | |
|---|---|---|---|---|
| 165 | [structure] | 112 mg(76%) | Oil | 495(M + H)⁺ 1.38–1.88(10H, m), 2.08(3H, s), 2.47–2.60(8H, m), 2.90(3H, m), 3.80(2H, s), 3.84(1H, m), 3.98(3H, s), 3.99(3H, s), 4.70(1H, m), 7.11(4H, m) |
| 166 | [structure] | 64 mg(50%) | Oil | 428(M + H)⁺ 1.55(1H, m) 1.78(1H, m), 1.86(1H, m), 2.00(1H, m) 2.08(3H, s) 2.57(2H, m) 2.94(2H, m) 3.35(2H, m) 3.54(1H, m), 3.65(1H, m) 3.81(2H, s) 3.98(3H, s) 3.99(3H, s) 4.21(1H, m) 5.06(1H, m) 7.11(4H, m) |
| 167 | [structure] | 98 mg(63%) | Oil | 520(M + H)⁺ 2.08(3H, s) 2.66(2H, m) 2.73(2H, m) 2.93(2H, m) 3.58(1.2H, m) 3.78–3.86(9.2H, s) 3.98(3H, s) 3.99(3H, s), 4.46(0.8H, s) 4.66(1.2H, s) 6.49, 6.60, 6.63(total 2H, all s) 7.10(4H, m) |
| 168 | [structure] | 83 mg(52%) | Oil | 530(M + H)⁺ 1.67(1H, m) 1.91(3H, s) 2.06(3H, s) 2.08(1H, m) 2.36(2H, m) 2.57(2H, m) 2.89(2H, m) 3.08(1H, m) 3.33(1H, m) 3.54(1H, m) 3.75(2H, s) 3.98(3H, s) 3.99(3H, s) 4.23(1H, m) 7.09(4H, m) 7.24–7.31(3H, m), 7.38(2H, m) |

| | | | | |
|---|---|---|---|---|
| 169 | [structure] | 95 mg(69%) | Oil | 460(M + H)+ 2.08(3H, s) 2.67(2H, m) 2.82(2H, m) 2.95(2H, m) 3.59(1.2H, m) 3.81(2.8H, m) 3.98(3H, s) 3.99(3H, s) 4.53(0.8H, s) 4.73(1.2H, s) 7.01–7.20(8H, m) |
| 170 | [structure] | 98 mg(77%) | Oil | 426(M + H)+ 2.08(3H, s) 2.26(2H, m) 2.42(2H, m) 2.68(2H, m) 2.94(2H, m) 3.64(2H, m) 3.80(2H, m) 3.87(2H, m) 3.99(6H, s) 7.12(4H, m) |
| 171 | [structure] | 80 mg(67%) | Powder | 400(M + H)+ 0.82(6H, d, J=6.6 Hz) 1.67(1H, m) 2.07(3H, s) 2.44(2H, m) 2.91(2H, m) 3.03(2H, m) 3.80(2H, s) 3.98(3H, s) 3.99(3H, s) 5.31(1H, broad) 7.09(4H, s) |
| 172 | [structure] | 107 mg(89%) | Powder | 400(M + H)+ 1.27(9H, s) 2.07(3H, s) 2.33(2H, m) 2.88(2H, m) 3.81(2H, s) 3.98(3H, s) 3.99(3H, s) 5.07(1H, broad) 7.09(4H, s) |
| 173 | [structure] | 86 mg(69%) | Powder | 414(M + H)+ 0.88(6H, d, J=6.6 Hz) 1.31(2H, m) 1.52(1H, m) 2.07(3H, s) 2.41(2H, m) 2.91(2H, m) 3.22(2H, m) 3.80(2H, s) 3.98(3H, s) 3.99(3H, s) 5.24(1H, broad) 7.09(4H, s) |

| # | Structure | Yield | Form | MS / NMR |
|---|---|---|---|---|
| 174 | (quinone with 2 OMe, Me, CH2-C6H4-CH2CH2C(O)NH-pentyl) | 79 mg (60%) | Powder | 428(M + H)+ 0.88(3H, m) 1.27(6H, broad) 1.42(2H, broad) 2.07(3H, s) 2.41(2H, m) 2.91(2H, m) 3.20(2H, m) 3.80(2H, s) 3.98(3H, s) 3.99(3H, s) 5.29(1H, broad) 7.09(4H, s) |
| 175 | (quinone with 2 OMe, Me, CH2-C6H4-CH2CH2C(O)NH-cyclohexyl) | 65 mg (50%) | Powder | 426(M + H)+ 0.99(2H, broad) 1.12(1H, broad) 1.32(2H, broad) 1.61(3H, broad) 1.81(2H, broad) 2.07(3H, s) 2.39(2H, m) 2.90(2H, m) 3.72(1H, m) 3.81(2H, s) 3.98(3H, s) 3.99(3H, s) 5.11(1H, broad) 7.09(4H, s) |
| 176 | (quinone with 2 OMe, Me, CH2-C6H4-CH2CH2C(O)NH-cyclopentyl) | 67 mg (54%) | Powder | 412(M + H)+ 1.23(2H, m) 1.56(4H, m) 1.91(2H, m) 2.07(3H, s) 2.38(2H, m) 2.90(2H, m) 3.81(2H, s) 3.98(3H, s) 3.99(3H, s) 4.15(1H, m) 5.18(1H, broad) 7.09(4H, s) |
| 177 | (quinone with 2 OMe, Me, CH2-C6H4-CH2CH2C(O)NH-cyclopropyl) | 61 mg (53%) | Powder | 384(M + H)+ 0.37(2H, m) 0.72(2H, m) 2.08(3H, s) 2.37(2H, m) 2.64(1H, m) 2.89(2H, m) 3.81(2H, s) 3.98(3H, s) 3.99(3H, s) 5.39(1H, broad) 7.08(4H, s) |
| 178 | (quinone with 2 OMe, Me, CH2-C6H4-CH2CH2C(O)NH-CH2-cyclopropyl) | 66 mg (55%) | Powder | 398(M + H)+ 0.13(2H, m) 0.45(2H, m) 0.86(1H, m) 2.08(3H, s) 2.44(2H, m) 2.92(2H, m) 3.06(2H, m) 3.81(2H, s) 3.98(3H, s) 3.99(3H, s) 5.39(1H, broad) 7.10(4H, s) |

| | | | | |
|---|---|---|---|---|
| 179 | 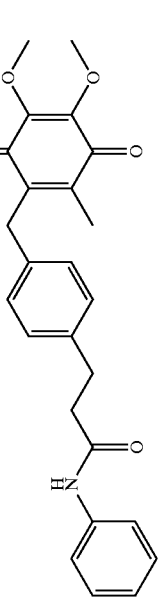 | 65 mg(52%) | Powder | 420(M + H)⁺ 2.08(3H, s) 2.62(2H, m) 3.01(2H, m) 3.81(2H, s) 3.98(6H, s) 6.96(1H, broad) 7.12(5H, m) 7.30(2H, m) 7.42(2H, d, J=8.0 Hz) |
| 180 | 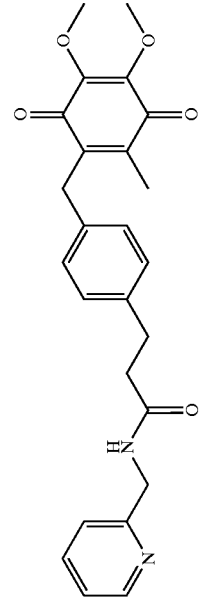 | 73 mg(56%) | Oil | 435(M + H)⁺ 2.07(3H, s) 2.55(2H, m) 2.96(2H, m) 3.80(2H, s) 3.98(3H, s) 3.99(3H, s) 4.54(2H, d, J=4.9 Hz) 6.65(1H, broad) 7.10(4H, m) 7.20(2H, m) 7.65(1H, m) 8.51(1H, m) |
| 181 | 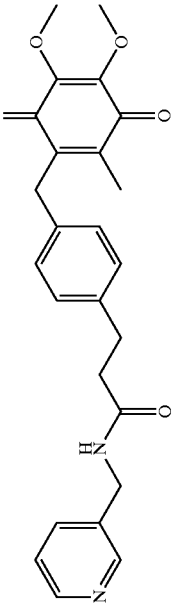 | 45 mg(35%) | Oil | 435(M + H)⁺ 2.08(3H, s) 2.49(2H, m) 2.94(2H, m) 3.81(2H, s) 3.99(5H, s) 4.41(2H, d, J=5.9 Hz) 5.67(1H, broad) 7.08(4H, s) 7.24(1H, m) 7.50(1H, d, J=7.6 Hz) 8.44(1H, s) 8.51(1H, d, J=4.7 Hz) |
| 182 | 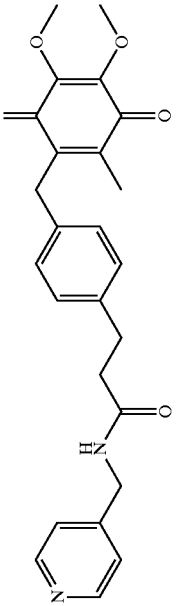 | 67 mg(51%) | Powder | 435(M + H)⁺ 2.08(3H, s) 2.54(2H, m) 2.96(2H, m) 3.82(2H, s) 3.99(6H, s) 4.41(2H, d, J=6.1 Hz) 5.75(1H, broad) 7.04(2H, d, J=5.5 Hz), 7.10(4H, s) 8.51(2H, d, J=5.9 Hz) |

| | | | | |
|---|---|---|---|---|
| 183 | [structure] | 83 mg(65%) | Oil | 426(M + H)+ 1.51(4H, broad) 1.66(4H, broad) 2.08(3H, s) 2.57(2H, m) 2.93(2H, m) 3.36(2H, m) 3.52(2H, m) 3.81(2H, s) 3.98(3H, s) 3.99(3H, s) 7.11(4H, m) |
| 184 | [structure] | 16 mg(56%) | Powder | (DMSO-d6) 1.96(3H, s), 2.58(2H, m), 2.83(2H, m), 3.74(2H, s), 3.87(3H, s), 3.88(3H, s), 6.78(1H, m), 6.99(1H, s), 7.07(2H, m), 7.14(2H, m), 7.55(1H, m), 9.77(1H, s) |
| 185 | [structure] | 116 mg(87%) | Oil | 450(M + H)+ 2.07(3H, s) 2.67(2H, m) 3.01(2H, m) 3.81(2H, s) 3.84(3H, s) 3.98(3H, s) 3.99(3H, s) 6.85(1H, d, J=8.0 Hz) 6.96(1H, m) 7.02(1H, d, J=8.1 Hz) 7.15(2H, d, J=8.0 Hz) 7.69(1H, broad) 8.37(1H, d, J=7.8 Hz) |
| 186 | [structure] | 112 mg(83%) | Oil | 450(M + H)+ 2.07(3H, s) 2.61(2H, m) 3.00(2H, m) 3.79(3H, s) 3.81(2H, s) 3.98(6H, s) 6.65(1H, broad) 6.85(1H, broad) 6.96(1H, broad) 7.10–7.20(5H, m) 7.25(1H, broad) |

-continued

| | | | | |
|---|---|---|---|---|
| 187 | structure | 108 mg(76%) | Oil | 480(M + H)+ 2.07(3H, s), 2.64(2H, m), 3.00(2H, m), 3.79(3H, s), 3.81(3H, s), 3.83(2H, s), 3.98(3H, s), 3.99(3H, s), 6.45(2H, m), 7.13(4H, m), 7.47(1H, broad s), 8.23(1H, m) |
| 188 | structure | 103 mg(77%) | Powder | 451(M + H)+ 2.08(3H, s) 2.62(2H, m) 3.00(2H, m) 3.81(2H, s) 3.90(3H, s) 3.98(6H, s) 6.71 (1H, d, J=8.9 Hz) 6.87(1H, broad) 7.13(4H, m) 7.81(1H, m) 8.02(1H, m) |
| 189 | structure | 84 mg(64%) | Powder | 436(M + H)+ (DMSO-d6) 1.96(3H, s), 2.83(2H, m), 3.74(2H, s), 3.87(3H, s) 3.88(3H, s), 6.66(2H, m), 7.07(1H, s), 7.07(2H, m), 7.13(2H, m), 9.13(1H, s), 9.61(1H, s) |

Reference Production Example 1

2-(tert-Butoxycarbonylaminol-5-hydroxyindan

Method 1 a) 6-methoxy-1-indanone (8.6 g, 53 mmol) (see J. Org. Chem., 35, 647 (1970)) was added to methanol (500 ml), then heated to 40° C., and isoamyl nitrite (15 ml, 110 mmol) and concentrated hydrochloric acid (8.5 ml) were added thereto followed by stirring for 2 hours. The crystals that deposited on cooling the reaction mixture were filtered to obtain 6-methoxy-2-oxyimino-1-indanone (5.5 g, 29 mmol) having the following physical properties:

$^1$H NMR (400 MHz, DMSO-d$_6$): δ 3.69 (2H, s), 3.83 (3H, s), 7.21 (1H, d, J=2 Hz), 7.32 (1H, dd, J=2 Hz, 8 Hz), 7.53 (1H, d, J=8 Hz), 12.58 (1H, br. s).

b) 6-methoxy-2-oxyimino-1-indanone (5.5 g, 29 mmol) was suspended in acetic acid (85 ml), and palladium carbon (10%, 2.0 g), palladium chloride (60 mg), and concentrated sulfuric acid (4 ml) were added thereto. The mixture was then stirred under a hydrogen atmosphere at 5 kg/cm$^2$ for 6 hours. After the filtrate obtained by filtering the reaction mixture was concentrated under reduced pressure, it was neutralized with 10% sodium hydroxide and extracted with chloroform. After the organic layer was dried over anhydrous sodium sulfate, the solvent was distilled off under reduced pressure to obtain 2-amino-5-methoxyindan as a crude product. This was used as a raw material for the subsequent reaction without further purification.

c) To crude 2-amino-5-methoxyindan were added 30% hydrobromic acid-acetic acid (6.0 ml) and an aqueous solution of 48% hydrobromic acid (4.0 ml), and then the mixture was heated to reflux for 2 hours. The solvent was distilled off under reduced pressure, dioxane and toluene were added thereto, and the solvent was distilled off again under reduced pressure. The residue thus obtained was dissolved in dioxane (100 ml) and water (50 ml). The reaction mixture was neutralized with triethylamine (about 10 ml), di-tert-butyl dicarbonate (7.0 g, 32 mmol) was added thereto, and the mixture was stirred at room temperature for 2 hours. To the reaction mixture was added ethyl acetate, the organic layer was washed with an aqueous solution of saturated potassium hydrogensulfate, brine, an aqueous solution of saturated sodium hydrogencarbonate, and then was dried over anhydrous sodium sulfate. The residue obtained by distilling off the solvent under reduced pressure was purified by silica gel chromatography (hexane:ethyl acetate=4:1) to obtain the title compound (2.5 g, 10 mmol) having the following physical properties:

$^1$H NMR (400 MHz, CDCl$_3$): δ 1.54 (9H, s), 2.70 (2H, dt, J=5 Hz, 12 Hz), 3.20 (2H, m), 4.43 (1H, br. s), 4.75 (1H, br. s), 5.26 (1H, br. s), 6.64 (1H, dd, J=2 Hz, 18 Hz), 6.69 (1H, s), 7.03 (1H, d, J=8 Hz).

Method 2 a) Using 5-methoxy-1-indanone (5.0 g, 31 mmol) in stead of 6-methoxy-1-indanone, methanol (100 ml), isoamyl nitrite (1.9 ml, 14 mmol) and concentrated hydrochloric acid (1.2 ml), a similar procedure to a) in Method 1 was carried out. The product obtained was purified by silica gel chromatography (hexane:ethyl acetate=3:1) to obtain 5-methoxy-2-oxyimino-1-indanone (4.5 g, 23 mmol) having the following physical properties:

$^1$H NMR (400 MHz, DMSO-d$_6$): δ 3.73 (2H, s), 3.89 (3H, s), 7.02 (1H, dd, J=2 Hz, 8 Hz), 7.15 (1H, d, J=2 Hz), 7.69 (1H, d, J=8 Hz), 12.45 (1H, br. s).

b) 5-methoxy-2-oxyimino-1-indanone (440 mg, 2.3 mmol) was suspended in acetic acid (6.5 ml) and palladium carbon (10%, 170 mg), palladium chloride (20 mg), and concentrated sulfuric acid (4.4 ml) were added thereto. A similar procedure to b) in Method 1 was carried out to obtain 2-amino-5-methoxyindan (300 mg) as a crude product. This was used without further purification as a raw material for the subsequent reaction.

c) After crude 2-amino-5-methoxyindan was demethylated using 30% hydrobromic acid-acetic acid (1.8 ml) and an aqueous solution of 48% hydrobromic acid (1.2 ml), a similar procedure to c) in Method 1 was carried out using dioxane (6.2 ml), water (3.1 ml), triethylamine; (about 0.55 ml), and di-tert-butyl dicarbonate (440 mg, 2.0 mmol) to obtain the title compound (300 mg, 1.1 mmol).

Reference Production Example 2

2-(tert-Butoxycarbonylamino)-5-[(E)-2-(4-methylphenyl)ethenyl]indan a) To a solution of 2-(tert-butoxycarbonylamino)-5-hydroxyindan (270 mg, 1.1 mmol) in pyridine (0.5 ml) was added trifluoromethanesulfonic anhydride (360 mg, 1.3 mmol) under ice cooling, and the mixture was stirred at room temperature for 30 minutes. The reaction mixture was diluted with ethyl acetate, and the organic layer was washed with an aqueous solution of saturated potassium hydrogensulfate, brine, an aqueous solution of saturated sodium hydrogencarbonate, and then was dried over anhydrous sodium sulfate. The residue obtained by distilling off the solvent under reduced pressure was purified by silica gel chromatography (hexane:ethyl acetate=4:1) to obtain 2-(tert-butoxycarbonylamino)-5-trifluoromethanesulfonyloxyindan (320 mg, 0.84 mmol) having the following physical properties:

$^1$H NMR (400 MHz, CDCl$_3$): δ 1.45 (9H, s), 2.80 (2H, m), 3.30 (2H, m), 4.50 (1H, br. s), 4.70 (1H, br. s), 7.06 (1H, d, J=8 Hz), 7.11 (1H, s), 7.25 (1H, d, J=8 Hz). IR (KBr): ν 3350, 2980, 1680, 1540, 1440, 1250, 1210 cm$^{-1}$.

b) By adding catechol borane (0.50 ml, 4.7 mmol) to 4-ethynyl toluene (540 mg, 4.7 mmol), and stirring the mixture at 70° C. for 2 hours, a catechol borane derivative was obtained as a solid form which was used without purification as a raw material for the subsequent reaction. To the catechol borane derivative (240 mg, 1.0 mmol) was added ice water (5 ml), and then was stirred at room temperature for 2 hours. The reaction mixture was extracted with ethyl acetate, and the organic layer was washed with water and dried over anhydrous magnesium sulfate. The solvent was distilled off under reduced pressure to obtain (E)-2-(4-methylphenyl)ethenylboronic acid (220 mg) as a crude product.

c) 2-(tert-butoxycarbonylamino)-5-trifluoromethanesulfonyloxyindan (260 mg, 0.69 mmol), (E)-2-(4-methylphenyl)ethenylboronic acid (180 mg), toluene (7 ml), Pd(PPh$_3$)$_4$ (30 mg, 0.026 mmol), 2M sodium carbonate (0.99 ml), ethanol (3.0 ml), and lithium chloride (64 mg, 1.5 mmol) were heated to reflux for 5 hours. The reaction mixture was diluted with ether, washed with water, dried, and then the solvent was distilled off under reduced pressure. The residue obtained was purified by silica gel chromatography (hexane:ethyl acetate=4:1) to obtain the title compound (190 mg, 0.54 mmol) having the following physical properties:

$^1$H NMR (400 MHz, CDCl$_3$): δ 1.45 (9H, 8), 2.35 (3H, s), 2.80 (2H, m), 3.30 (2H, m), 4.50 (1H, br. s), 4.80 (1H, br. s), 7.04–7.11 (2H, m), 7.16 (3H, m), 7.26–7.31 (2H, m), 7.39 (2H, m).

Reference Production Example 3

2-(tert-Butoxycarbonylaminol-5-methoxycarbonylindan

A mixture of 2-(tert-butoxycarbonylamino)-5-[(E)-2-(4-methylphenyl)ethenyl]indan (190 mg, 0.54 mmol) synthesized in Reference Production Example 2, osmium tetraoxide (on poly (4-vinylpyridine), 140 mg), sodium metaperiodate (450 mg, 2.1 mmol), dioxane (3.8 ml) and water (0.8 ml) was vigorously stirred at room temperature. The reaction mixture was diluted with ethyl acetate, the organic layer was washed with water, dried, and then the solvent was distilled off under reduced pressure to obtain an aldehyde mixture (170 mg).

Subsequently, the aldehyde mixture (170 mg) was dissolved in methanol (7.0 ml), to which sodium cyanide (270 mg, 5.5 mmol), acetic acid (0.10 ml), and manganese dioxide (1.87 g, 22 mmol) were added, and the reaction mixture was stirred at room temperature for 30 minutes. Methanol was added thereto, and the reaction mixture was filtered, concentrated, and after the addition of water, extracted with methylene chloride. The organic layer was dried, and the solvent was distilled off under reduced pressure to obtain a residue, which was purified by silica gel chromatography (hexane:ethyl acetate=4:1) to obtain the title compound.(76 mg, 0.26 mmol) having the following physical properties:

$^1$H NMR (400 MHz, CDCl$_3$): δ 1.45 (9H, s), 2.82 (2H, m), 3.31 (2H, m), 3.90 (3H, s), 4.49 (1H, br.), 4.72 (1H, br.), 7.27 (1H, m), 7.87 (1H, m), 7.88 (1H, m).

Reference Production Example 4

2-(tert-Butoxycarbonylamino)-5-carboxyindan

Method 1

2-(tert-butoxycarbonylamino)-5-methoxycarbonylindan (76 mg, 0.26 mmol) synthesized in Reference Production Example 3 was dissolved in methanol (2 ml), to which an aqueous solution of 1N sodium hydroxide (0.29 ml, 0.29 mmol) was added and the mixture was heated to reflux for 1.5 hours. After the reaction mixture was diluted with water and washed with ethyl acetate, the aqueous layer was acidified with an aqueous solution of saturated sodium hydrogensulfate and extracted with ethyl acetate. After the organic layer was dried, the solvent was distilled off under reduced pressure to obtain the title compound (58 mg, 0.21 mmol) having the following physical properties:

$^1$H NMR (400 MHz, CDCl$_3$): δ1.45 (9H, s), 2.85 (2H, m), 3.33 (2H, m), 4.50 (1H, br.), 4.75 (1H, br.), 7.30 (1H, m), 7.93 (1H, m), 7.94 (1H, m).

Method 2 a) 2-aminoindan (6.0 g, 45 mmol) was dissolved in dry pyridine (7 ml), to which acetic anhydride (4.5 ml, 47.3 mmol) was added dropwise while cooling in ice water. After the reaction mixture was returned to room temperature and stirred for 20 minutes, water was added. The precipitate that deposited was filtered to obtain 2-acetamidoindan (5.6 g, 32 mmol).

b) To a solution of anhydrous aluminum chloride (3.4 g, 25.5 mmol) in 1,2-dichloroethane (20 ml) cooled in ice water was added dropwise acetyl chloride (1.11 ml, 15.5 mmol) under an argon atmosphere. After the addition was complete, a solution of 2-acetamidoindan (5.6 g, 32 mmol) in 2-dichloroethane (40 ml), was added. The reaction mixture was allowed to react at room temperature for 2.5 hours, and was cooled again in ice water, to which ice was carefully added and the reaction mixture was extracted with methylene chloride. The organic layer was washed with a 1N potassium hydroxide solution and .brine, and dried over anhydrous sodium sulfate. The solvent was distilled off under reduced pressure to obtain 2-acetamide-5-acetylindan (2.1 g, 9.8 mmol) having the following physical properties:

$^1$H NMR (400 MHz, CDCl$_3$): δ 1.95 (3H, s), 2.58 (3H, s), 2.82–2.87 (2H, m), 3.32–3.38 (2H, m), 4.77 (1H, m), 5.65 (1H, broad), 7.31 (1H, d, J=7.8 Hz), 7.81 (1H, d, J=7.8 Hz), 7.82 (1H, s). MS (FAB): m/z 218 (M+H)$^+$.

c) An aqueous solution (60 ml) of sodium hydroxide (5.6 g, 140 mmol) was cooled to −50° C., to which bromine (2.67 ml, 51.7 mmol) was added dropwise. Then a solution of 2-acetamide-5-acetylindan (2.1 g, 9.8 mmol) in dioxane (70 ml) was added and stirred at room temperature for 3 hours. The reaction mixture was cooled in ice water, and sodium hydrogen sulfite was added thereto to decompose an excess of bromine. After the reaction mixture was washed with ether, it was acidified by adding concentrated hydrochloric acid, which was then extracted with methylene chloride. The organic layer was allowed to stand, and the precipitate that deposited was filtered to obtain 2-acetamide-5-carboxyindan (2.0 g, 8.9 mmol) having the following physical properties:

$^1$H NMR (400 MHz, DMSO-d$_6$): δ 1.77 (3H, s), 2.77–2.82 (2H, m), 3.17–3.23 (2H, m), 4.76 (1H, m), 7.32 (1H, d, J=8.7 Hz), 7.75 (1H, d, J=8.7 Hz), 7.78 (1H, s), 8.12 (1H, d, J=6.4 Hz), 12.70 (1H, broad). MS (FAB): m/z 220 (M+H)$^+$.

d) 2-acetamide-5-carboxyindan (2.0 g, 8.9 mmol) was suspended in water (12 ml) and concentrated hydrochloric acid (12 ml), and the suspension was heated to reflux for 7 hours. After the reaction mixture was washed with ether, water was distilled off under reduced pressure to obtain 2-amino-5-carboxyindan hydrochloride (1.9 g, 8.8 mmol) having the following physical properties:

$^1$H NMR (400 MHz, DMSO-d$_6$): δ 3.04 (2H, m), 3.33 (2H, m), 4.03 (1H, m), 7.39 (1H, m), 7.80 (1H, m), 7.84 (1H, m), 8.29 (3H, br.), 12.82 (1H, br.). MS (FAB): m/z 178 (M+H)$^+$.

e) A mixture of 2-amino-5-carboxyindan hydrochloride (1.9 g, 8.7 mmol), an aqueous solution of 1N sodium hydroxide (17.4 ml), dioxane (38 ml), water (19 ml) and di-tert-butyldicarbonate (2.1 g, 9.6 mmol) was stirred at room temperature for 30 minutes. The reaction mixture was extracted with ethyl acetate, the organic layer was dried, and the solvent was distilled off under reduced pressure to obtain the title compound (1.8 g, 6.5 mmol).

Reference Production Example 5

2-(tert-Butoxycarbonylamino)-4-hydroxyindan a) Using 4-methoxy-1-indanone (1.0 g, 6.2 mmol) in stead of 6-methoxy-1-indanone, methanol (20 ml), isoamyl nitrite (0.81 ml, 5.9 mmol) and concentrated hydrochloric acid (0.25 ml), a similar procedure to a) in Method 1 of Reference Production Example 1 was carried out to obtain 4-methoxy-2-oxyimino-1-indanone (350 mg, 1.8 mmol) having the following physical properties:

$^1$H NMR (400 MHz, DMSO-d$_6$): δ 3.60 (2H, s), 3.90 (3H, s), 7.33 (1H, m), 7.47 (1H, t, J=8 Hz), 7.69 (1H, d, J=8 Hz), 12.70 (1H, br. s). MS (FAB): m/z 192 (M+H)$^+$.

b) 4-methoxy-2-oxyimino-1-indanone (400 mg, 2.1-mmol) was suspended in acetic acid (7.6 ml). Palladium carbon (5%, 200 mg) and concentrated sulfuric acid (0.50 ml) were added thereto, and the mixture was stirred under a hydrogen atmosphere at ordinary pressure for 1.5 hours. Then a similar procedure to b) in Method 1 of Reference Production Example 1 was carried out to obtain 2-amino-4-methoxyindan (290 mg, 1.8 mmol).

$^1$H NMR (400 MHz, DMSO-d$_6$): δ 2.45 (2H, m), 2.98 (2H, m), 3.68 (1H, m), 6.72 (1H, d, J=8 Hz), 6.77 (1H, d, J=8 Hz), 7.09 (1H, t, J=8 Hz); MS (FAB): m/z 164 (M+H)$^+$. IR (KBr): ν 3450, 2940, 1590, 1480, 1260, 1070 cm$^{-1}$.

c) After 2-amino-4-methoxyindan (290 mg, 1.8 mmol) was demethylated using 30% hydrobromic acid-acetic acid (1.8 ml) and an aqueous solution of 48% hydrobromic acid (1.2 ml), a similar procedure to c) in Method 1 of Reference Production Example 1 was carried out using dioxane (5.9 ml), water (3.0 ml), triethylamine (about 0.55 ml), and di-tert-butyldicarbonate (420 mg, 1.9 mmol) to obtain the title compound (110 mg; 0.45 mmol) having the following physical properties:

$^1$H NMR (400 MHz, DMSO-d$_6$): δ 1.39 (1H, s), 2.59 (1H, m), 2.71 (1H, m), 3.04 (2H, m), 4.16 (1H, m), 6.56 (1H, d, J=8 Hz), 6,61 (1H, d, J=7 Hz), 6.93 (1H, t, J=8 Hz), 7.09 (1H, br. s), 9.09 (1H, s). MS (FAB): m/z 250 (M+H)$^+$.

Reference Production Example 6

2-(tert-Butoxycarbonylaminol-4-[(E)-2-(4-methylphenyl)ethenyl]indan a) Using 2-(tert-butoxycarbonylamino)-4-hydroxyindan (110 mg, 0.45 mmol) instead of 2-(tert-butoxycarbonylamino)-5-hydroxyindan, pyridine, (0.5 ml), and trifluoromethanesulfonic anhydride (91 μl, 0.54 mmol), a similar procedure to a) in Reference Production Example 2 was carried out. The product was purified by silica gel chromatography (hexane:ethyl acetate=3:1) to obtain 2-(tert-butoxycarbonylamino)-4-trifluoromethanesulfonyloxyindan (130 mg, 0.35 mmol).

$^1$H NMR (400 MHz, CDCl$_3$): δ 1.45 (9H, s), 2.90 (2H, m), 3.36 (2H, m), 4.52 (1H, br. s), 4.72 (1H, br. s), 7.08 (1H, d, J=7 Hz), 7.25(2H, m). MS (FAB): m/z 382 (M+H)$^+$.

b) Using 2-(tert-butoxycarbonylamino)-4-trifluoromethanesulfonyloxyindan (130 mg, 0.35 mmol), (E)-2-(4-methylphenyl)ethenylboronic acid (110 mg), toluene (3.4 ml), Pd(PPh$_3$)$_4$ (15 mg, 0.013 mmol), an aqueous solution of 2M sodium carbonate (0.5 ml), ethanol (1.6 ml) and lithium chloride (32 mg, 0.75 mmol), a similar procedure to c) in Reference Production Example 2 was carried out. The product obtained was purified by silica gel chromatography (hexane:ethyl acetate=6:1) to obtain the title compound (70 mg, 0.20 mmol) having the following physical properties:

$^1$H NMR (400 MHz, CDCl$_3$): δ 1.45 (9H, s), 2.36 (3H, s), 2.81 (1H, dd, J=5 Hz, 16 Hz), 2.93 (1H, m), 3.30 (1H, dd, J=7 Hz, 16 Hz), 3.42 (1H, dd, J=7 Hz, 16 Hz), 4.50 (1H, br. s), 4.77 (1H, br. s), 7.05 (1H, d, J=12 Hz), 7.12 (1H, d, J=12 Hz), 7.18 (3H, m), 7.42 (3H, m); MS (FAB): m/z 349 (M)$^+$.

Reference Production Example 7

2-(tert-Butoxycarbonylamino)-4-methoxycarbonylindan

Using 2-(tert-butoxycarbonylamino)-4-[(E)-2-(4-methylphenyl)ethenyl]indan (70 mg, 0.20 mmol) synthesized in Reference Production Example 6, osmium tetraoxide (on poly (4-vinylpyridine), 53 mg), sodium metaperiodate (170 mg, 0.79 mmol), dioxane (1.5 ml), and water (0.3 ml.), a similar procedure to Reference Production Example 3 was carried out to obtain an aldehyde mixture (73 mg).

Subsequently, using methanol (3 ml), sodium cyanide (120 mg, 2.4 mmol), acetic acid (44 μl), and manganese dioxide (800 mg, 9.4 mmol), the aldehyde mixture (73 mg) was treated in a similar procedure to Reference Production Example 3. The product obtained was purified by silica gel chromatography (hexane:ethyl acetate=4:1) to obtain the title compound (45 mg, 0.15 mmol) having the following physical properties:

$^1$H NMR (400 MHz, CDCl$_3$): δ 1.45 (9H, s), 2.84 (1H, m), 3.17 (1H, m), 3.30 (1H, m), 3.62 (1H, m), 4.47 (1H, br. s), 4.71 (1H, br. s), 7.24 (1H, m), 7.39 (1H, d, J=8 Hz), 7.85 (1H, d, J=8 Hz). MS (FAB): m/z 292 (M+H)$^+$, 236 (M+H-56)$^+$.

Production Example 190

4-(2-Indanylamino)-5-methylthieno[2,3-d]pyrimidine 4-chloro-5-methylthieno[2,3-d]pyrimidine (92 mg, 0.50 mmol) (see J. Pharm. Soc. JAPAN, 109, 464 (1989)) and 2-aminoindan (330 mg, 2.5 mmol) in dry ethanol (1 ml) were heated to reflux under an argon atmosphere for 40 minutes. The solvent was distilled off under reduced pressure and the residue obtained was purified by silica gel chromatography (hexane:ethyl acetate=5:1) to obtain the title compound (140 mg, 0.50 mmol) having the following physical properties:

$^1$H NMR (400 MHz, CDCl$_3$): δ 2.47 (3H, s), 2.94 (2H, n), 3.50 (2H, m), 5.11 (1H, m), 5.65 (1H, br.), 6.80 (1H, s), 7.19–7.27 (4H, m), 8.47 (1H, s). MS (FAB): m/z 282 (M+H)$^+$.

Production Example 191

4-(2-Indanylamino)thieno[3,4-d]pyrimidine 4-methylthiothieno[3,4-d]pyrimidine (90 mg, 0.50 mmol) (see J. Heterocyclic Chem., 30, 509 (1993)) and 2-aminoindan (200 mg, 1.5 mmol) in dry ethanol (4 ml) were heated to reflux under an argon atmosphere for 4 hours. The solvent was distilled off under reduced pressure and the residue obtained was purified by silica gel chromatography (ethyl acetate:methanol=20:1) to obtain the title compound (30 mg, 0.11 mmol) having the following physical properties:

$^1$H NMR (400 MHz, DMSO-d$_6$): δ 3.02 (2H, m), 3.38 (2H, m), 4.99 (1H, m), 7.17 (2H, m), 7.27 (2H, m), 7.74 (1H, s), 8.17 (1H, s), 8.44 (1H, d, J=6 Hz), 8.52 (1H, s). MS (FAB): m/z 268 (M+H)$^+$.

Production Example 192

4-(2-Indanylamino)-7-methylthieno[3,2-d]pyrimidine 4-chloro-7-methylthieno[3,2-d]pyrimidine (74 mg, 0.40 mmol) and 2-aminoindan (270 mg, 2.0 mmol) in dry ethanol (3 ml) were heated to reflux under an argon atmosphere for 1 hour. The solvent was distilled off under reduced pressure and the residue obtained was purified by silica gel chromatography (hexane:ethyl acetate=1:1) to obtain the title compound (83 mg, 0.30 mmol) having the following physical properties:

$^1$H NMR (400 MHz, DMSO-d$_6$): δ 2.33 (3H, s), 3.03 (2H, m), 3.33 (2H, m), 4.98 (1H, m), 7.16 (2H, m), 7.24 (2H, m), 7.71 (1H, s), 7.98 (1H, d, J=7 Hz), 8.51 (1H, s). MS (FAB): m/z 282 (M+H)$^+$.

Production Example 193

4-(Z-Indanylamino)pyrrolo[2,3-d]pyrimidine 4-chloropyrrolo[2,3-d]pyrimidine (83 mg, 0.54 mmol) (see J. Chem. Soc., 131 (1960), J. Org. Chem., 26, 3809 (1961)) and 2-aminoindan (220 mg, 1.6 mmol) in dry ethanol (5 ml) were heated to reflux under an argon atmosphere for 1 hour. The solvent was distilled off under reduced pressure and the residue obtained was purified by silica gel chromatography (ethyl acetate) to obtain the title compound (38 mg, 0.20 mmol) having the following physical properties:

$^1$H NMR (400 MHz, DMSO-d$_6$): δ 2.96 (2H, m), 3.32 (2H, m), 4.92 (1H, m), 6.57 (1H, m), 7.05 (1H, m), 7.16 (2H, m), 7.25 (2H, m), 7.51 (1H, d, J=8 Hz), 8.13 (1H, s), 11.4 (1H, br.). MS (FAB): m/z 251 (M+H)$^+$.

Production Example 194

4-(2-Indanylamino)thieno[2,3-d]pyrimidine a) To acetic anhydride (4.7 ml) under ice cooling, formic acid (4.7 ml) was added dropwise, to which 2-aminothiophene-3-carboxylic acid ethyl ester (2.8 g, 16.4 mmol) was added and stirred at room temperature for 2 hours. After the solvent was distilled off under reduced pressure, ether was added, and the precipitate that deposited was filtered off. Ether was distilled off under reduced pressure to obtain 2-formylaminothiophene-3-carboxylic acid ethyl ester (3.0 g, 15.3 mmol).

b) 2-formylaminothiophene-3-carboxylic acid ethyl ester (3.0 g, 15.3 mmol) was dissolved in formamide (12 ml), to which ammonium formate (3.0 g, 48.2 mmol) was added and the mixture was stirred at 150° C. for 6 hours. The reaction mixture was allowed to stand overnight at room temperature and the crystals that formed were filtered to obtain 4-hydroxythieno[2,3-d]pyrimidine (1.7 g, 11.0 mmol) having the following physical properties:

$^1$H NMR (400 MHz, DMSO-d$_6$): δ 7.39 (1H, d, J=5.8 Hz), 7.58 (1H, d, J=5.8 Hz), 8.11 (1H, s), 12.45 (1H, broad). MS (FAB): m/z 153 (M+H)$^+$.

c) 4-hydroxythieno[2,3-d]pyrimidine (300 mg, 2.0 mmol) in phosphorous oxychloride (1.5 ml) was heated to reflux for 1 hour. 4-chlorothieno[2,3-d]pyrimidine obtained by distilling off the solvent under reduced pressure. Without further purification of 4-chlorothieno[2,3-d]pyrimidine the resultant mixture was heated to reflux with 2-aminoindan (1.1 g, 8.0 mmol) in dry ethanol (6 ml) under an argon atmosphere for 2 hours. The residue obtained by distilling off the solvent was purified by silica gel chromatography (hexane:ethyl acetate=5:2) to obtain the title compound (150 mg, 0.56 mmol) having the following physical properties:

$^1$H NMR (400 MHz, CDCl$_3$): δ 2.98 (2H, m), 3.50 (2H, m), 5.15 (1H, m), 5.33 (1H, br.), 7.08 (1H, d, J=6 Hz), 7.21–7.29 (5H, m), 8.54 (1H, s). MS (FAB): m/z 268 (M+H)$^+$.

Production Example 195

4-(2-Indanylamino)furo[2,3-d]pyrimidine a) Malononitrile (0.50 g, 7.6 mmol), glycol aldehyde (0.32 g, 2.7 mmol), and triethylamine (0.40 ml, 2.9 mmol) were suspended in toluene (8.7 ml) and the mixture was heated to reflux for 10 minutes. The reaction mixture was washed with brine, dried over anhydrous magnesium sulfate, and then the solvent was distilled off under reduced pressure to obtain 2-amino-3-cyanofuran (0.27 g, 2.5 mmol).

b) A mixture of 2-amino-3-cyanofuran (270 mg, 2.5 mmol), triethyl orthoformate (1.5 ml, 9.0 mmol), and acetic anhydride (0.18 ml, 1.9 mmol) was heated to reflux at 130° C. for 2 hours. The reaction mixture was cooled, and 2-aminoindan (670 mg, 5.0 mmol), sodium acetate (640 mg, 7.8 mmol), and acetic acid (1.1 ml, 19 mmol) were added, which was further heated to reflux at 130° C. for 2 hours. The residue obtained by distilling off the solvent under reduced pressure was purified by silica gel chromatography (hexane:ethyl acetate=2:1) to obtain the title compound (44 mg, 0.18 mmol) having the following physical properties:

$^1$H NMR (400 MHz, CDCl$_3$): δ 2.98 (2H, m), 3.47 (2H, m), 5.05 (1H, m), 5.37 (1H, br.), 6.63 (2H, s), 7.20–7.30 (4H, m), 7.47 (1H, s), 8.44 (1H, s). MS (FAB): m/z 252 (M+H)$^+$. IR (KBr): ν 3490, 3250, 1620, 1590, 1510, 1480, 1140 cm$^{-1}$.

Production Example 196

4-(2-Indanylamino)pyrazolo[3,4-d]pyrimidine

Using 4-hydroxypyrazolo[3,4-d]pyrimidine (140 mg, 1.0 mmol), phosphorus oxychloride (3.0 ml), and dimethylaniline (0.39 ml, 3.1 mmol), and then 2-aminoindan (400 mg, 3.0 mmol), a similar procedure to Production Example 194 was carried out. The product obtained was purified by silica gel chromatography (hexane:ethyl acetate=5:2) to obtain the title compound (150 mg, 0.56 mmol) having the following physical properties:

$^1$H NMR (400 MHz, DMSO-d$_6$): δ 2.95 (2H, m), 3.34 (2H, m), 4.94 (1H, m), 7.17 (2H, m), 7.27 (2H, m), 8.12 (1H, s), 8.26 (1H, s), 8.33 (1H, br.). MS (FAB): m/z 252 (M+H)$^+$.

Production Example 197

7-(2-Indanylamino)-v-triazolo[4.5-d]pyrimidine 4,5-diamino-6-chloropyrimidine (140 mg, 0.97 mmol) (see J. Am. Chem. Soc., 76, 6073 (1954)) and isoamyl nitrite (0.15 ml, 1.1 mmol) in dry dioxane (7 ml) were heated to reflux for 1.5 hours. The reaction mixture was cooled and 2-aminoindan (280 mg, 2.1 mmol) was added thereto, and the mixture was further heated to reflux for 1 hour. The reaction mixture was allowed to stand overnight at room temperature and the precipitate that deposited was filtered off. The residue obtained after concentrating the filtrate under reduced pressure was purified by silica gel chromatography (methylene chloride:methanol=20:1). The product obtained was crystallized from ethanol to obtain the title compound (100 mg, 0.40 mmol) having the following physical properties:

mp: 229–231° C.;

$^1$H NMR (400 MHz, DMSO-d$_6$): δ 3.09 (2H, m), 3.25 (2H, m), 5.02 (1H, m), 7.17 (2H, m), 7.24 (2H, m), 8.39 (1H, s), 9.07 (1H, br.), 15.94 (1H, br.). MS (FAB): m/z 253 (M+H)$^+$.

Production Example 198

7-(2-Indanylamino)oxazolo[5,4-d]pyrimidine 4-cyano-5-ethoxymethyleneaminooxazole (240 mg, 1.5 mmol) (see, J. Am. Chem. Soc., 88, 3829 (1966), Bull. Chem. Soc. JAPAN, 43, 187 (1970), Bull. Chem. Soc.

JAPAN, 43, 3909 (1970)) and 2-aminoindan (580 mg, 4.4 mmol) in dry ethanol (2 ml) were heated to reflux for 6.5 hours. The residue obtained by distilling off the solvent under reduced pressure was purified by silica gel chromatography (methylene chloride:ethyl acetate=1:4) to obtain the title compound (56 mg, 0.22 mmol) having the following physical properties:

$^1$H NMR (400 MHz, DMSO-d$_6$): δ 3.12 (2H, m), 3.30 (2H, m), 4.97 (1H, br.), 7.16 (2H, m), 7.23 (2H, m), 8.37 (1H, br.), 8.51 (1H, br.), 8.62 (1H, s). MS (FAB): m/z 253 (M+H)$^+$.

Production Example 199

3-Methyl-4-(2-indanylamino)isoxazolo[5,4-d]pyrimidine 4-cyano-5-ethoxymethyleneamino-3-aminoisoxazole (320 mg, 1.8 mmol) (see J. Org. Chem., 29, 2116 (1964)) and 2-aminoindan (710 mg, 5.3 mmol) in dry ethanol (3 ml) were heated to reflux for 1.5 hours. The residue obtained by distilling off the solvent under reduced pressure was purified by silica gel chromatography (hexane:ethyl acetate=2:1). The product obtained was crystallized from ethanol to obtain the title compound (270 mg, 0.38 mmol) having the following physical properties:

mp; 208° C.; $^1$H NMR (400 MHz, DMSO-d$_6$): δ 2.62 (3H, s), 3.11 (2H, m), 3.35 (2H, m), 5.12 (1H, m), 7.17 (2H, m), 7.24 (2H, m), 7.60 (1H, br.), 8.46 (1H, s). MS (FAB): m/z 267 (M+N)$^+$. IR (KBr): ν 3260, 1590, 1500, 1460, 1320, 1250, 1220 cm$^+$.

Production Example 200

7-(2-Indanylaminolthiazolo[4-d]pyrimidine

Using 7-chlorothiazolo[5,4-d]pyrimidine (50 mg, 0.29 mmol) (see J. Org. Chem., 26, 4961 (1961), Chem. Pharm. Bull., 16, 750 (1968)) and 2-aminoindan (120 mg, 0.90 mmol), a similar procedure to Production Example 190 was carried out. The product obtained was purified by silica gel chromatography (hexane:ethyl acetate=2:1) to obtain the title compound (41 mg, 0.15 mmol) having the following physical properties:

$^1$H NMR (400 MHz, CDCl$_3$): δ 3.01 (2H, m), 3.50 (2H, m), 5.14 (1H, br.), 6.33 (1H, br.), 7.19–7.28 (4H, m), 8.56 (1H, s), 8.74 (1H, s), 8.49 (1H, s). MS (FAB): m/z 269 (M+H)$^+$.

Production Example 201

2-(2-Indanylamino)-1-thia-2,3,5,7-tetraazaindene

Using 2-chloro-1-thia-2,3,5,7-tetraazaindene (50 mg, 0.29 mmol) (see J. Org. Chem. 26, 4961 (1961), J. Chem. Soc. (C) 1856 (1967)) and 2-aminoindan (120 mg, 0.90 mmol), a similar procedure to Production Example 190 was carried out. The product obtained was purified by silica gel chromatography (hexane:ethyl acetate=3:1) to obtain the title compound (41 mg, 0.15 mmol) having the following physical properties:

$^1$H NMR (400 MHz, CDCl$_3$): δ 3.08 (2H, m), 3.53 (2H, m), 5.25 (1H, br.), 6.99 (1H, br.), 7.22–7.30 (4H, m), 8.66 (1H, s). MS (FAB): m/z 270 (M+H)$^+$.

Production Example 202

6-(2-Indanylamino)-7-methylisothiazolo[3,4-d]pyrimidine

A mixture of 3-amino-5-methyl-4-isothiazole carbonitrile (270 mg, 1.9 mmol) (see Arch. Pharm. Ber. Dtsch. Pharm. Ges., 301, 611 (1968), Angew. Chem. internat. Edit., 6, 83 (1967)), triethyl orthoformate (1.9 ml, 12 mmol), and acetic anhydride (1.9 ml, 20 mmol) was heated to reflux at 130° C. for 2 hours. After the reaction mixture was concentrated under reduced pressure, dry ethanol (3 ml) and 2-aminoindan (780 mg, 5.8 mmol) were added, and was further heated to reflux for 1 hour. The residue obtained by distilling off the solvent under reduced pressure was purified by silica gel chromatography (methylene chloride:ethyl acetate=1:3) to obtain the title compound (100 mg, 0.35 mmol) having the following physical properties:

$^1$H NMR (400 MHz, DMSO-d$_6$): δ 3.04 (3H,s), 3.14 (2H, m), 3.39 (2H, m), 5.12 (1H, m), 7.18 (2H, m), 7.25 (2H, m), 7.32 (1H, br.), 8.35 (1H, s). MS (FAB): m/z 283 (M+H)$^+$.

Production Example 203

7-(2-Indanylamino-1,3-dimethyl-1H-pyrazolo[4,3-d]pyrimidine 7-chloro-1,3-dimethyl-1H-pyrazolo[4,3-d]pyrimidine (28 mg, 0.15 mmol) (see J. Med. Chem. 31, 454 (1988)), 2-aminoindan (66 mg, 0.50 mmol), and triethylamine (30 μl, 0.2 mmol) in dry methylene chloride (1 ml) were heated to reflux for 2 hours. The residue obtained by distilling off the solvent under reduced pressure was purified by silica gel chromatography (hexane:ethyl acetate=1:4) to obtain the title compound (26 mg, 0.093 mmol) having the following physical properties:

$^1$H NMR (400 MHz, DMSO-d$_6$): δ 2.38 (3H, s), 3.09 (2H, m), 3.39 (2H, m), 4.14 (3H, s), 5.06 (1H, s), 7.17 (2H, m), 7.24 (2H, m), 8.26 (1H, s). MS (FAB): m/z 280 (M+H)$^+$.

Production Example 204

4-(2-Indanylamino)pyrido[2,3-d]pyrimidine

Using 4-hydroxypyrido[2,3-d]pyrimidine (150 mg, 1.0 mmol) (see J. Am. Chem. Soc., 77, 2256 (1955)), phosphorus oxychloride (1.0 ml), 2-aminoindan (270 mg, 2.0 mmol), triethylamine (1.4 ml, 10 mmol), and dry dioxane (5 ml), a similar procedure to Product ion Example 203 was carried out. The product obtained was purified by silica gel chromatography (ethyl acetate:methanol=19:1) to obtain the title compound (60 mg, 0.23 mmol) having the following physical properties:

$^1$H NMR (400 MHz, CDCl$_3$): δ 3.06 (2H, m), 3.39 (2H, m), 5.05 (1H, m), 7.17 (2H, m), 7.26 (2H, m), 7.51 (1H, m), 8.60 (1H, br. d), 8.65 (1H, s), 8.80 (1H, m), 8.98 (1H, m). MS (FAB): m/z 293 (M+H)$^+$.

Production Example 205

4-[N-(2-Indanyl)-N-methylamino]-5-methylthieno[2,3-d]pyrimidine

A compound of the above Production Example 190, 4-(2-indanylamino)-5-methylthieno[2,3-d]pyrimidine (29 mg, 0.10 mmol), was dissolved in dry dimethylformamide (0.5 ml), to which sodium hydride (4.4 mg, 0.11 mmol) was added. After the mixture was stirred at room temperature for 10 minutes, methyl iodide (7.0 μl, 0.11 mmol) was added to the reaction mixture, which was further stirred at room temperature for 30 minutes. Water was added to the reaction mixture, which was extracted with chloroform, and the organic layer was dried over anhydrous sodium sulfate. The residue obtained by distilling off the solvent under reduced pressure was purified by silica gel chromatography (hexane:ethyl acetate=2:1) to obtain the title compound (20 mg, 0.070 mmol) having the following physical properties:

$^1$H NMR (400 MHz, CDCl$_3$): δ 2.60 (3H, s), 2.87 (3H, s), 3.13 (2H, m), 3.31 (2H, m), 4.87 (1H, m), 6.98 (1H, s), 7.17 (2H, m), 7.23 (2H, m), 8.59 (1H, s). MS (FAB): m/z 296 (M+H)$^+$.

Production Example 206

4-(2-Indanylamino)-5-phenylthieno[2,3-d] pyrimidine

Using 4-chloro-5-phenylthieno[2,3-d]pyrimidine (50 mg, 0.20 mmol) and 2-aminoindan (110 mg, 0.80 mmol), a similar procedure to Production Example 190 was carried out. The product obtained was purified by silica gel chromatography (hexane:ethyl acetate=2:1) to obtain the title compound (67 mg, 0.20 mmol) having the following physical properties:

$^1$H NMR (400 MHz, CDCl$_3$): δ 2.54 (2H, m), 3.27 (2H, m), 4.92 (1H, m), 5.18 (1H, br.), 7.03 (1H, s), 7.15 (4H, m), 7.21–7.35 (5H, m), 8.53 (1H, s). MS (FAB): m/z 344 (M+H)$^+$.

Production Example 207

4-(2-Indanylamino)-5-(2-thienyl)thieno[2,3-d] pyrimidine

Using 4-chloro-5-(2-thienyl)thieno[2,3-d]pyrimidine (50 mg, 0.20 mmol) and 2-aminoindan (110 mg, 0.80 mmol), a similar procedure to Production Example 190 was carried out. The product obtained was purified by silica gel chromatography (hexane:ethyl acetate=1:1) to obtain the title compound (70 mg, 0.20 mmol) having the following physical properties:

$^1$H NMR (400 MHz, CDCl$_3$): δ 2.66 (2Hz m), 3.34 (2H, m), 5.00 (1H, m), 5.77 (1H, br.), 6.85 (1H, m), 6.89 (1H, m), 7.18 (4H, m), 7.22 (1H, s), 7.29 (1H, m), 8.55 (1H, s). MS (FAB): m/z 350 (M+H)$^+$.

Production Example 208

5-(2-Furyl)-4-(2-indanylamino)thieno[2,3-d] pyrimidine a) Ethyl 2-amino-4-(2-furyl)thiophene-3-carboxylate (500 mg, 2.1 mmol) in formamide (4 ml) was stirred at 180° C. for 3 hours. The precipitate obtained by cooling the reaction mixture was filtered to obtain 5-(2-furyl)-4-hydroxythieno[2,3-d]pyrimidine (330 mg, 1.5 mmol) having the following physical properties:

$^1$H NMR (400 MHz, DMSO-d$_6$): δ 6.56 (1l, m), 7.56 (1H, d, J=3 Hz), 7.72 (2H, m), 8.14 (1H, s), 12.52 (1H, br. d).

b) 5-(2-furyl)-4-hydroxythieno[2,3-d]pyrimidine (180 mg, 0.80 mmol) in phosphorus oxychloride (2.0 ml) was heated to reflux for 2 hours. 5-(2-furyl)-4-chlorothieno[2,3-d]pyrimidine obtained by distilling off the solvent under reduced pressure, without further purification, together with 2-aminoindan (130 mg, 0.98 mmol) and triethylamine (0.90 ml, 6.4 mmol) in dry ethanol (5 ml) was heated to reflux under an argon atmosphere for 2 hours. The residue obtained by distilling off the solvent was purified by silica gel chromatography (hexane:ethyl acetate=2:1) to obtain the title compound (130 mg, 0.39 mmol) having the following physical properties:

$^1$H NMR (400 MHz, CDCl$_3$): δ 2.86 (2H, m), 3.43 (2H, m), 5.14 (1H, m), 6.40 (1H, m), 6.44 (1H, m), 6.79 (1H, br.), 7.09 (1H, m), 7.20–7.30 (4H, m), 8.53 (1H, m). MS (FAB): m/z 334 (M+H)$^+$.

Production Example 209

4-(2-Indanylamino)-5,6-dimethylthieno[2,3-d] pyrimidine a) Using ethyl 2-amino-4,5-dimethylthiophene-3-carboxylate (500 mg, 2.5 mmol) and formamide (5 ml), a similar procedure to a) in Production Example 208 was carried out to obtain 4-hydroxy-5,6-dimethylthieno[2,3-d]pyrimidine (380 mg, 2.1 mmol) having the following physical properties:

$^1$H NMR (400 MHz, DMSO-d$_6$): δ 2.35 (3H, s), 2.39 (3H, s), 7.98 (1H, s), 12.17 (1H, br. s).

b) Using 4-hydroxy-5,6-dimethylthieno[2,3-d]pyrimidine (180 mg, 1.0 mmol), phosphorus oxychloride (1.0 ml), 2-aminoindan (270 mg, 2.0 mmol), triethylamine (0.84 ml, 6.0 mmol) and dry ethanol (5 ml), a similar procedure to b) in Production Example 208 was carried out. The product obtained was purified by silica gel chromatography (hexane:ethyl acetate=2:1) to obtain the title compound (190 mg, 0.64 mmol) having the following physical properties:

$^1$H NMR (400 MHz, CDCl$_3$): δ 2.32 (3H, s), 2.38 (3H, s), 2.93 (2H, m), 3.50 (2H, m), 5.09 (1H, m), 5.62 (1H, br. d), 7.20 (2H, m), 7.26 (2H, m), 8.42 (1H, s). MS (FAB): m/z 296 (M+H)$^+$.

Production Example 210

4-(2-Indanylamino)-5-[6-(3-methylpyridyl)]thieno[2, 3-d]pyrimidine a) Using ethyl 2-amino-5-(6-(3-methylpyridyl)] thiophene-3-carboxylate (520 mg, 2.0 mmol) and formamide (4 ml), a similar procedure to a) in Production Example 208 was carried out to obtain 4-hydroxy-5-[6-(3-methylpyridyl)]thieno[2,3-d]pyrimidine (330 mg, 1.4 mmol) having the following physical properties:

$^1$H NMR (400 MHz, DMSO-d$_6$): δ 7.27(1H, d, J=8 Hz), 7.61 (1H, s), 7.82 (1H, d, J=8 Hz), 8.15 (1H, a), 8.59 (1H, s), 12.48 (1H, br. s).

b) Using 4-hydroxy-5-[6-(3-methylpyridyl)]thieno[2,3-d]pyrimidine (240 mg, 1.0 mmol), phosphorus oxychloride (3.0 ml), 2-aminoindan (270 mg, 2.0 mmol), triethylamine (2.8 ml, 20 mmol) and dry ethanol (6 ml), a similar procedure to b) in Production Example 208 was carried out. The product obtained was purified by silica gel chromatography (methylene chloride ethyl acetate=1:1) to obtain the title compound (140 mg, 0.38 mmol) having the following physical properties:

$^1$H NMR (400 MHz, CDCl$_3$): δ 2.57 (3H, s), 2.60 (2H, m), 3.29 (2H, m), 4.97 (2H, m), 6.85 (1H, d, J=8 Hz), 7.06 (1H, s), 7.15–7.20 (4H, m), 7.35 (1H, m), 8.52 (1H, m), 8.54 (1H, s). MS (FAB): m/z 359 (M+H)$^+$.

Production Example 211

4-(2-Indanylamino)-5-isopropylthieno[2,3-d] pyrimidine a) Using ethyl 2-amino-4-isopropylthiophene-3-carboxylate (800 mg, 3.8 mmol) and formamide (5 ml), a similar procedure to a) in Production Example 208 was carried out to obtain 4-hydroxy-5-isopropylthieno[2,3-d]pyrimidine (330 mg, 1.7 mmol) having the following physical properties:

$^1$H NMR (400 MHz, DMSO-d$_6$): δ 1.33 (6H, d, J=7 Hz), 3.75 (1H, m), 6.95 (1H, s), 8.00 (1H, s), 11.43 (1H, br.

b) Using 4-hydroxy-5-isopropylthieno[2,3-d]pyrimidine (200 mg, 1.03 mmol), phosphorus oxychloride (1.0 ml), 2-aminoindan hydrochloride (200 mg, 1.2 mmol), triethylamine (1.0 ml, 7.2 mmol) and dry ethanol (5 ml), a similar procedure to b) in Production Example 208 was carried out. The product obtained was purified by silica gel chromatography (hexane:ethyl acetate=2:1) to obtain the title compound (190 mg, 0.64 mmol) having the following physical properties:

$^1$H NMR (400 MHz, CDCl$_3$): δ 1.25 (6H, d, J=7 Hz), 2.96 (3H, m), 3.50 (2H, dd, J=7 Hz, 16 Hz), 5.16 (1H, m), 5.63 (1H, br. d), 6.87 (1H, s), 7.20 (2H, m), 7.26 (2H, m), 8.49 (1H, s). MS (FAB): m/z 310 (M+H)$^+$.

Production Example 212

4-(5-Methoxyindan-2-yl]amino-5-methylthieno[2,3d]pyrimidine

Using 2-amino-5-methoxyindan (90 mg) synthesized in b) in the above Reference Production Example 1,4-chloro 5-methylthieno[2,3-d]pyrimidine (90 mg, 0.50 mmol), triethylamine (0.23 ml, 1.7 mmol) and ethanol (1 ml), a similar procedure to b) in Production Example 20 was carried out. The product obtained was purified by silica gel chromatography (hexane:ethyl acetate=4:1) to obtain the title compound (20 mg, 0.064 mmol) having the following physical properties:

$^1$H NMR (400 MHz, CDCl$_3$): δ 2.47 (3H, s), 2.88 (2H, m), 3.45 (2H, m), 3.80 (3H, s), 5.10 (1H, m), 5.13 (1H, br. d), 6.76 (1H, m), 6.80 (2H, m), 8.47 (1H, s). MS (FAB): m/z 312 (M+H)$^+$.

Production Example 213

4-(5-Hydroxyindan-2-yl]amino-5-methylthieno[2,3-d]pyrimidine

To 2-(tert-butoxycarbonylamino)-5-hydroxyindan (130 mg, 0.50 mmol) synthesized in the above Reference Production Example 1 was added 4N hydrochloric acid-dioxane (2.3 ml) and acetic acid (6.9 ml), and the mixture was stirred at room temperature for 10 minutes. By distilling off the solvent under reduced pressure, 2-amino-5-hydroxyindan hydrochloride was obtained as a crude product. This was dissolved in ethanol (3 ml). Using triethylamine (0.14 ml, 1.0 mmol), 4-chloro-5-methylthieno[2,3-d]pyrimidine (83 mg, 0.60 mmol), a similar procedure to b) in Production Example 208 was carried out. The product obtained was purified by silica gel chromatography (methylene chloride:ethyl acetate=2:1) to obtain the title compound (17 mg, 0.057 mmol) having the following physical properties:

$^1$H NMR (400 MHz, DMSO-d$_6$): δ 2.56 (3H, s), 2.94 (2H, m), 3.22 (2H, m), 4.97 (1H, m), 6.55 (2H, m), 6.63 (1H, s), 7.00 (1H, d, J=8 Hz), 7.14 (1H, s), 8.35 (1H, s), 9.06 (1H, s). MS (FAB): m/z 298 (M+H)$^+$. IR (KBr): ν 3470, 1580, 1500 cm$^{-1}$.

Production Example 214

4-(5-Phenoxyindan-2-yl)amino-5-methylthieno[2,3-d]pyrimidine a) 2-(tert-butoxycarbonylamino)-5-hydroxyindan (100 mg, 0.40 mmol) synthesized in the above Reference Production Example 1 was dissolved in acetone (2 ml), to which potassium carbonate (58 mg, 0.45 mmol) and benzylbromide (48 μl, 0.40 mmol) were added, and the mixture was heated to reflux for 3 hours. The reaction mixture was extracted with ether and dried, and then the solvent was distilled off under reduced pressure to obtain 2-(tert-butoxycarbonylamino)-5-phenoxyindan (120 mg, 0.36 mmol) having the following physical properties:

$^1$H NMR (400 MHz, CDCl$_3$): δ 1.44 (9H, s), 2.72 (2H, m), 3.22 (2H, m), 4.48 (1H, m), 4.74 (1H, m), 5.04 (2H, s), 6.79 (1H, m), 6.84 (1H, m), 7.09 (1H, m), 7.29–7.43 (5H, m). MS (FAB): m/z 340 (M+H)$^+$.

b) Using 2-(tert-butoxycarbonylamino)-5-phenoxyindan (120 mg, 0.36 mmol), 4N hydrochloric acid-dioxane (1.7 ml) and acetic acid (5.1 ml), a similar procedure to Production Example 213 was carried out to obtain 2-amino-5-phenoxyindan hydrochloride (99 mg, 0.36 mmol) having the following physical properties:

$^1$H NMR (400 MHz, DMSO-d$_6$): δ 2.88 (2H, m), 3.21 (2H, m), 3.98 (1H, m), 5.08 (1H, m), 6.84 (1H, m), 6.63 (1H, s), 6.95 (1H, m), 7.16 (1H, m), 7.32–7.43 (5H, m), 8.09 (2H, br.). MS (FAB): m/z 240 (M+H)$^+$.

c) Using 2-amino-5-phenoxyindan hydrochloride (99 mg, 0.36 mmol), ethanol (3 ml), triethylamine (92 μl, 0.66 mmol), and 4-chloro-5-methylthieno[2,3-d]pyrimidine (61 mg, 0.33 mmol), a similar procedure to b) in Production Example 208 was carried out. The product obtained was purified by silica gel chromatography (hexane:ethyl acetate=1:1) to obtain the title compound (51 mg, 0.13 mmol) having the following physical properties:

$^1$H NMR (400 MHz, CDCl$_3$): δ 2.47 (3H, s), 2.87 (2H, m), 3.45 (2H, m), 5.05 (2H, 9), 5.11 (1H, m), 5.63 (1H, br. d), 6.82 (2H, m), 6.89 (1H, s), 7.15 (1H, d, J=8 Hz), 7.32–7.44 (5H, m), 8.47 (1H, s). MS (FAB): m/z 388 (M+H)$^+$. IR (KBr): ν 3460, 1570, 1500, 1450, 1240, 1010 cm$^{-1}$.

Production Example 215

4-[5-[(E)-2-(4-Methylphenyl)ethenyl]indan-2-yl]amino-5-methylthieno[2,3-d]pyrimidine a) Using 2-(tert-butoxycarbonylamino)-5-((E)-2-(4-methylphenyl)ethenyl]indan (20 mg, 0.060 mmol) synthesized in Reference Production Example 2, 4N hydrochloric acid-dioxane (2.0 ml) and acetic acid (6.0 ml), a similar procedure to Production Example 213 was carried out to obtain 2-amino-5-((E)-2-(4-methylphenyl)ethenyl]indan hydrochloride (16 mg, 0.06 mmol) having the following physical properties:

$^1$H NMR (400 MHz, MeOH-d$_6$): δ 2.33 (3H, s), 3.02 (2H, n), 3.40 (2H, m), 4.10 (1H, m), 7.10–7.17 (4H, m), 7.27 (1H, m), 7.42 (3H, m), 7.49 (1H, m).

b) Using 2-amino-5-[(E)-2-(4-methylphenyl)ethenyl]indan hydrochloride (16 mg, 0.06 mmol), ethanol (0.6 ml), triethylamine (50 μl, 0.36 mmol), and 4-chloro-5-methylthieno[2,3-d]pyrimidine (11 mg, 0.060 mmol), a similar procedure to b) in Production Example 208 was carried out The product obtained was purified by silica gel chromatography (hexane:ethyl acetate=4:1) to obtain the title compound (14 mg, 0.035 mmol) having the following physical properties:

$^1$H NMR (400 MHz, CDCl$_3$): δ 2.36 (3H, s), 2.47 (3H, s), 2.93 (2H, m), 3.51 (2H, m), 5.13 (1H, m), 5.63 (1H, br. d), 6.80 (1H, s), 7.06 (2H, s), 7.16 (2H, m), 7.23 (1H, m), 7.34 (1H, m), 7.41 (3H, m), 8.48 (1H, s). MS (FAB): m/z 398 (M+H)$^+$. IR (KBr): ν 1570, 1500 cm$^{-1}$.

Production Example 216

4-(5-Methoxycarbonylindan-2-yl)amino-5-methylthieno[2,3-d]pyrimidine

Using 2-(tert-butoxycarbonylamino)-5-methoxycarbonylindan (60 mg, 0.21 mmol) synthesized in the above Reference Production Example 3, 4N hydrochloric acid-dioxane (1.0 ml) and acetic acid (3.0 ml), and then ethanol (1 ml), triethylamine (88 μl, 0.63 mmol), and 4-chloro-5-methylthieno[2,3-d]pyrimidine (39 mg, 0.21 mmol), a similar procedure to Production Example 213 was carried out. The product obtained was purified by silica gel chromatography (methylene chloride:ethyl acetate=6:1) to obtain the title compound (32 mg, 0.094 mmol) having the following physical properties:

$^1$H NMR (400 MHz, CDCl$_3$): δ 2.47 (3H, s), 2.98 (2H, m), 3.54 (2H, m), 3.91 (3H, s), 5.15 (1H, m), 5.60 (1H, br. d), 6.82 (1H, s), 7.32 (2H, m), 7.91 (1H, m), 7.94 (1H, m), 8.48 (1H, s). MS (FAB): m/z 340 (M+H)$^+$. IR (KBr): ν 1720, 1570, 1500, 1270 cm$^{-1}$.

Production Example 217

4-(5-Carboxyindan-2-yl)amino-5-methylthieno[2,3-d]pyrimidine Sodium Salt 4-(5-methoxycarbonylindan-2-yl)amino-5-methylthieno[2,3-d]pyrimidine (27 mg, 0.08 mmol) synthesized in the above Production Example 216, methanol (1 ml), and an aqueous solution of 1N sodium hydroxide (88 μl) were heated to reflux for 7 hours. To the residue obtained by distilling off the solvent under reduced pressure, ethyl acetate was added, and the precipitate that formed was filtered to obtain the title compound (25 mg, 0.072 mmol) having the following physical properties:

$^1$H NMR (400 MHz, DMSO-d$_6$): δ 2.57 (3H, s), 3.03 (2H, m), 3.34 (2H, m), 5.01 (1H, m), 6.58 (1H, br. d), 7.08 (1H, m), 7.15 (1H, s), 7.68 (1H, m), 7.71 (1H, m), 8.37 (1H, s). MS (FAB): m/z 326 (M+H)$^+$, 348 (M+Na)$^+$. IR (KBr): ν 3450, 1570, 1550, 1500, 1430, 1400 cm$^{-1}$.

Production Example 218

N-Propyl-2-(5-methylthieno[2,3-d]pyrimidine-4-yl) amino-5-indan Carboxamide a) 2-(tert-butoxycarbonylamino)-5-carboxyindan (30 mg, 0.11 mmol) synthesized in Reference Production Example 4, n-propylamine (20 μl, 0.24 mmol), triethylamine (0.20 ml, 1.4 mmol), propanephosphonic acid anhydride (0.3 ml) (see Japanese Unexamined Patent Publication (Kokai) No. 55-100346), and dimethylaminopyridine (acatalytic amount) in methylene chloride (0.25 ml) were stirred at room temperature for 30 minutes. The reaction mixture was diluted with ethyl acetate, and then washed with, in the order of, an aqueous solution of saturated potassium hydrogen sulfate, brine, an aqueous solution of saturated sodium hydrogen carbonate, and brine, and then was dried over anhydrous sodium sulfate. The residue obtained by distilling off the solvent under reduced pressure was purified by silica gel chromatography (hexane:ethyl acetate=4:1 to 3:7) to obtain N-propyl-2-(tert-butoxycarbonylamino)-5-indan carboxamide (22 mg, 0.070 mmol) having the following physical properties:

$^1$H NMR (400 MHz, CDCl$_3$): δ 0.99 (3H, t, J=8 Hz), 1.45 (9H, s), 1.65 (2H, q, J=7 Hz), 2.81 (2H, dd, J=5 Hz, 16 Hz), 3.31 (2H, dd, J=7 Hz, 16 Hz), 3.41 (2H, q, J=6 Hz), 4.50 (1H, br. s), 4.70 (1H, br. s), 6.07 (1H, br. s), 7.24 (1H, d, J=8 Hz), 7.55 (1H, d, J=8 Hz), 7.62 (1H, s). MS (FAB): m/z 319 (M+H)$^+$. IR (KBr): ν 1690, 1640, 1540, 1170 cm$^{-1}$.

b) Using N-propyl-2-(tert-butoxycarbonylamino)-5-indan carboxamide (22 mg, 0.070 mmol), 4N hydrochloric acid-dioxane (2 ml) and acetic acid (6.0 ml), a similar procedure to Production Example 213 was carried out to obtain N-propyl-2-amino-5-indan carboxamide hydrochloride. Then using ethanol (1 ml), triethylamine (0.50 ml, 3.6 mmol), and 4-chloro-5-methylthieno[2,3-d]pyrimidine (18 mg, 1.0 mmol), a similar procedure to b) in Production Example 208 was carried out. The product obtained was purified by silica gel chromatography (hexane:ethyl acetate= 2:1 to 1:2) to obtain the title compound (12 mg, 0.033 mmol) having the following physical properties:

$^1$H NMR (400 MHz, CDCl$_3$): δ 0.99 (3H, t, J=7 Hz), 1.70 (2H, m), 2.46 (3H, d, J=1 Hz), 2.97 (2H, dd, J=5 Hz, 16 Hz), 3.42 (2H, q, J=6 Hz), 3.52 (2H, dd, J=7 Hz, 16 Hz), 5.12 (1H, m), 5.60 (1H, br. d), 6.10 (1H, br. s), 6.84 (1H, s), 7.29 (1H, d, J=8 Hz), 7.58 (1H, d, J=8 Hz), 7.68 (1H, s), 8.47 (1H, s). MS (FAB): m/z 3167 (M+H)$^+$. IR (KBr): ν 1650, 1570, 1490 cm$^{-1}$.

Production Example 219

N-Phenyl-2-(5-methylthieno[2,3-d]pyrimidine-4-yl) amino-5-indan Carboxamide a) Using 2-(tert-butoxycarbonylamino)-5-carboxyindan (30 mg, 0.11 mmol) synthesized in Reference Production Example 4, aniline (21 μl, 0.23 mmol), triethylamine (0.20 ml, 1.4 mmol), propanephosphonicacid anhydride (0.3 ml), dimethylaminopyridine (a catalytic amount) and methylene chloride (0.25 ml), a similar procedure to a) in Production Example 21 was carried out. The product obtained was purified by silica gel chromatography (hexane:ethyl acetate= 4:1 to 7:3) to obtain N-phenyl-2-(tert-butoxycarbonylamino)-5-indan carboxamide (27 mg, 0.077 mmol) having the following physical properties:

$^1$H NMR (400 MHz, CDCl$_3$): δ 1.46 (9H, s), 2.85 (2H, dd, J=5 Hz, 16 Hz), 3.31 (2H, dd, J=7 Hz, 16 Hz), 4.40 (1H, m), 4.50 (1H, br. s), 4.75 (1H, br. s), 7.14 (1H, t, J=7 Hz), 7.35 (2H, d, J=8 Hz), 7.63 (2H, d, J=8 Hz), 7.66 (1H, d, J=8 Hz), 7.72 (1H, s), 7.81 (1H, s). MS (FAB): m/z 353 (M+H)$^+$. IR (KBr): ν 1680, 1540, 1170 cm$^{-1}$.

b) Using N-phenyl-2-(tert-butoxycarbonylamino)-5-indan carboxamide (27 mg, 0.077 mmol), 4N hydrochloric acid-dioxane (2.0 ml) and acetic acid (6.0 ml), a similar procedure to Production Example 213 was carried out to obtain N-phenyl-2-amino-5-indan carboxamide hydrochloride. Then using ethanol (1 ml), triethylamine (0.50 ml, 3.6 mmol), 4-chloro-5-methylthieno[2,3-d]pyrimidine (18 mg, 1.0 mmol), a similar procedure to b) in Production Example 208 was carried out. The product obtained was purified by silica gel chromatography (hexane:ethyl acetate=4:1 to 1:1) to obtain the title compound (8 mg, 0.020 mmol) having the following physical properties:

$^1$H NMR (400 MHz, CDCl$_3$—MeOH-d$_6$): δ 2.50 (3H, s), 3.03 (2H, br. d, J=6 Hz), 3.57 (2H, dd, J=7 Hz, 16 Hz), 5.10 (1H, br. s), 6.87 (1H, s), 7.15 (1H, t, J=7 Hz), 7.66 (2H, d, J=8 Hz), 7.75 (1H, d, J=8 Hz), 7.82 (1H, s), 8.43 (1H, s). MS (FAB): m/z 401 (M+H)$^+$. IR (KBr): ν 1640, 1560, 1500, 1370 cm$^{-1}$.

Production Example 220

N-Benzyl-2-(5-methylthieno[2,3-d]pyrimidine-4-yl) amino-5-indan Carboxamide a) Using 2-(tert-butoxycarbonylamino)-5-carboxyindan (400 mg, 1.44 mmol), benzylamine (0.24 ml, 2.2 mmol), triethylamine (1.4 ml, 10 mmol), propanephosphonic acid anhydride (2.1 ml), dimethylaminopyridine (a catalytic amount) and methylene chloride (12 ml), a similar procedure to a) in Production Example 218 was carried out. The product obtained was purified by silica gel chromatography (methylene chloride:methanol=95:5) to obtain N-benzyl-2-(tert-butoxycarbonylamino)-5-indan carboxamide (460 mg, 1.25 mmol) having the following physical properties:

$^1$H NMR (400 MHz, CDCl$_3$): δ 1.44 (9H, s), 2.80 (2H, dd, J=4 Hz, 16 Hz), 3.27 (2H, dd, J=3 Hz, 12 Hz), 4.50 (1H, br. s), 4.64 (2H, d, J=5 Hz), 4.70 (1H, br. s), 6.34 (1H, br. s), 7.30 (6H, m), 7.59 (1H, d, J=8 Hz), 7.65 (1H, s). IR (KBr): ν 3300, 1690, 1640, 1540, 1280, 1170 cm$^{-1}$.

b) Using N-benzyl-2-(tert-butoxycarbonylamino)-5-indan carboxamide (820 mg, 2.2 mmol), 4N hydrochloric acid-dioxane (10 ml) and acetic acid (30 ml), a similar procedure to Production Example 213 was carried out to obtain N-benzyl-2-amino-5-indan carboxamide hydrochloride (660 mg, 2.2 mmol) having the following physical properties:

$^1$H NMR (400 MHz, DMSO-d$_6$): δ 3.01 (2H, dd, J=5 Hz, 17 Hz), 3.32 (2H, dd, J=8 Hz, 17 Hz), 4.03 (1H, m), 4.48 (2H, d, J=6 Hz), 7.23–7.32 (5H, m), 7.36 (1H, d, J=8 Hz), 7.76 (1H, d, J=8 Hz), 7.81 (1H, s), 8.17 (3H, br.), 8.96 (1H, m).

c) Using N-benzyl-2-amino-5-indan carboxamide hydrochloride (660 mg, 2.2 mmol), ethanol (19 ml), triethylamine (0.94 ml, 6.7 mmol), and 4-chloro-5-methylthieno[2,3-d]pyrimidine (410 mg, 2.2 mmol), a similar procedure to b) in Production Example 208 was carried out. A solid obtained by purifying the product by silica gel chromatography (methylene chloride:ethanol=95:5) was washed with ether to obtain the title compound (580 mg, 1.4 mmol) having the following physical properties:

$^1$H NMR (400 MHz, DMSO-d$_6$): δ 2.57 (3H, s), 3.11 (2H, dd, J=7 Hz, 16 Hz), 3.42 (2H, dd, J=8 Hz, 10 Hz), 4.47 (2H, d, J=6 Hz), 5.05 (1H, m), 6.62 (1H, d, J=7 Hz), 7.15 (1H, s), 7.23 (1H, m), 7.31 (4H, m), 7.72 (1H, d, J=8 Hz), 7.78 (1H, s), 8.37 (1H, s), 8.92 (1H, m). MS (FAB): m/z 415 (M+H)$^+$. IR (KBr): ν 1650, 1570, 1500 cm$^{-1}$.

Production Example 221

2-[5-Methylthieno[2,3-d]pyrimidine-4-yl]aminoindan-5-carboxylic Acid Morpholinamide a) Using 2-(tert-butoxycarbonylamino)-5-carboxyindan (1.01 g, 3.6 mmol), morpholine (0.48 ml, 5.5 mmol), triethylamine (3.6 ml, 26 mmol), propanephosphonic acid anhydride (5.3 ml), dimethylaninopyridine (a catalytic amount) and methylene chloride (27 ml), a similar procedure to a) in Production Example 218 was carried out. The product obtained was purified by silica gel chromatography (methylene chloride:methanol=95:5) to obtain 2-(tert-butoxycarbonylamino)indan-5-carboxylic acid morpholinamide (1.0 g, 2.9 mmol) having the following physical properties:

$^1$H NMR (400 MHz, CDCl$_3$): δ 1.45 (9H, s) 2.79 (2H, dd, J=3 Hz, 16 Hz), 3.27(2H, dd, J=7 Hz, 16 Hz), 3.70 (8H, br. s), 4.40 (1H, br. s), 4.70 (1H, br. s), 7.25 (3H, m). IR (XBr): ν 3320, 2970, 1710, 1620, 1520, 1430, 1270, 1170, 1110 cm$^{-1}$.

b) Using 2-(tert-butoxycarbonylamino)indan-5-carboxylic acid morpholinamide (1.0 g, 2.7 mmol), 4N hydrochloric acid-dioxane (12 ml) and acetic acid (36 ml), a similar procedure to Production Example 213 was carried out to obtain 2-aminoindan-5-carboxylic acid morpholinamide hydrochloride (750 mg, 2.7 mmol) having the following physical properties:

$^1$H NMR (400 MHz, DMSO-d$_6$): δ 2.99 (2H, m), 3.29 (2H, m), 3.59 (8H, br. s), 4.02 (1H, m), 7.24 (1H, d, J=8 Hz), 7.33 (3H, m), 8.20 (3H, br. s).

c) Using 2-aminoindan-5-carboxylic acid morpholinamide hydrochloride (750 mg, 2.7 mmol), ethanol (23 ml), triethylamine (1.1 ml, 8.2 mmol), and 4-chloro-5-methylthieno[2,3-d]pyrimidine (500 mg, 2.7 mmol), a similar procedure to b) in Production Example 208 was carried out. The product obtained was purified by silica gel chromatography (methylene chloride:methanol=95:5) to yield a fraction, which was then washed with ether to obtain the title compound (680 mg, 1.7 mmol) having the following physical properties:

$^1$H NMR (400 MHz, CDCl$_3$):δ 8 2.49 (3H, s), 2.96 (2H, dd, J=5 Hz, 16 Hz), 3.54 (2H, dd, J=7 Hz, 16 Hz), 3.70 (8H, br. s), 5.10 (1H, m), 5.60 (1H, d, J=6 Hz), 7.25 (3H, m), 8.41 (1, s). MS (FAB): m/z 395 (M+H)$^+$. IR (KBr): ν 1570, 1500, 1110 cm$^{-1}$.

Production Example 222

4-(4-Methoxyindan-2-yl)amino-5-methylthieno[2,3-d]pyrimidine

Using 2-amino-4-methoxyindan (27 mg, 0.17 mmol) synthesized in the above b) in Reference Production Example 5, 4-chloro-5-methylthieno[2,3-d]pyrimidine (31 mg, 0.17 mmol), triethylamine (71 μl, 0.51 mmol), and ethanol (1.5 ml), a similar procedure to b) in Production Example 208 was carried out. The product obtained was purified by silica gel chromatography (hexane:ethyl acetate=2:1) to obtain the title compound (50 mg, 0.16 mmol) having the following physical properties:

$^1$H NMR (400 MHz, CDCl$_3$): δ 2.48 (3H, s), 2.91 (2H, m), 3.49 (2H, m), 5.10 (1H, m), 5.63 (1H, br. d), 6.72 (1H, d, J=8 Hz), 6.80 (1H, m), 6.87 (1H, d, J=7 Hz), 7.19 (1H, t, J=8 Hz), 8.47 (1H, s). MS (FAB): m/z 312 (M+H)$^+$. IR (KBr): ν 3470, 1570, 1490, 1260, 1070 cm$^{-1}$.

Production Example 223

4-(4-Methoxycarbonylindan-2-yl)amino-5-methylthieno[2,3-d]pyrimidine

Using 2-(tert-butoxycarbonylamino)-4-methoxycarbonylindan (45 mg, 0.15 mmol) synthesized in the above Reference Production Example 7, 4N hydrochloric acid-dioxane (0.7 ml) and acetic acid (2.1 ml), a similar procedure to Production Example 213 was carried out to obtain 2-amino-4-methoxycarbonylindan hydrochloride. Then, using the 2-amino-4-methoxycarbonylindan hydrochloride, 4-chloro-5-methylthieno[2,3-d]pyrimidine (28 mg, 0.15 mmol), triethylamine (63 μl, 0.45 mmol), and ethanol (1 ml), a similar procedure to b) in Production Example 208 was carried out. The product obtained was purified by silica gel chromatography (hexane:ethyl acetate= 2:1) to obtain the title compound (15 mg, 0.044 mmol) having the following physical properties:

$^1$H NMR (400 MHz, CDCl$_3$): δ 2.49 (3H, s), 2.97 (1H, dd, J=5 Hz, 16 Hz), 3.33 (1H, dd, J=5 Hz, 18 Hz), 3.56 (1H, dd, J=7 Hz, 16 Hz), 3.86 (1H, dd, J=7 Hz, 18 Hz), 3.91 (3H, s), 5.11 (1H, m), 5.61 (1H, br. d), 6.81 (1H, s), 7.28 (1H, m), 7.44 (1H, d, J=8 Hz), 7.89 (1H, d, J=8 Hz), 8.48 (1H, s). MS (FAB): m/z 340 (M+H)$^+$. IR (KBr): ν 3430, 1700, 1570, 1490, 1300 cm$^{-1}$.

Production Example 224

4-(5-Acetoxyindan-2-yl)amino-5-methylthieno[2,3-d]pyrimidine a) 2-(tert-butoxycarbonylamino)-5-hydroxyindan (100 mg, 0.40 mmol) synthesized in Reference Production Example 1 was dissolved in dry methylene chloride (2 ml), to which pyridine (0.19 ml, 2.3 mmol) and acetic anhydride (0.11 ml, 1.2 mmol) were added, and the mixture was stirred at room temperature for 2 hours. The reaction mixture then was concentrated under reduced pressure, to which diethylether was added. The organic layer was washed with, in the order of, an aqueous solution of saturated potassium hydrogen sulfate, brine, an aqueous solution of saturated sodium hydrogen carbonate, and brine, and then was dried over anhydrous sodium sulfate. The solvent was distilled off under reduced pressure to obtain 5-acetoxy-2-(tert-butoxycarbonylamino)indan (120 mg, 0.40 mmol) having the following physical properties:

$^1$H NMR (400 MHz, CDCl$_3$): δ 1.45 (9H, s), 2.28 (3H, s), 2.77 (2H, m), 3.26 (2H, m), 4.47 (1H, m), 4.75 (1H, m), 6.86 (1H, d, J=8 Hz), 6.93 (1H, s), 7.19 (1H, d, J=8 Hz). MS (FAB): m/z 292 (M+H)$^+$, 236 (M+H-56)$^+$.

b) Using 5-acetoxy-2-(tert-butoxycarbonylamino)indan (120 mg, 0.40 mmol), 4N hydrochloric acid-dioxane (2 ml) and acetic acid (6 ml), a similar procedure to Production Example 213 was carried out to obtain 5-acetoxy-2-aminoindan hydrochloride (86 mg, 0.38 mmol) having the following physical properties:

$^1$H NMR (400 MHz, DMSO-d$_6$): δ 2.25 (3H, s), 2.95 (2H, m), 3.27 (2H, m), 4.02 (1H, m), 6.94 (1H, d, J=8 Hz), 7.03 (1H, s), 7.29 (1H, d, J=8 Hz), 8.17 (3H, br. s).

c) Using 5-acetoxy-2-aminoindan hydrochloride (86 mg, 0.38 mmol), 4-chloro-5-methylthieno[2,3-d]pyrimidine (76 mg, 0.41 mmol), triethylamine (0.23 ml, 1.6 mmol), and ethanol (6 ml), a similar procedure to b) in Production Example 208 was carried out. The product obtained was purified by silica gel chromatography (hexane:ethyl acetate= 2:1) to obtain the title compound (34 mg, 0.10 mmol) having the following physical properties:

$^1$H NMR (400 MHz, CDCl$_3$): δ 2.29 (3H, s), 2.49 (3H, s), 2.92 (2H, m), 3.50 (2H, m), 5.13 (1H, m), 5.62 (1H, br. d), 6.81 (1H, s), 6.91 (1H, dd, J=2 Hz, 8 Hz), 6.98 (1H, 8), 7.24 (1H, d, J=8 Hz), 8.47 (1H, s). MS (FAB): m/z 340 (M+H)$^+$.

Production Example 225

4-(5-Benzoyloxyindan-2-yl)amino-5-methylthieno [2,3-d]pyrimidine a) 2-(tert-butoxycarbonylamino)-5-hydroxyindan (100 mg, 0.40 mmol) synthesized in Reference Production Example 1 was dissolved in dry methylene chloride (2 ml), to which pyridine (0.15 ml, 1.8 mmol) and benzoyl chloride (0.14 ml, 1.1 mmol) were added, and the mixture was stirred overnight at room temperature. The reaction mixture was concentrated under reduced pressure, to which diethylether was added. The organic layer was washed with, in the order of, an aqueous solution of saturated potassium hydrogen sulfate, brine, an aqueous solution of saturated sodium hydrogen carbonate, and brine, and then was dried over anhydrous sodium sulfate. The residue obtained by distilling off the solvent under reduced pressure was purified by silica gel chromatography (hexane:ethyl acetate=3:1) to obtain 2-(tert-butoxycarbonylamino)-5-benzoyloxyindan (130 mg, 0.37 mmol) having the following physical properties:

$^1$H NMR (400 MHz, CDCl$_3$): δ 1.45 (9H, s), 2.80 (2H, m), 3.29 (2H, m), 4.50 (1H, m), 4.78 (1H, m), 7.00 (1H, dd, J=2 Hz, 8 Hz), 7.07 (1H, s), 7.25 (1H, d, J=8 Hz), 7.51 (2H, t, J=8 Hz), 7.63 (1H, t, J=7 Hz), 8.20 (2H, d, J=7 Hz). MS (FAB): m/z 354 (M+H)$^+$, 298 (M+H-56)$^+$.

b) Using 5-benzoyloxy-2-(tert-butoxycarbonylamino) indan (130 mg, 0.37 mmol), 4N hydrochloric acid-dioxane (2 ml) and acetic acid (6 ml), a similar procedure to Production Example 213 was carried out to obtain 5-benzoyloxy-2-aminoindan hydrochloride (67 mg, 0.35 mmol) having the following physical properties:

$^1$H NMR (400 MHz, DMSO-d$_6$): δ 3.00 (2H, m), 3.31 (2H, s), 4.06 (1H, m), 7.11 (1H, dd, J=2 Hz, 8 Hz), 7.21 (1H, d, J=2 Hz), 7.36 (1H, d, J=8 Hz), 7.61 (2H, t, J=8 Hz), 7.56 (1H, t, J=7 Hz), 8.12 (2H, d, J=7 Hz), 8.20 (3H, br. s).

c) Using 5-benzoyloxy-2-aminoindan hydrochloride (67 mg, 0.35 mmol), 4-chloro-5-methylthieno[2,3-d]pyrimidine (68 mg, 0.37 mmol), triethylamine (0.52 ml, 3.7 mmol), and ethanol (6 ml), a similar procedure to b) in Production Example 208 was carried out. The product obtained was purified by silica gel chromatography (hexane:ethyl acetate= 2:1) to obtain the title compound (70 mg, 0.17 mmol) having the following physical properties:

$^1$H NMR (400 MHz, CDCl$_3$):δ 2.51 (3H, s), 2.96 (2H, m), 3.53 (2H, m), 5.17 (1H, m), 5.65 (1H, br. d), 6.82 (1H, s), 7.04 (1H, dd, J=2 Hz, 8 Hz), 7.13 (1H, s), 7.30 (1H, d, J=8 Hz), 7.51 (2H, t, J=8 Hz), 7.64 (1H, t, J=8 Hz), 8.20 (2H, d, J=8 Hz), 8.48 (1H, s). MS (FAB): m/z 402 (M+H)$^+$.

Production Example 226

6-(2-Indanylamino)purine

Using 6-chloropurine (150 mg, 1.0 mmol), 2-aminoindan (200 mg, 1.5 mmol), and ethanol (6 ml), a similar procedure to Production Example 190 was carried out. The precipitate obtained was crystallized from ethanol to obtain the title compound (100 mg, 0.40 mmol) having the following physical properties:

mp; 300° C. or higher $^1$H NMR (400 MHz, DMSO-d$_6$): δ 3.03 (2H, m), 3.27 (2H, m), 5.00 (1H, m), 7.16 (2H, m), 7.23 (2H, m), 7.79 (1H, br. s), 8.09 (1H, br. s), 8.21 (1H, br. s), 13.0 (1H, br.). MS (FAB): m/z 252 (M+H)$^+$.

Production Example 227

4-(2-Indanylamino)thieno[3,2-d]pyrimidine a) 3-aminothiophene-2-carboxylic acid methylester (1.6 g, 10 mmol) was added to formamide (3.4 ml), and the mixture was stirred at 200° C. for 2 hours. The reaction mixture was returned to room temperature, and water was added thereto, which was extracted with chloroform. The solid obtained by distilling off the solvent under reduced pressure was washed with ethyl acetate to obtain 4-hydroxythieno[3,2-d]pyrimidine (60 mg, 0.39 mmol).

$^1$H NMR (400 MHz, DMSO-d$_6$): δ 7.40 (1H, m), 8.14 (1H, s), 8.18 (1H, m), 12.47 (1H, broad).

b) Using 4-hydroxythieno[3,2-d]pyrimidine (60 mg, 0.39 mmol), and phosphorus oxychloride (0.6 ml), and then 2-aminoindan (210 mg, 1.56 mmol), a similar procedure to Production Example 194 was carried out. The product obtained was purified by silica gel chromatography (hexane:ethyl acetate=1:2) to obtain the title compound (30 mg, 0.11 mmol) having the following physical properties:

$^1$H NMR (400 MHz, DMSO-d$_6$): δ 3.02 (2H, dd, J=6 Hz, 16 Hz), 3.32 (2H, m), 4.98 (1H, m), 7.16 (2H, m), 7.25 (2H, m), 7.37 (1H, d, J=5 Hz), 8.08 (1H, m), 8.09 (1H, d, J=5 Hz), 8.48 (1H, s). MS (FAB): m/z 268 (M+H)$^+$.

Example 1

Study of NF-κB Inhibitory Action of Test Compounds

Using lipofectamine (Lifetech Oriental K. K., Tokyo) according to the conventional method, human lung cancer cell line A549 cells (ATCC catalog no. CCL185), which are known to express hiNOS by cytokine stimulation, were co-transfected with pNFκB-Luc, which are plasmid controlled by a NF-κB binding consensus sequence, and pSV2neo (Clontech, U.S.A.), and then A549/NF-κBLuc, the cell that has stably introduced pNFκB-Luc, was selected by adding G418 sulfate (1 mg/ml, Lifetech Oriental K. K.) to the culture medium.

It was confirmed and revealed that when A549/NF-κBLuc is stimulated with IL-1β (1 ng/ml) or TNF-α (500 ng/ml) for 4 hours, the compound obtained in Production Example 4 suppresses luciferase activity that has been regulated by the activation of NF-κB in dose-dependent manner (FIG. 1). The luciferase activity was measured using the Luciferase Assay System (Promega, U.S.A.). IC50 values of the compounds obtained in the Production Examples are also shown in Table 1.

TABLE 1

| Test Compounds | IC50 (μM) IL-1 stimulation | TNF stimulation |
|---|---|---|
| Prod. Ex. 3 | 29 | |
| Prod. Ex. 4 | 10 | 10 |
| Prod. Ex. 7 | 4 | 10 |
| Prod. Ex. 9 | 3 | 4 |
| Prod. Ex. 23 | 42 | |
| Prod. Ex. 27 | 15 | |
| Prod. Ex. 28 | 14 | |
| Prod. Ex. 29 | 13 | |
| Prod. Ex. 30 | 14 | |
| Prod. Ex. 32 | 24 | |
| Prod. Ex. 33 | 28 | |
| Prod. Ex. 34 | 29 | |
| Prod. Ex. 35 | 8 | |
| Prod. Ex. 37 | 49 | |
| Prod. Ex. 39 | 39 | |
| Prod. Ex. 42 | 22 | |
| Prod. Ex. 43 | 21 | |
| Prod. Ex. 44 | 39 | |
| Prod. Ex. 45 | 17 | |
| Prod. Ex. 46 | 17 | |
| Prod. Ex. 47 | 21 | |
| Prod. Ex. 48 | 18 | |
| Prod. Ex. 49 | 28 | |
| Prod. Ex. 50 | 16 | |
| Prod. Ex. 51 | 18 | |
| Prod. Ex. 53 | 8 | |
| Prod. Ex. 54 | 5 | |
| Prod. Ex. 55 | 7 | |
| Prod. Ex. 56 | 5 | |
| Prod. Ex. 58 | 13 | |
| Prod. Ex. 59 | 12 | |
| Prod. Ex. 60 | 18 | |
| Prod. Ex. 61 | 24 | |
| Prod. Ex. 63 | 2 | |
| Prod. Ex. 64 | 5 | |
| Prod. Ex. 65 | 12 | |
| Prod. Ex. 66 | 3 | |
| Prod. Ex. 70 | 44 | |
| Prod. Ex. 71 | 56 | |
| Prod. Ex. 72 | 42 | |
| Prod. Ex. 73 | 34 | |
| Prod. Ex. 76 | 14 | |
| Prod. Ex. 79 | 13 | |
| Prod. Ex. 81 | 5 | |
| Prod. Ex. 83 | 1 | |
| Prod. Ex. 85 | 5 | |
| Prod. Ex. 94 | 1 | |
| Prod. Ex. 96 | 17 | |
| Prod. Ex. 103 | 10 | |
| Prod. Ex. 104 | 12 | |
| Prod. Ex. 105 | 16 | |
| Prod. Ex. 106 | 7 | |

TABLE 1-continued

| Test Compounds | IC50 (μM) IL-1 stimulation | TNF stimulation |
|---|---|---|
| Prod. Ex. 111 | 14 | |
| Prod. Ex. 113 | 16 | |
| Prod. Ex. 120 | 2 | |
| Prod. Ex. 121 | 7 | |
| Prod. Ex. 128 | 19 | |
| Prod. Ex. 136 | 18 | |
| Prod. Ex. 137 | 7 | |
| Prod. Ex. 147 | 47 | |
| Prod. Ex. 148 | 25 | |
| Prod. Ex. 151 | 20 | |
| Prod. Ex. 154 | 28 | |
| Prod. Ex. 163 | 19 | |
| Prod. Ex. 167 | 15 | |
| Prod. Ex. 168 | 9 | |
| Prod. Ex. 169 | 43 | |
| Prod. Ex. 173 | 36 | |
| Prod. Ex. 175 | 19 | |
| Prod. Ex. 189 | 28 | |
| Prod. Ex. 190 | 0.71 | 1.1 |
| Prod. Ex. 211 | 0.064 | 0.13 |
| Prod. Ex. 214 | 0.15 | |
| Prod. Ex. 220 | 0.072 | 0.12 |
| Prod. Ex. 221 | 0.051 | 0.089 |

Example 2

Survival Rate Improvement Effect of NF-κB Inhibitor in a Murine Myocarditis Model (1)

Viral myocarditis mice were prepared using the procedure described below in accordance with a known method (Shioi T. et al. (1997) J. Mol. Cell. Cardiol., 29, 2327–2334). Variant M (acquired from the American Type Culture Collection) was used for the EMC virus for inoculation and prepared to 100 pfu/ml in Eagle's MEM medium (Nissui Pharmaceutical). Four-week-old DBA/2 male mice were divided into two groups, and intraperitoneally inoculated with EMC virus at 10 pfu/animal. Test compound was then administered intraperitoneally and daily for 14 days under the following conditions to each group starting 3 hours after inoculation.

The test compound was used after dissolving in 0.5% aqueous gum arabic solution (3 mg/ml). In the present example, the compound of Production Example 4 was used in the test as the NF-κB inhibitor.

Test group (n=10): Administration of NF-κB inhibitor (Production Example 4) at 30 mg/kg body weight
Control group (n=10): 0.5% aqueous gum arabic solution As a result, it was shown that NF-κB inhibitor (Production Example 4) improves the survival rate as shown in FIG. 2.

Example 3

Survival Rate Improvement Effect of NF-κB Inhibitor in a Murile Myocarditis Model (2)

The experiment was conducted in the following three groups using the same method as Example 2 and the compound of Production Example 7 for the NF-κB inhibitor. The test compound was used after dissolving in 10% aqueous dimethylsulfoxide solution (DMSO) (test group 1: 0.3 mg/ml, test group 2: 3 mg/ml). The survival rates were tested for the presence of a significant difference according to the Kaplan-Meier method, and statistical significance was defined as p<0.05.

Figure 3:
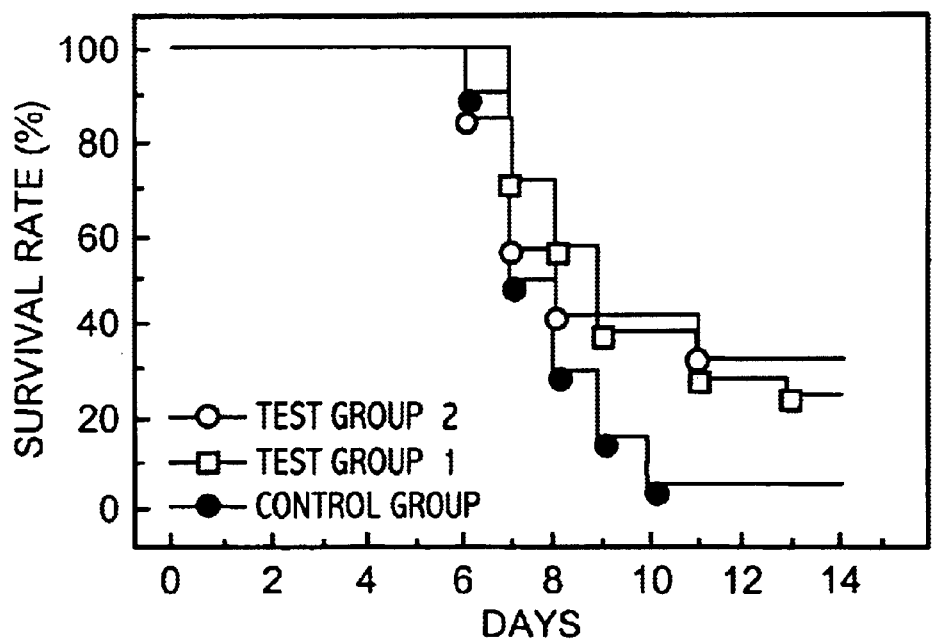
FIG. 3 is a graph showing that the NF-κB inhibiting compound obtained in Production Example 7 improves survival rates in murine models of viral myocarditis.

Test group 1 (n=21): Administration of NF-κB inhibitor (Production Example 7) at 3 mg/kg body weight Test group 2 (n=21): Administration of NF-κB inhibitor (Production Example 7) at 30 mg/kg body weight Control group (n=20): 10% DMSO As a result, NF-κB inhibitor (compound of Production Example 7) was shown to significantly improve survival rate at both 3 mg/kg and 30 mg/kg as shown in FIG. 3.

Example 4

Survival Rate Improvement Effect of NF-κB Inhibitor in a Murine Myocarditis Model (3)

Four-week-old DBA/2 male mice were inoculated with EMC virus using the same method as Example 2, and the test compound was administered orally and daily for 14 days under the following conditions to each group starting 2 hours after inoculation.

The test compound was used after dissolving in 10% aqueous sulfobutylcyclodextrin solution (3 mg/ml). In the present example, the compound of Production Example 44 was used in the test as the NF-κB inhibitor.

Figure 4:
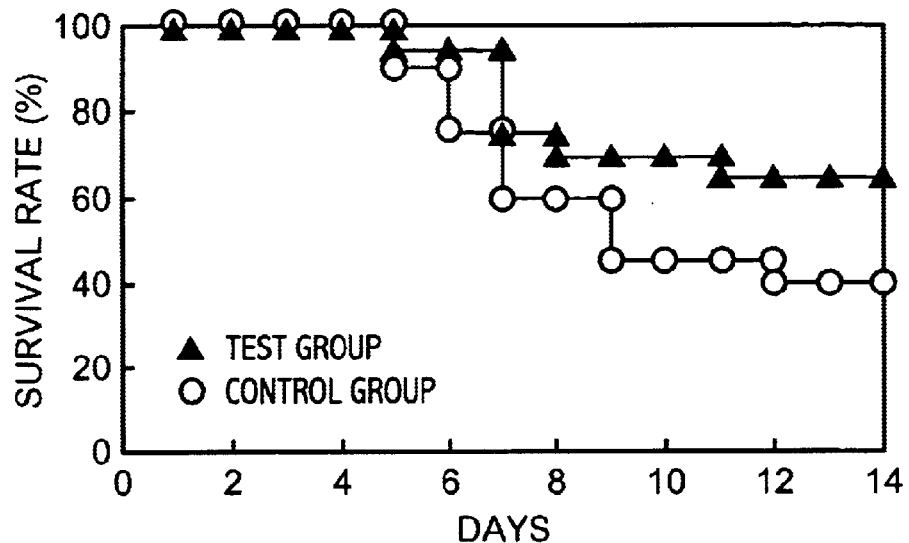
FIG. 4 is a graph showing that the NF-κB inhibiting compound obtained in Production Example 44 improves survival rates in murine models of viral myocarditis.

Test group (n=20): Administration of NF-κB inhibitor (Production Example 44) at 30 mg/kg body weight Control group (n=20): 10% aqueous sulfobutylcyclodextrin solution As a result, it was shown that orally administered NF-κB inhibitor (compound of Production Example 44) improves survival rate as shown in FIG. 4.

Example 5

Inhibitory Action of NF-κB Inhibitor to Cardiac Necrosis and Cellular Infiltration in a Murine Myocarditis Model NF-κB inhibitor (compound of Production Example 7) was administered at 30 mg/kg body weight using the similar method as Example 3 to the mouse myocarditis model prepared in the similar manner as Example 2. The whole hearts of those mice alive on days 7 and 8 (n=10) were extripated, exsanguinated and washed with phosphate-buffered saline. Subsequently, paraffin embedded and sectioned specimens were prepared by fixing the tissue with 10% formalin. The specimens were stained with hematoxylin-eosin stain followed by examination of histopathological findings.

In cross-sectional images taken along the minor axis of the left ventricle under light microscopy, the percentage of cardiac necrosis features or cellular infiltration was classified into 0 (no damage), 1 (less than 25%), 2 (25% to less than 50%), 3 (50% to less than 75%) and 4 (75% or more), and respectively observed by two observers. The evaluations of the two observers were averaged to obtain a single evaluation. The results obtained were tested for the presence of a significant difference by analysis of variance (ANOVA) according to Bonferroni's multiple comparison method, and statistical significance was defined as p<0.05.

Figure 5A:
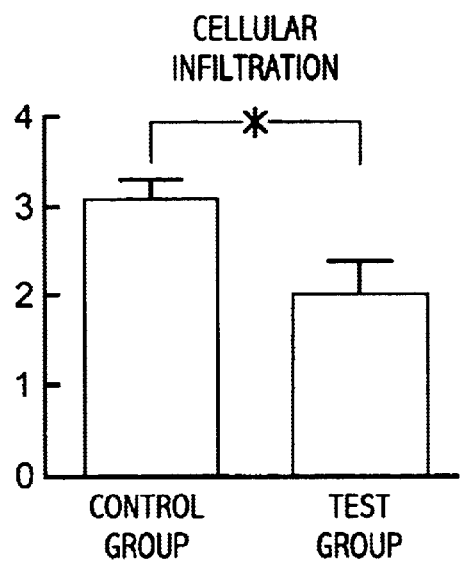
FIG. 5 is a graph showing that the NF-κB inhibiting compound obtained in Production Example 7 significantly suppresses infiltration of inflammatory cells and cardiac necrosis.
Figure 5B:
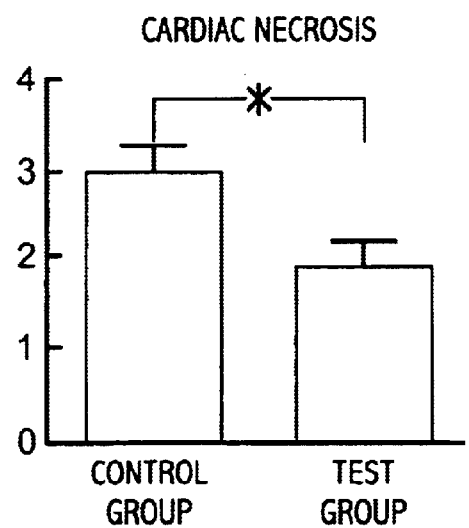

Test group (n=10): Administration of NF-κB inhibitor (Production Example 7) at 30 mg/kg body weight Control group (n=10): 10% DMSO As shown in FIG. 5, cellular infiltration and cardiac necrosis, which are characteristic findings of myocarditis, were significantly inhibited in all animals of the group administered NF-κB inhibitor (Production Example 7) as compared with the control group, and the present compound was shown to demonstrate remarkable ameliorative effects based on pathological findings as well.

Example 6

Inhibitory Action on Expression of Inflammatory Protein by NF-κB Inhibitor in a Murine Myocarditis Model Four-week-old DBA/2 male mice were inoculated with EMC virus in the same manner as Example 3 followed by intraperitoneal administration of the compound of Production Example 7 dissolved in 10% DMSO or 10% DMSO only daily for 5 days starting 2 hours after inoculation. The whole hearts were excised from mice of the Production Example 7 compound group, 10% DMSO group and non-infected group on day 5 of viral infection, and after extracting RNA using ISOGEN (Wako Pure Chemical Industries), cDNA was obtained in accordance with the procedure of the SuperScript Preamplification System (Lifetech Oriental). The mRNA levels of TNF-α, IL-1β and iNOS were assayed by TaqMan PCR using this cDNA as templates. Detection was performed using the PRISM7700 (PE Biosystems Japan) in accordance with the protocol of the PCR assay system (PE Biosystems Japan). The following primers and TaqMan probes were used for detection.

TNF-α

Forward: CAT CTT CTC AAA ATT CGA GTG ACA A (Sequence ID No. 1)

Reverse: TGG GAG TAG ACA AGG TAC AAC CC (Sequence ID No. 2)

Probe: CAC GTC GTA GCA AAC CAC CAA GTG GA (Sequence ID No. 3)

IL-1β

Forward: CAA CCA ACA AGT GAT ATT CTC CAT G (Sequence ID No. 4)

Reverse GAT CCA CAC TCT CCA GCT GCA (Sequence ID No. 5)

Probe: CTG TGT AAT GAA AGA CGG CAC ACC CAC C (Sequence ID No. 6)

iNOS

Forward: CAG CTG GGC TGT ACA AAC CTT (Sequence ID No. 7)

Reverse: CAT TGG AAG TGA AGC GTT TCG (Sequence ID No. 8)

Probe: CGG GCA GCC TGT GAG ACC TTT GA (Sequence ID No. 9)

The amount of RNA of each sample was corrected with the amount of glyceraldehyde-3-phosphate dehydrogenase (GAPDH) gene.

Non-infected group (n-3) Not administered

Infected group (control) (n=10) 10% DMSO

Infected group (administered compound of Production Example 7) (n=10) Administration of NF-κB inhibitor (Production Example 7) at 30 mg/kg body weight As shown in FIG. 6, in the infected group administered the compound obtained in Production Example 7 having NF-κB inhibitory action (Production Example 7 Group), the expression of TNF-α, IL-1β and iNOS was significantly inhibited at the mRNA level with respect to the infected group (control). This indicated that NF-κB inhibitor inhibits the expression of inflammatory proteins such as TNF-α, IL-1β and iNOS, which are the cause of myocarditis, dilated cardiomyopathy and heart failure, and that it is useful as a drug for the prevention or treatment of myocarditis, dilated cardiomyopathy and heart failure.

Industrial Application

A substance having NF-κB inhibitory action is useful for the prevention or treatment of myocarditis, dilated cardiomyopathy and heart failure.

What is claimed is:

1. A method for treating myocarditis, dilated cardiomyopathy and heart failure comprising administering to a patient in need of such treatment a NF-κB inhibitor in a therapeutically effective amount, wherein said NF-κB inhibitor is a benzoquinone derivative represented by the following formula (I):

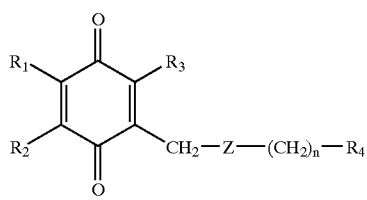

wherein $R_1$, $R_2$ and $R_3$ are each independently a hydrogen atom, an alkyl group having 1 to 5 carbons or an alkoxy group having 1 to 5 carbons;

$R_4$ is a hydrogen atom, a hydroxymethyl group, an alkyl group, or a carboxyl group which is optionally esterified or amidated;

Z is

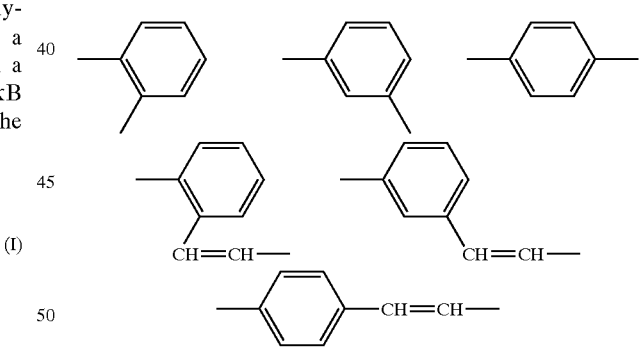

and n is an integer from 0 to 6,
or its hydroquinone form, or a pharmaceutically acceptable salt thereof.

2. The method according to claim 1, wherein $R_1$ and $R_2$ are each independently a methyl group or methoxy group; $R_3$ is a methyl group, $R_4$ is a carboxyl group which is optionally esterified or amidated.

3. The method according to claim 2, wherein the carboxyl group of $R_4$ is esterified or amidated.

4. The method according to claim 3, wherein $R_4$ is —CONR$_6$R$_7$ and $R_6$ and $R_7$ together form a 5- to 10-membered nitrogen-containing heterocyclic group together with the nitrogen atom to which they are attached.

5. The method according to claim 4, wherein $R_4$ further comprises 1 to 3 heteroatoms selected from the group consisting of a nitrogen, oxygen and sulfur atom.

6. The method according to claim 4, wherein $R_6$ and $R_7$ are each independently a hydrogen atom or an optionally substituted alkyl group having 1 to 8 carbons.

7. The method according to claim 6, wherein the optionally substituted alkyl group is isopropylamino.

8. The method according to claim 1, wherein n is an integer 0, 1, 2 or 3.

9. The method according to claim 1, wherein $R_1$ and $R_2$ are each independently a methyl group or methoxy group; $R_3$ is a hydrogen atom or a methyl group, $R_4$ is a carboxyl group which is optionally esterified or amidated; Z is

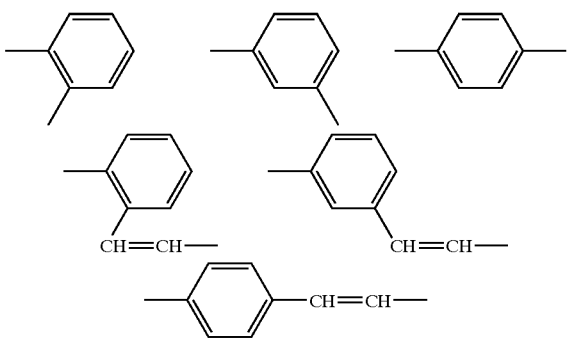

and n is 0 or 2.

10. A method for suppressing necrosis of cardiac muscle cells comprising administering to a patient in need of such suppression a NF-κB inhibitor in a therapeutically effective amount, wherein said NF-κB inhibitor is a benzoquinone derivative represented by the following formula (I):

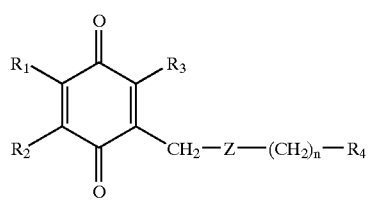

(I)

wherein
$R_1$, $R_2$ and $R_3$ are each independently a hydrogen atom, an alkyl group having 1 to 5 carbons or an alkoxy group having 1 to 5 carbons;
$R_4$ is a hydrogen atom, a hydroxymethyl group, an alkyl group, or a carboxyl group which is optionally esterified or amidated;
Z is

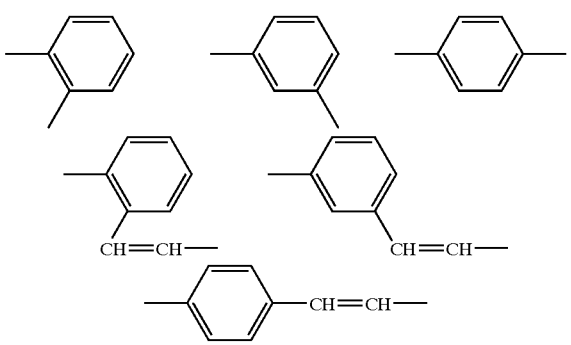

and n is an integer from 0 to 6,
or its hydroquinone form, or a pharmaceutically acceptable salt thereof.

11. The method according to claim 10, wherein $R_1$ and $R_2$ are each independently a methyl group or methoxy group; $R_3$ is a methyl group, $R_4$ is a carboxyl group which is optionally esterified or amidated.

12. The method according to claim 11, wherein the carboxyl group of $R_4$ is esterified or amidated.

13. The method according to claim 12, wherein $R_4$ is —CONR$_6$R$_7$ and $R_6$ and $R_7$ together form a 5- to 10-membered nitrogen-containing heterocyclic group together with the nitrogen atom to which they are attached.

14. The method according to claim 13, wherein $R_4$ further comprises 1 to 3 heteroatoms selected from the group consisting of a nitrogen, oxygen and sulfur atom.

15. The method according to claim 13, wherein $R_6$ and $R_7$ are each independently a hydrogen atom or an optionally substituted alkyl group having 1 to 8 carbons.

16. The method according to claim 15, wherein the optionally substituted alkyl group is isopropylamino.

17. The method according to claim 10, wherein n is an integer 0, 1, 2 or 3.

18. The method according to claim 10, wherein $R_1$ and $R_2$ are each independently a methyl group or methoxy group; $R_3$ is a hydrogen atom or a methyl group, $R_4$ is a carboxyl group which is optionally esterified or amidated; Z is

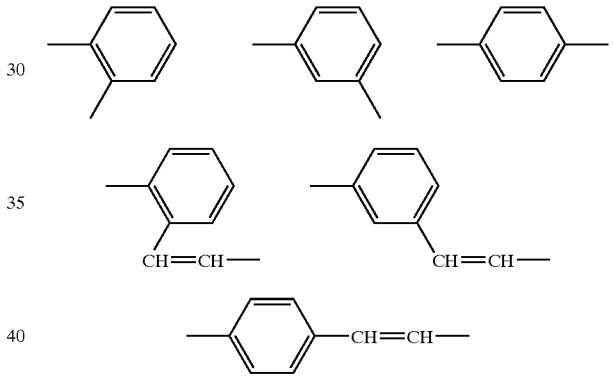

and n is 0 or 2.

19. A method for diminishing or eliminating infiltration of inflammatory cells into a patient's heart comprising administering to a patient in need of such diminishing or eliminating of infiltration a NF-κB inhibitor in a therapeutically effective amount, wherein said NF-κB inhibitor is a benzoquinone derivative represented by the following formula (I):

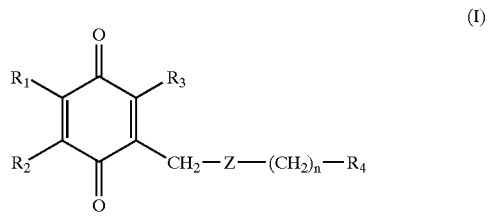

(I)

wherein $R_1$, $R_2$ and $R_3$ are each independently a hydrogen atom, an alkyl group having 1 to 5 carbons or an alkoxy group having 1 to 5 carbons;
$R_4$ is a hydrogen atom, a hydroxymethyl group, an alkyl group, or a carboxyl group which is optionally esterified or amidated;

Z is

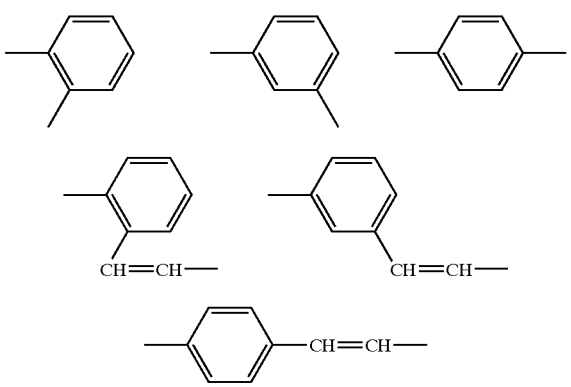

and n is an integer from 0 to 6,
or its hydroquinone form, or a pharmaceutically acceptable salt thereof.

20. The method according to claim 19, wherein $R_1$ and $R_2$ are each independently a methyl group or methoxy group; $R_3$ is a methyl group, $R_4$ is a carboxyl group which is optionally esterified or amidated.

21. The method according to claim 20, wherein the carboxyl group of $R_4$ is esterified or amidated.

22. The method according to claim 21, wherein $R_4$ is —$CONR_6R_7$ and $R_6$ and $R_7$ together form a 5- to 10-membered nitrogen-containing heterocyclic group together with the nitrogen atom to which they are attached.

23. The method according to claim 22, wherein $R_4$ further comprises 1 to 3 heteroatoms selected from the group consisting of a nitrogen, oxygen and sulfur atom.

24. The method according to claim 22, wherein $R_6$ and $R_7$ are each independently a hydrogen atom or an optionally substituted alkyl group having 1 to 8 carbons.

25. The method according to claim 24, wherein the optionally substituted alkyl group is isopropylamino.

26. The method according to claim 19, wherein n is an integer 0, 1, 2 or 3.

27. The method according to claim 19, wherein $R_1$ and $R_2$ are each independently a methyl group or methoxy group; $R_3$ is a hydrogen atom or a methyl group, $R_4$ is a carboxyl group which is optionally esterified or amidated; Z is

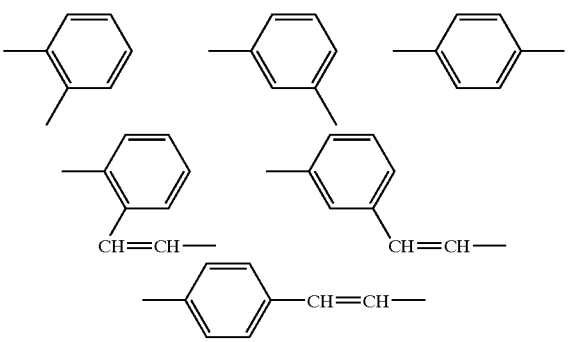

and n is 0 or 2.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: TNF-alpha forward primer

<400> SEQUENCE: 1
catcttctca aaattcgagt gacaa                                              25

<210> SEQ ID NO 2
<211> LENGTH: 23
<212> TYPE: DNA
<213> ORGANISM: Artificial Sequence
<220> FEATURE:
<223> OTHER INFORMATION: TNF-alpha reverse primer

<400> SEQUENCE: 2
tgggagtaga caaggtacaa ccc                                                23

<210> SEQ ID NO 3
<211> LENGTH: 26
<212> TYPE: DNA
<213> ORGANISM: Artificial Sequence
<220> FEATURE:
<223> OTHER INFORMATION: TNF-alpha probe

<400> SEQUENCE: 3
cacgtcgtag caaaccacca agtgga                                             26

<210> SEQ ID NO 4
<211> LENGTH: 25
<212> TYPE: DNA
<213> ORGANISM: Artificial Sequence
<220> FEATURE:
<223> OTHER INFORMATION: IL-1b forward primer

<400> SEQUENCE: 4
caaccaacaa gtgatattct ccatg                                              25

<210> SEQ ID NO 5
<211> LENGTH: 21
<212> TYPE: DNA
<213> ORGANISM: Artificial Sequence
<220> FEATURE:
<223> OTHER INFORMATION: IL-1b reverse primer

<400> SEQUENCE: 5
gatccacact ctccagctgc a                                                  21

<210> SEQ ID NO 6
<211> LENGTH: 28
<212> TYPE: DNA
<213> ORGANISM: Artificial Sequence
<220> FEATURE:
<223> OTHER INFORMATION: IL-1b probe

```
<400> SEQUENCE: 6
ctgtgtaatg aaagacggca cacccacc                                    28

<210> SEQ ID NO 7
<211> LENGTH: 21
<212> TYPE: DNA
<213> ORGANISM: Artificial Sequence
<220> FEATURE:
<223> OTHER INFORMATION: iNOS forward primer

<400> SEQUENCE: 7
cagctgggct gtacaaacct t                                           21

<210> SEQ ID NO 8
<211> LENGTH: 21
<212> TYPE: DNA
<213> ORGANISM: Artificial Sequence
<220> FEATURE:
<223> OTHER INFORMATION: iNOS reverse primer

<400> SEQUENCE: 8
cattggaagt gaagcgtttc g                                           21

<210> SEQ ID NO 9
<211> LENGTH: 23
<212> TYPE: DNA
<213> ORGANISM: Artificial Sequence
<220> FEATURE:
<223> OTHER INFORMATION: iNOS probe

<400> SEQUENCE: 9
cgggcagcct gtgagacctt tga                                         23
```